United States Patent
Drewry et al.

(10) Patent No.: US 7,560,467 B2
(45) Date of Patent: Jul. 14, 2009

(54) INDAZOLO-TETRAHYDROPYRIMIDINE-CARBOXAMIDE DERIVATIVE KINASE INHIBITORS

(75) Inventors: David Harold Drewry, Durham, NC (US); Brian Evans, Stevenage (GB); Krista B. Goodman, King of Prussia, PA (US); Darren Victor Steven Green, Stevenage (GB); David Kendall Jung, Durham, NC (US); Dennis Lee, King of Prussia, PA (US); Robert A. Stavenger, King of Prussia, PA (US); Sjoerd Nocolaas Wadman, Obermorschwiller (FR)

(73) Assignee: SmithKline Beecham Corporation, Philadelphia, PA (US)

( * ) Notice: Subject to any disclaimer, the term of this patent is extended or adjusted under 35 U.S.C. 154(b) by 597 days.

(21) Appl. No.: 10/560,502

(22) PCT Filed: Jun. 18, 2004

(86) PCT No.: PCT/US2004/019692

§ 371 (c)(1),
(2), (4) Date: Dec. 13, 2005

(87) PCT Pub. No.: WO2004/112719

PCT Pub. Date: Dec. 29, 2004

(65) Prior Publication Data

US 2007/0099944 A1    May 3, 2007

Related U.S. Application Data

(60) Provisional application No. 60/479,753, filed on Jun. 19, 2003.

(51) Int. Cl.
*C07D 403/12* (2006.01)
*A61K 31/416* (2006.01)

(52) U.S. Cl. .................... 514/274; 544/316

(58) Field of Classification Search ............... 544/316; 514/274
See application file for complete search history.

(56) References Cited

U.S. PATENT DOCUMENTS

2008/0125427 A1* 5/2008 Sehon et al. ............ 514/234.5

FOREIGN PATENT DOCUMENTS

| EP | 1223170 | | 7/2002 |
|---|---|---|---|
| EP | 1380576 | A1 | 1/2004 |
| EP | 1403255 | A1 | 3/2004 |
| WO | 0250065 | A2 | 6/2002 |
| WO | 02083648 | A1 | 10/2002 |
| WO | 02100833 | A1 | 12/2002 |

OTHER PUBLICATIONS

Simone, Oncology: Introduction, Cecil Textbook of Medicine, 20th Edition, vol. 1, pp. 1004-1010, 1996.*
Traxler, Protein Tyrosine Kinase Inhibitors in cancer treatment, Expert Opinion on Therapeutic Patents, 7(6):571-588, 1997.*
West, Solid Solutions, Solid state chemistry and it's applications, Wiley, New York, pp. 358 and 365, 1988.*
Vippagunta et al., Crystalline solids, Advanced Drug Delivery Reviews, 48 (2001), pp. 3-26, 2001.*
Ulrich, Crystallization, Kirk-Othmer Encyclopedia of Chemical Technology, vol. 8, pp. 113-120, (http://www.mrw.interscience.wiley.com/kirk/articles/crysrous.a01/sect4-fs.html) Aug. 2002.*
EP Search Report dated Oct. 21, 2008.

* cited by examiner

*Primary Examiner*—Deepak Rao
(74) *Attorney, Agent, or Firm*—Kathryn L. Coulter; John L. Lemanowicz

(57) ABSTRACT

The present invention relates to indazolo-tetrahydropyrimidine-carboxamide derivatives, compositions and medicaments containing the same, as well as processes for the preparation and use of such compounds, compositions and medicaments. Such indazolo-tetrahydropyrimidine-carboxamide derivatives are useful in the treatment of diseases associated with inappropriate ROCK-1 kinase.

7 Claims, No Drawings

SEQUENCE LISTING

<160> NUMBER OF SEQ ID NOS: 1

<210> SEQ ID NO 1
<211> LENGTH: 11
<212> TYPE: PRT
<213> ORGANISM: Artificial Sequence
<220> FEATURE:
<223> OTHER INFORMATION: Substrate peptide for ROCK assay.

<400> SEQUENCE: 1

Ala Lys Arg Arg Arg Leu Ser Ser Leu Arg Ala
 1               5                   10

INDAZOLO-TETRAHYDROPYRIMIDINE-CARBOXAMIDE DERIVATIVE KINASE INHIBITORS

CROSS-REFERENCE TO RELATED APPLICATIONS

This application is filed pursuant to 35 U.S.C. 371 as a United States National Phase Application of International Application No. PCT/US2004/19692, filed Jun. 18, 2004, which claims the benefit of U.S. Provisional Application No. 60/479,753, filed Jun. 19, 2003.

FIELD OF THE INVENTION

The present invention relates to indazole amide derivatives, compositions and medicaments containing the same, as well as processes for the preparation and use of such compounds, compositions and medicaments. Such indazole amide derivatives are useful in the treatment of diseases associated with inappropriate tyrosine and/or serine/threonine kinase activity.

BACKGROUND OF THE INVENTION

An important large family of enzymes is the protein kinase enzyme family. Currently, there are about 500 different known protein kinases. Protein kinases serve to catalyze the phosphorylation of an amino acid side chain in various proteins by the transfer of the γ-phosphate of the ATP-$Mg^{2+}$ complex to said amino acid side chain. These enzymes control the majority of the signaling processes inside cells, thereby governing cell function, growth, differentiation and destruction (apoptosis) through reversible phosphorylation of the hydroxyl groups of serine, threonine and tyrosine residues in proteins. Studies have shown that protein kinases are key regulators of many cell functions, including signal transduction, transcriptional regulation, cell motility, and cell division. Several oncogenes have also been shown to encode protein kinases, suggesting that kinases play a role in oncogenesis. These processes are highly regulated, often by complex intermeshed pathways where each kinase will itself be regulated by one or more kinases. Consequently, aberrant or inappropriate protein kinase activity can contribute to the rise of disease states associated with such aberrant kinase activity. Due to their physiological relevance, variety and ubiquitousness, protein kinases have become one of the most important and widely studied family of enzymes in biochemical and medical research.

The protein kinase family of enzymes is typically classified into two main subfamilies: Protein Tyrosine Kinases and Protein Serine/Threonine Kinases, based on the amino acid residue they phosphorylate. The serine/threonine kinases (PSTK), includes cyclic AMP- and cyclic GMP-dependent protein kinases, calcium- and phospholipid-dependent protein kinase, calcium- and calmodulin-dependent protein kinases, casein kinases, cell division cycle protein kinases and others. These kinases are usually cytoplasmic or associated with the particulate fractions of cells, possibly by anchoring proteins. Aberrant protein serine/threonine kinase activity has been implicated or is suspected in a number of pathologies such as rheumatoid arthritis, psoriasis, septic shock, bone loss, many cancers and other proliferative diseases. Accordingly, serine/threonine kinases and the signal transduction pathways which they are part of are important targets for drug design. The tyrosine kinases phosphorylate tyrosine residues. Tyrosine kinases play an equally important role in cell regulation. These kinases include several receptors for molecules such as growth factors and hormones, including epidermal growth factor receptor, Insulin receptor, platelet derived growth factor receptor and others. Studies have indicated that many tyrosine kinases are transmembrane proteins with their receptor domains located on the outside of the cell and their kinase domains on the inside. Much work is also under progress to identify modulators of tyrosine kinases as well.

A major signal transduction systems utilized by cells is the RhoA signalling pathways. RhoA is a small GTP binding protein that can be activated by several extracellular stimuli such as growth factor, hormones, mechanic stress, osmotic change as well as high concentration of metabolite like glucose. RhoA activation involves. GTP binding, conformation alteration, post-translational modification (geranylgeranyllization and farnesylation) and activation of its intrinsic GTPase activity. Activated RhoA is capable of interacting with several effector proteins including ROCKs and transmit signals into cellular cytoplasm and nucleus.

ROCK1 and 2 constitute a family of kinases that can be activated by RhoA-GTP complex via physical association. Activated ROCKs phosphorylate a number of substrates and play important roles in pivotal cellular functions. The substrates for ROCKs include myosin binding subunit of myosin light chain phosphatase (MBS, also named MYPT1), adducin, moesin, myosin light chain (MLC), LIM kinase as well as transcription factor FHL. The phosphorylation of theses substrates modulate the biological activity of the proteins and thus provide a means to alter cell's response to external stimuli. One well documented example is the participation of ROCK in smooth muscle contraction. Upon stimulation by phenylephrine, smooth muscle from blood vessels contracts. Studies have shown that phenylephrine stimulates b-adrenergic receptors and leads to the activation of RhoA. Activated RhoA in turn stimulates kinase activity of ROCK1 and which in turn phosphorylates MBS. Such phosphorylation inhibits the enzyme activity of myosin light chain phosphatase and increases the phosphorylation of myosin light chain itself by a calcium-dependent myosin light chain kinase (MLCK); and consequently increases the contractility of myosin-actin bundle, leading to smooth muscle contraction. This phenomena is also sometimes called calcium sensitization. In addition to smooth muscle contraction, ROCKs have also been shown to be involved in cellular functions including apoptosis, cell migration, transcriptional activation, fibrosis, cytokinesis, inflammation and cell proliferation. Moreover, in neurons ROCK plays a critical role in the inhibition of axonal growth by myelin-associated inhibitory factors such as myelin-associated glycoprotein (MAG). ROCK-activity also mediates the collapse of growth cones in developing neurons. Both processes are thought to be mediated by ROCK-induced phosphorylation of substrates such as LIM kinase and myosin light chain phosphatase, resulting in increased contractility of the neuronal actin-myosin system.

Inhibitors of ROCKs have been suggested for use in the treatments of a variety of diseases. They include cardiovascular diseases such as hypertension, chronic and congestive heart failure, cardiac hypertrophy, restenosis, chronic renal failure and atherosclerosis. In addition, because of its muscle relaxing properties, it is also suitable for asthma, male erectile dysfunctions, female sexual dysfunction and over-active bladder syndrome. ROCK inhibitors have been shown to possess anti-inflammatory properties. Thus they can be used as treatment for neuroinflammatory diseases such as stroke, multiple sclerosis, Alzheimer's disease, Parkinson's disease, amyotrophic lateral sclerosis and inflammatory pain, as well as other inflammatory diseases such as rheumatoid arthritis, irritable bowel syndrome, inflammatory bowel disease. In addition, based on their neurite outgrowth inducing effects, ROCK inhibitors could be useful drugs for neuronal regeneration, inducing new axonal growth and axonal rewiring across lesions within the CNS. ROCK inhibitors are therefore likely to be useful for regenerative (recovery) treatment of CNS disorders such as spinal cord injury, acute neuronal injury (stroke, traumatic brain injury), Parkinsons disease, Alzheimers disease and other neurodegenerative disorders. Since ROCK Inhibitors reduce cell proliferation and cell migration, they could be useful in treating cancer and tumor metastasis. Further more, there is evidence suggesting that ROCK inhibitors suppress cytoskeletal rearrangement upon virus invasion, thus they also have potential therapeutic value in anti-viral and anti-bacterial applications. ROCK inhibitors are also useful for the treatment of Insulin resistance and diabetes.

The Aurora family of serine/threonine kinase is essential for cell proliferation [Bischoff, J. R. & Plowman, G. D., The Aurora/lp11p kinase family: regulators of chromosome segregation and cytokinesis, *Trends in Cell Biology*, 9, 454-459 (1999); Giet, R. and Prigent, C., Aurora/lp11p-related kinases, a new oncogenic family of mitotic serine-threonine kinases, *Journal of Cell Sciences*, 112, 3591-3601 (1999); Nigg, E. A., Mitotic kinases as regulators of cell division and its checkpoints, Nat. Rev. *Mol. Cell. Biol.*, 2, 21-32 (2001); Adams, R. R., Carmena, M. and Earnshaw, W. C., Chromosomal passengers and the (aurora) ABC's of mitosis, *Trends in Cell Biology*, 11, 49-54 (2001); Warner, S. L. et al., Targeting Aurora-2 kinase in cancer, *Molecular Cancer Therapeutics*, 2(6), 589-595 (2003)] Inhibitors of the Aurora kinase family therefore have the potential to block growth of all tumor types.

Since its discovery in 1997, the mammalian Aurora kinase family has been closely linked to tumorigenesis. Compelling evidence for this is that over-expression of Aurora-A transforms rodent fibroblasts (Bischoff, J. R. et al., A homologue of Drosophila aurora kinase in oncogenic and amplified in human colorectal cancers, *EMBO J*. 17, 3052-3065; 1998). Cells with elevated levels of this kinase contain multiple centrosomes and multipolar spindles, and rapidly become aneuploid. The oncogenic activity of Aurora kinases is likely to be linked to the generation of such genetic instability. Indeed, a correlation between amplification of the aurora-A locus and chromosomal instability in mammary and gastric tumors has been observed. (Miyoshi, Y., Iwao, K. Egawa, C., and Noguchi, S., Association of centrosomal kinase STK15/BTAK mRNA expression with chromosomal instability In human breast cancers, *Int J. Cancer*, 92, 370-373; 2001). (Sakakura, C et al., Tumor-amplified kinase BTAK is amplified and overexpressed In gastric cancers with possible involvement In aneuploid formation, *British Journal of Cancer*, 84, 824-831; 2001). The Aurora kinases have been reported to be over-expressed in a wide range of human tumors. Elevated expression of Aurora-A has been detected in over 50% of colorectal (Bischoff, J. R. et al., A homologue of Drosophila aurora kinase is oncogenic and amplified in human colorectal cancers, *EMBO J.*, 17, 3052-3065; 1998); (Takahashi, T. et al., Centrosomal kinases, HsAIRk1 and HsAIRK3, are overexpressed in primary colorectal cancers, *Jpn. J. Cancer Res.*, 91, 1007-1014; 2000); ovarian cancers (Gritsko, T. M. et al., Activation and over-expression of centrosome kinase BTAK/Aurora-A in human ovarian cancer, *Clinical Cancer Research*, 9, 1420-1426; 2003), gastric tumors (Sakakura, C. et al., Tumor-amplified kinase BTAK is amplified and overexpressed in gastric cancers with possible involvement in aneuploid formation, *British Journal of Cancer*, 84, 824-831; 2001), 93% in pancreatic cancers (Rojanala, S. et al., The mitotic serine threonine kinase, Aurora-2, is a potential target for drug development in human pancreatic cancer, *Molecular Cancer Therapeutics*, 3(4), 451-457; 2004) and in 94% of invasive duct adenocarcinomas of the breast (Tanaka, T. et al., Centrosomal kinase AIK1 is overexpressed in invasive ductal carcinoma of the breast, *Cancer Research*, 59, 2041-2044; 1999). High levels of Aurora-A have also been reported in renal, cervical, neuroblastoma, melanoma, lymphoma, pancreatic and prostate tumor cell lines. (Bischoff, J. R. et al., A homologue of Drosophila aurora kinase is oncogenic and amplified in human colorectal cancers, *EMBO J*. 17, 3052-3065 (1998); (Kimura, M. Matsuda, Y., Yoshioka, T., and Okano, Y., Cell cycle-dependent expression and centrosomal localization of a third human Aurora/lpll-related protein kinase, AIK3, *Journal of Biological Chemistry*, 274, 7334-7340 (1999); (Zhou et al., Tumor amplified kinase STK15/BTAK Induces centrosome amplification, aneuploidy and transformation, *Nature Genetics*, 20, 189-193; 1998); (Li et al., Over-expression of oncogenic STK15/BTAK/Aurora-A kinase in human pancreatic cancer, *Clin. Cancer Res.*, 9(3), 991-7; 2003). Amplification/over-expression of Aurora-A is observed in human bladder cancers and amplification of Aurora-A is associated with aneuploidy and aggressive clinical behavior (Sen. S. et al., Amplification/over-expression of a mitotic kinase gene in human bladder cancer, *J. Natl. Cancer Inst.*, 94(17), 1320-9; 2002). Moreover, amplification of the aurora-A locus (20q13) correlates with poor prognosis for patients with node-negative breast cancer (Isola, J. J. et al., Genetic aberrations detected by comparative genomic hybridization predict outcome in node-negative breast cancer. *American Journal of Pathology*, 147, 905-911; 1995). In addition, an allelic variant, isoleucine at amino acid position 31, is reported to be a low-penetrance tumor-susceptibility gene and displays greater transforming potential than the phenylalanine-31 variant (Ewart-Toland, A. et al., Identification of Stk6/STK15 as a candidate low-penetrance tumor-susceptibility gene in mouse and human, *Nature Genetics*, 34(12), 403-412; 2003) and is associated with increased risk for advanced and metastatic disease (Miao, X. et al. Functional STK15 Phe31Ile polymorphism is associated with the occurrence and advanced disease status of esophageal squamous cell carcinoma, *Cancer Research*, 64, 2680-2683; 2004).

Aurora-B is highly expressed In multiple human tumor cell lines, including leukemic cells (Katayama et al., Human AIM-1:cDNA cloning and reduced expression during endomitosis in megakaryocyte-lineage cells, *Gene*, 244, 1-7). Levels of this enzyme increase as a function of Duke's stage in primary colorectal cancers (Katayama, H. et al., Mitotic kinase expression and colorectal cancer progression. *Journal of the National Cancer Institute*, 91, 1160-1162; 1999). Aurora-C, which is normally only found in germ cells, is also over-expressed in a high percentage of primary colorectal cancers and In a variety of tumor cell lines including cervical adenocarinoma and breast carcinoma cells (Kimura, M., Matsuda, Y., Yoshioka, T., and Okano, Y., Cell cycle-dependent expression and centrosomal localization of a third human Aurora/pll-related protein kinase AIK3, *Journal of Biological Chemistry*, 274, 7334-7340; 1999 and Takahashi, T. et al., Centrosomal kinases, HsAIRk 1 and HsAIRK3, are over-expressed in primary colorectal cancers, *Jpn. J. Cancer Res.*, 91, 1007-1014; 2000).

The present inventors have discovered novel indazole amide compounds, which are inhibitors of ROCK and/or Aurora kinase activity. Such derivatives are useful in the treatment of disorders associated with inappropriate ROCK and/or Aurora kinase activity.

SUMMARY OF THE INVENTION

In one aspect of the present invention, there is provided a compound of Formula (I):

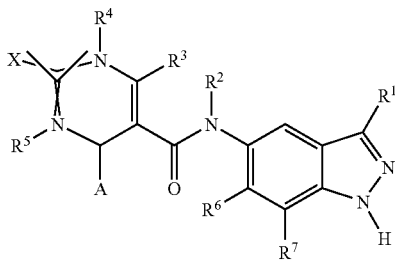

(I)

or a salt, solvate, or physiologically functional derivative thereof:

wherein:
⁓ indicates a single or double bond;
X is =O, =S, $C_1$-$C_3$ alkyl, or —N(H)R;
A is aryl, aralkyl, heteroaryl, $C_1$-$C_6$ alkyl, —CH$_2$OCH$_2$R''', $C_3$-$C_7$ cycloalkyl, $C_2$-$C_6$ alkenyl, or $C_2$-$C_6$ alkynyl;
R is $C_1$-$C_3$ alkyl, aryl, heteroaryl, —C(O)R'', —S(O)$_2$R'', or —C(O)NR'';
$R^1$ is —H, halo, $C_1$-$C_6$ alkyl, aryl, heteroaryl, or N(H)R';
$R^1$ is —H, $C_1$-$C_3$ alkyl, aryl, —C(O)R'', —S(O)$_2$R'', or —C(O)N(H)R'';
R'' is $C_1$-$C_3$ alkyl;
R''' is aryl;
$R^2$ is —H or $C_1$-$C_3$ alkyl,
$R^3$ is —H, $C_1$-$C_3$ alkyl, —CH$_2$OCH$_3$, aryl or heteroaryl; or
$R^2$ and $R^3$ together with the ring and atoms to which they are attached form a fused ring system;
$R^4$ and $R^5$ are each independently —H, $C_1$-$C_3$ alkyl or aralkyl;
$R^6$ is —H or halo; and
$R^7$ is —H, $C_1$-$C_3$ alkyl, or halo.

In a second aspect of the present invention, there is provided a compound of Formula (I'):

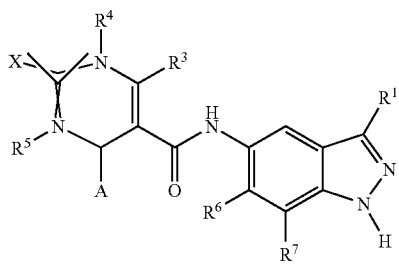

(I')

or a salt, solvate, or physiologically functional derivative thereof:

wherein:
⁓ indicates a single or double bond;
X is =O, =S, $C_1$-$C_3$ alkyl, or —N(H)R;

A is aryl, aralkyl, heteroaryl, $C_1$-$C_6$ alkyl, $C_3$-$C_7$ cycloalkyl, $C_2$-$C_6$ alkenyl, or $C_2$-$C_6$ alkynyl;
$R^1$ is $C_1$-$C_3$ alkyl, aryl, heteroaryl, —C(O)R'', —S(O)$_2$R'', or —C(O)NR'';
$R^1$ is —H, halo, $C_1$-$C_6$ alkyl, aryl, heteroaryl, or N(H)R';
$R^1$ is —H, $C_1$-$C_3$ alkyl, aryl, —C(O)R'', —S(O)$_2$R'', or —C(O)N(H)R'';
R'' is $C_1$-$C_3$alkyl;
$R^3$ is —H, $C_1$-$C_3$ alkyl, —CH$_2$OCH$_3$, aryl or heteroaryl; or
$R^4$ and $R^5$ are each independently —H, $C_1$-$C_3$ alkyl or aralkyl; and
$R^6$ is —H or halo.

In a third aspect of the present invention, there is provided a compound of Formula (I''):

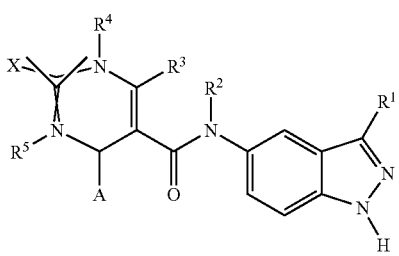

(I'')

or a salt, solvate, or physiologically functional derivative thereof:

wherein:
⁓ indicates a single or double bond;
X is =O, =S, $C_1$-$C_3$alkyl, or —N(H)R;
A is aryl, aralkyl, heteroaryl, $C_1$-$C_6$ alkyl, $C_3$-$C_7$ cycloalkyl, $C_2$-$C_6$ alkenyl, or $C_2$-$C_6$ alkynyl;
R is $C_1$-$C_3$alkyl, aryl, heteroaryl, —C(O)R'', —S(O)$_2$R'', or —C(O)NR'';
$R^1$ is —H, halo, $C_1$-$C_6$alkyl, aryl, heteroaryl, or N(H)R'';
$R^1$ is —H, $C_1$-$C_3$alkyl, aryl, —C(O)R'', —S(O)$_2$R'', or —C(O)N(H)R'';
R'' is $C_1$-$C_3$ alkyl;
$R^2$ is —H or $C_1$-$C_3$ alkyl;
$R^3$ is —H, $C_1$-$C_3$ alkyl, aryl or heteroaryl; and
$R^4$ and $R^5$ are each independently —H, $C_1$-$C_3$ alkyl or aralkyl.

In a fourth aspect of the present invention, there is provided a compound of Formula (I'''):

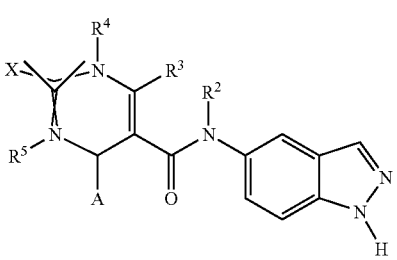

(I''')

or a salt, solvate, or physiologically functional derivative thereof:

wherein:
⁓ indicates a single or double bond;
X is =O, =S, $C_1$-$C_3$ alkyl, or —N(H)R;

A is aryl, aralkyl, heteroaryl, $C_1$-$C_6$ alkyl, $C_3$-$C_7$ cycloalkyl, $C_2$-$C_6$ alkenyl, or $C_2$-$C_6$ alkynyl;

R is $C_1$-$C_3$ alkyl, aryl, heteroaryl, —C(O)R", —S(O)$_2$R", or —C(O)NR";

R' is —H, $C_1$-$C_3$alkyl, aryl, —C(O)R", —S(O)2R", or —C(O)N(H)R";

R" is $C_1$-$C_3$ alkyl;

$R^2$ is —H or $C_1$-$C_3$ alkyl;

$R^3$ is —H, $C_1$-$C_3$ alkyl, aryl or heteroaryl; and $R^4$ and $R^5$ are each independently —H, $C_1$-$C_3$ alkyl or aralkyl.

In a fifth aspect of the present invention, there is provided a compound of Formula (I):

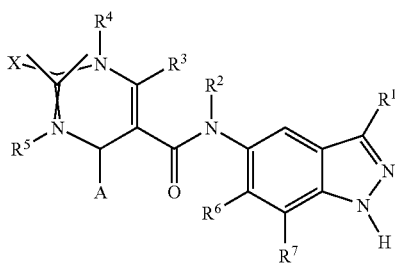

(I)

or a salt, solvate, or physiologically functional derivative thereof:

wherein:

⚹ indicates a single or double bond;

X is =O, =S, $C_1$-$C_3$alkyl, or —N(H)R;

A is aryl, aralkyl, heteroaryl, $C_1$-$C_6$ alkyl, $C_3$-$C_7$ cycloalkyl, $C_2$-$C_6$ alkenyl, or $C_2$-$C_6$ alkynyl;

R is $C_1$-$C_3$ alkyl, aryl, heteroaryl, —C(O)R", —S(O)$_2$R", or —C(O)NR";

$R^1$ is —H, halo, or $C_1$-$C_6$ alkyl;

R' is —H, $C_1$-$C_3$alkyl, aryl, —C(O)R", —S(O)$_2$R", or —C(O)N(H)R";

R" is $C_1$-$C_3$ alkyl;

$R^2$ is —H or $C_1$-$C_3$ alkyl, $R^3$ is —H, $C_1$-$C_3$ alkyl, aryl or heteroaryl; or $R^2$ and $R^3$ together with the ring and atoms to which they are attached form a fused ring system;

$R^4$ and $R^5$ are each independently —H, $C_1$-$C_3$ alkyl or aralkyl;

$R^6$ is —H or halo; and $R^7$ is —H, $C_1$-$C_3$alkyl, or halo.

In a sixth aspect of the present invention, there is provided a compound of Formula (I):

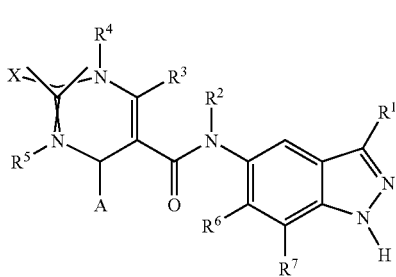

(I)

or a salt, solvate, or physiologically functional derivative thereof:

wherein:

⚹ indicates a single or double bond;

X is =O, =S, $C_1$-$C_3$ alkyl, or —N(H)R;

A is aryl, aralkyl, heteroaryl, $C_1$-$C_6$ alkyl, —CH$_2$OCH$_2$R'", $C_3$-$C_7$ cycloalkyl, $C_1$-$C_6$ alkenyl, or $C_1$-$C_6$ alkynyl;

R is $C_1$-$C_3$ alkyl, aryl, heteroaryl, —C(O)R", —S(O)$_2$R", or —C(O)NR";

$R^1$ is aryl, heteroaryl, or N(H)R';

R' is —H, $C_1$-$C_3$alkyl, aryl, —C(O)R", —S(O)$_2$R", or —C(O)N(H)R";

R" is $C_1$-$C_3$alkyl;

R'" is phenyl;

$R^2$ is —H or $C_1$-$C_3$ alkyl, $R^3$ is —H, $C_1$-$C_3$ alkyl, aryl or heteroaryl; or $R^2$ and $R^3$ together with the ring and atoms to which they are attached form a fused ring system;

$R^4$ and $R^5$ are each independently —H, $C_1$-$C_3$ alkyl or aralkyl;

$R^6$ is —H or halo; and $R^7$ is —H, $C_1$-$C_3$ alkyl, or halo.

In a seventh aspect of the present invention, there is provided a pharmaceutical composition comprising a therapeutically effective amount of a compound of formula (I) or a salt, solvate, or a physiologically functional derivative thereof and one or more of pharmaceutically acceptable carriers, diluents and excipients.

In an eighth aspect of the present invention, there is provided a method of treating a disorder in a mammal, said disorder being mediated by inappropriate ROCK-1 activity, comprising: administering to said mammal a therapeutically effective amount of a compound of formula (I) or a salt, solvate or a physiologically functional derivative thereof.

In a ninth aspect of the present invention, there is provided a compound of formula (I), or a salt, solvate, or a physiologically functional derivative thereof for use in therapy.

In a tenth aspect of the present invention, there is provided the use of a compound of formula (I), or a salt, solvate, or a physiologically functional derivative thereof in the preparation of a medicament for use in the treatment of a disorder mediated by inappropriate ROCK-1 activity.

In an eleventh aspect of the present invention, there is provided a method of treating a disorder in a mammal, said disorder being mediated by inappropriate Aurora kinase activity, comprising: administering to said mammal a therapeutically effective amount of a compound of formula (I) or a salt, solvate or a physiologically functional derivative thereof.

In a twelfth aspect of the present invention, there is provided the use of a compound of formula (I), or a salt, solvate, or a physiologically functional derivative thereof in the preparation of a medicament for use in the treatment of a disorder mediated by inappropriate Aurora kinase activity.

DETAILED DESCRIPTION OF THE INVENTION

As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease In the rate of advancement of a disease or disorder. The term also includes within its scope amounts effective to enhance normal physiological function.

As used herein the term "alkyl" refers to a straight- or branched-chain hydrocarbon radical having from one to twelve carbon atoms, optionally substituted with substituents selected from the group consisting of unsubstituted $C_1$-$C_6$ alkyl, $C_1$-$C_6$ hydroxyalkyl, $C_1$-$C_6$ alkoxy, $C_1$-$C_6$ alkylsulfanyl, $C_1$-$C_6$ alkylsulfenyl, $C_1$-$C_6$ alkylsulfonyl, oxo, hydroxy, mercapto, amino optionally substituted by alkyl, carboxy, carbamoyl optionally substituted by alkyl, aryl, aryloxy, heteroaryl, heterocyclyl, aminosulfonyl optionally substituted by alkyl, nitro, cyano, halo, or $C_1$-$C_6$ perfluoroalkyl, multiple degrees of substitution being allowed. Examples of "alkyl" as used herein include, but are not limited to, methyl, ethyl, n-propyl, isopropyl, n-butyl, isobutyl, t-butyl, n-pentyl, isopentyl, and the like.

As used herein, the terms "$C_1$-$C_3$ alkyl" and "$C_1$-$C_6$ alkyl" refer to an alkyl group, as defined above, containing at least 1, and at most 3 or 6 carbon atoms respectively. Examples of such branched or straight-chained alkyl groups useful in the present invention include, but are not limited to, methyl, ethyl, n-propyl, isopropyl, isobutyl, n-butyl, t-butyl, n-pentyl, isopentyl, and n-hexyl.

As used herein, the term "alkylene" refers to a straight or branched chain divalent hydrocarbon radical having from one to ten carbon atoms, optionally substituted with substituents selected from the group which includes $C_1$-$C_6$ alkyl, $C_1$-$C_6$ alkoxy, $C_1$-$C_6$ alkylsulfanyl, $C_1$-$C_{10}$ alkylsulfenyl, $C_1$-$C_6$ alkylsulfonyl, oxo, hydroxy, mercapto, amino optionally substituted by alkyl, carboxy, carbamoyl optionally substituted by alkyl, aryl, heteroaryl, heterocyclyl, aminosulfonyl optionally substituted by alkyl, nitro, cyano, halo, and $C_1$-$C_6$ perfluoroalkyl, multiple degrees of substitution being allowed. Examples of "alkylene" as used herein include, but are not limited to, methylene, ethylene, n-propylene, n-butylene, and the like.

As used herein, the term "$C_1$-$C_3$ alkylene" refers to an alkylene group, as defined above, which contains at least 1, and at most 3 or 6, carbon atoms respectively. Examples of "$C_1$-$C_6$ alkylene" and "$C_1$-$C_6$ alkylene" groups useful in the present invention include, but are not limited to, methylene, ethylene, n-propylene, n-butylene, isopentylene, and the like.

As used herein, the term "alkenyl" refers to a hydrocarbon radical having from two to ten carbons and at least one carbon-carbon double bond, optionally substituted with substituents selected from the group which includes $C_1$-$C_6$ alkyl, $C_1$-$C_6$ alkoxy, $C_1$-$C_6$ alkylsulfanyl, $C_1$-$C_6$ alkylsulfenyl, $C_1$-$C_6$ alkylsulfonyl, aryl, oxo, hydroxy, mercapto, amino optionally substituted by alkyl, carboxy, carbamoyl optionally substituted by alkyl, aminosulfonyl optionally substituted by alkyl, nitro, cyano, halogen and $C_1$-$C_6$ perfluoroalkyl, multiple degrees of substitution being allowed. Examples of "alkenyl" as used herein Include, ethenyl, propenyl, 1-butenyl, 2-butenyl, and isobutenyl.

As used herein, the term "$C_2$-$C_6$ alkenyl" refers to an alkenyl group, as defined above, containing at least 2, and at most 6, carbon atoms. Examples "$C_1$-$C_6$ alkenyl" groups useful in the present invention include, but are not limited to, ethenyl, propenyl, 1-butenyl, 2-butenyl, and isobutenyl.

As used herein, the term "alkynyl" refers to a hydrocarbon radical having from two to ten carbons and at least one carbon-carbon triple bond, optionally substituted with substituents selected from the group which includes $C_1$-$C_6$ alkyl, $C_1$-$C_6$ alkoxy, $C_1$-$C_6$ alkylsulfanyl, $C_1$-$C_6$ alkylsulfenyl, $C_1$-$C_6$ alkylsulfonyl, oxo, aryl, hydroxy, mercapto, amino optionally substituted by alkyl, carboxy, carbamoyl optionally substituted by alkyl, aminosulfonyl optionally substituted by alkyl, nitro, cyano, halogen and $C_1$-$C_6$ perfluoroalkyl, multiple degrees of substitution being allowed. Examples of "alkynyl" as used herein, Include but are not limited to acetylenyl, 1-propynyl, 1-butynyl, 2-butynyl, 1-pentynyl, and 1-hexynyl.

As used herein, the term "$C_2$-$C_6$ alkynyl" refers to an alkynyl group, as defined above, containing at least 2, and at most 6, carbon atoms. Examples of "$C_1$-$C_6$ alkynyl" groups useful in the present invention include, but are not limited to, to acetylenyl, 1-propynyl, 1-butynyl, 2-butynyl, 1-pentynyl, and 1-hexynyl.

As used herein, the term "halogen" refers to fluorine (F), chlorine (Cl), bromine (Br), or iodine (I) and the term "halo" refers to the halogen radicals: fluoro (—F), chloro (—Cl), bromo(—Br), and iodo(—I).

As used herein, the term "$C_1$-$C_6$ haloalkyl" refers to an alkyl group as defined above containing at least 1, and at most 6 carbon atoms respectively substituted with at least one halo group, halo being as defined herein. Examples of such branched or straight chained haloalkyl groups useful in the present invention include, but are not limited to, methyl, ethyl, propyl, isopropyl, isobutyl and n-butyl substituted independently with one or more halos, e.g., fluoro, chloro, bromo and iodo.

As used herein, the term "cycloalkyl" refers to a non-aromatic cyclic hydrocarbon ring containing from 3 to 10 carbon atoms, said ring optionally containing one double bond and which optionally may further include includes a $C_1$-$C_3$ alkylene linker through which it may be attached. In a like manner the term "$C_3$-$C_7$ cycloalkyl" refers to a cycloalkyl groups as defined above having from three to seven carbon atoms. The $C_1$-$C_3$ alkylene group is as defined above. Exemplary "$C_3$-$C_7$ cycloalkyl" groups useful in the present invention include, but are not limited to, cyclopropyl, cyclobutyl, cyclopentyl, cyclohexyl, cycloheptyl, and cyclohexylene.

As used herein, the term "heterocyclic" or the term "heterocyclyl" refers to a three to twelve-membered non-aromatic heterocyclic ring, being saturated or having one or more degrees of unsaturation, containing one or more heteroatom substitutions selected from S, S(O), S(O)$_2$, O, or N, optionally substituted with substituents selected from the group consisting of $C_1$-$C_6$ alkyl, $C_1$-$C_6$ alkoxy, $C_1$-$C_6$ alkylsulfanyl, $C_1$-$C_6$ alkylsulfenyl, $C_1$-$C_6$ alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halo, aryl, aralkyl, heteroaryl, or $C_1$-$C_6$ perfluoroalkyl, multiple degrees of substitution being allowed. Such a ring may be optionally fused to one or more other "heterocyclic" ring(s) or cycloalkyl ring(s). Examples of "heterocyclic" moieties Include, but are not limited to, tetrahydrofuran, pyran, 1,4-dioxane, 1,3-dioxane, piperidine, piperazine, 2,4-piperazinedione, pyrrolidine, imidazolidine, pyrazolidine, morpholine, thiomorpholine, tetrahydrothiopyran, tetrahydrothiophene, and the like.

As used herein, the term "aryl" refers to an optionally substituted benzene ring or to an optionally substituted benzene ring system fused to one or more optionally substituted benzene, heterocyclyl, or heteroaryl rings to form, for example, anthracene, phenanthrene, napthalene, or benzodioxin ring systems. Exemplary optional substituents include $C_1$-$C_6$ alkyl, $C_1$-$C_6$ alkoxy, $C_1$-$C_6$ haloalkyl, $C_1$-$C_6$ haloalkoxy, $C_1$-$C_6$ alkylsulfanyl, $C_1$-$C_6$ alkylsulfenyl, $C_1$-$C_6$ alkylsulfonyl, $C_1$-$C_6$ alkylsulfonylamino, arylsulfonoamino, alkylcarboxy, alkylcarboxyamide, oxo, hydroxy, mercapto, amino optionally substituted by alkyl, aryl, or heteroaryl, carboxy, tetrazolyl, carboxamide, carbamoyl optionally substituted by alkyl, aryl, or heteroaryl, aminosulfonyl, acyl, aroyl, aroylamino, heteroaroyl, acyloxy, aroyloxy, heteroaroyloxy, alkoxycarbonyl, nitro, cyano, halo, heteroaryl, heterocyclyl, aryl, ureido, arylurea, alkylurea, cycloalkylurea, alkylthiourea, aryloxy, aralkoxy, —N(H)S(O)$_2$CH$_3$, or —O(CH$_2$)$_r$OH, where r is 1, 2, 3, or 4, multiple degrees of substitution being allowed. Examples of "aryl" groups include, but are not limited to, phenyl, 2-naphthyl, 1-naphthyl, biphenyl, 1,4-benzodioxin-6-yl as well as substituted derivatives thereof.

As used herein, the term "aralkyl" refers to an aryl or heteroaryl group, as defined herein, attached through a $C_1$-$C_3$ alkylene linker, wherein the $C_1$-$C_3$ alkylene is as defined herein. Examples of "aralkyl" include, but are not limited to, benzyl, phenylpropyl, 2-pyridylmethyl, 3-isoxazolylmethyl, 5-methyl-3-isoxazolylmethyl, and 2-imidazolyl ethyl.

As used herein, the term "heteroaryl" refers to a monocyclic five to seven membered aromatic ring, or to a fused bicyclic or tricyclic aromatic ring system comprising two of such monocyclic five to seven membered aromatic rings. These heteroaryl rings contain one or more nitrogen, sulfur, and/or oxygen heteroatoms, where N-oxides and sulfur oxides and dioxides are permissible heteroatom substitutions and may be optionally substituted with up to three members selected from a group consisting of $C_1$-$C_6$ alkyl, $C_1$-$C_6$ alkoxy, $C_1$-$C_6$ haloalkyl, $C_1$-$C_6$ haloalkoxy, $C_1$-$C_6$ alkylsulfanyl, $C_1$-$C_6$ alkylsulfenyl, $C_1$-$C_6$ alkylsulfonyl, $C_1$-$C_6$ alkylsulfonylamino, arylsulfonoamino, alkylcarboxy, alkylcarboxyamide, oxo, hydroxy, mercapto, amino optionally substituted by alkyl, aryl, or heteroaryl, carboxy, tetrazolyl, carboxamide, carbamoyl optionally substituted by alkyl, aryl, or heteroaryl, aminosulfonyl, acyl, aroyl, aroylamino, heteroaroyl, acyloxy, aroyloxy, heteroaroyloxy, alkoxycarbonyl, nitro, cyano, halo, heteroaryl, heterocyclyl, aryl, ureido, arylurea, alkylurea, cycloalkylurea, alkylthiourea, aryloxy, or aralkoxy, multiple degrees of substitution being allowed. Examples of "heteroaryl" groups used herein include furanyl, thiophenyl, pyrrolyl, imidazolyl, pyrazolyl, triazolyl, tetrazolyl, thiazolyl, thienyl, oxazolyl, isoxazolyl, oxadiazolyl, oxo-pyridyl, quinoxalinyl, thiadiazolyl, isothiazolyl, pyridyl, pyridazyl, pyrazinyl, pyrimidyl, quinazolinyl, quinolinyl, isoquinolinyl, benzofuranyl, benzothiophenyl, indolyl, indazolyl, and substituted versions thereof.

As used herein, the term "alkoxy" refers to the group R$_a$O—, where R$_a$ is alkyl as defined above and the terms "$C_1$-$C_3$ alkoxy" and "$C_1$-$C_6$ alkoxy" refer to an alkoxy group as defined herein wherein the alkyl moiety contains at least 1, and at most 3 or 6, carbon atoms. Exemplary "$C_1$-$C_3$ alkoxy" and "$C_1$-$C_6$ alkoxy" groups useful in the present invention include, but are not limited to, methoxy, ethoxy, n-propoxy, isopropoxy, n-butoxy, and t-butoxy.

As used herein, the term "amino" refers to the group —NH$_2$.

As used herein the term "alkylamino" refers to the group —NHR$_a$ wherein R$_a$ is alkyl as defined above.

As used herein the term "arylamino" refers to the group —NHR$_a$ wherein R$_a$ is aryl as defined above.

As used herein the term "aralkylamino" refers to the group —NHR$_a$ wherein R$_a$ is an aralkyl group as defined above.

As used herein the term "aralkoxy" refers to the group R$_b$R$_a$O—, where R$_a$ is alkylene and R$_b$ is aryl or heteroaryl all as defined above.

As used herein the term "aryloxy" refers to the group R$_a$O—, where R$_a$ is aryl or heteroaryl both as defined above.

As used herein the term "ureido" refers to the group —NHC(O)NH$_2$

As used herein, the term "arylurea" refers to the group —NHC(O)NHR$_a$R$_b$ wherein R$_a$ is aryl or heteroaryl and R$_b$ is —H, alkyl, or aryl as defined above.

As used herein, the term "arylthiourea" refers to the group —NHC(S)NHR$_a$ wherein R$_a$ is aryl as defined above.

As used herein, the term "alkylurea" refers to the group —NHC(O)NR$_a$R$_b$ wherein R$_a$ is alkyl and R$_b$ is —H or alkyl as defined above.

As used herein, the term "cycloalkylurea" refers to the group —NHC(O)NHR$_a$ wherein R$_a$ is cycloalkyl as defined above.

As used herein, the term "$C_3$-$C_7$ cycloalkoxy" refers to the group R$_a$O—, where R$_a$ is $C_3$-$C_7$ cycloalkyl as defined above. Exemplary $C_3$-$C_7$ cycloalkoxy groups useful in the present invention include, but are not limited to, cyclobutoxy, and cyclopentoxy.

As used herein, the term "haloalkoxy" refers to the group R$_a$O—, where R$_a$ is haloalkyl as defined above and the term "$C_1$-$C_6$ haloalkoxy" refers to a haloalkoxy group as defined herein wherein the haloalkyl moiety contains at least 1, and at most 6, carbon atoms. Exemplary $C_1$-$C_6$ haloalkoxy groups useful in the present invention include, but is not limited to, trifluoromethoxy.

As used herein, the term "alkylsulfanyl" refers to the group R$_a$S—, where R$_a$ is alkyl as defined above and the term "$C_1$-$C_6$ alkylsulfanyl" refers to an alkylsuffanyl group as defined herein wherein the alkyl moiety contains at least 1, and at most 6, carbon atoms.

As used herein, the term "haloalkylsulfanyl" refers to the group R$_a$S—, where R$_a$ is haloalkyl as defined above and the term "$C_1$-$C_6$ haloalkylsulfanyl" refers to a haloalkylsulfanyl group as defined herein wherein the alkyl moiety contains at least 1, and at most 6, carbon atoms.

As used herein, the term "alkylsulfenyl" refers to the group R$_a$S(O)—, where R$_a$ is alkyl as defined above and the term "$C_1$-$C_6$ alkylsulfenyl" refers to an alkylsulfenyl group as defined herein wherein the alkyl moiety contains at least 1, and at most 6, carbon atoms.

As used herein, the term "alkylsulfonyl" refers to the group R$_a$S(O)$_2$—, where R$_a$ is alkyl as defined above and the term "$C_1$-$C_6$ alkylsulfonyl" refers to an alkylsulfonyl group as defined herein wherein the alkyl moiety contains at least 1, and at most 6, carbon atoms.

As used herein, the term "alkylsulfonylamino" refers to the group —NR$_b$S(O)$_2$R$_a$ wherein R$_a$ is alkyl and R$_b$ is —H or $C_1$-$C_6$ alkyl as defined above, and the term "$C_1$-$C_6$ alkylsulfonylamino" refers to an alkylsulfonylamino group as defined herein wherein the alkyl moiety contains at least 1, and at most 6, carbon atoms.

As used herein, the term "arylsulfonylamino" refers to the group —NR$_b$S(O)$_2$R$_a$ wherein R$_a$ is aryl or heteroaryl and R$_b$ is —H or $C_1$-$C_6$ alkyl as defined above.

As used herein, the term "alkylcarboxyamide" refers to the group —NHC(O)R$_a$ wherein R$_a$ is alkyl, amino, or amino substituted with alkyl, aryl or heteroaryl as described above.

As used herein the term "alkylcarboxy" refers to the group —C(O)R$_a$ wherein R$_a$ is alkyl as described above.

As used herein, the term "oxo" refers to the group =O.

As used herein, the term "mercapto" refers to the group —SH.

As used herein, the term "carboxy" refers to the group —C(O)OR$_a$, wherein R$_a$ is H or alkyl as defined herein.

As used herein, the term "cyano" refers to the group —CN.

As used herein the term "cyanoalkyl" refers to the group —R$_a$CN wherein R$_a$ is alkyl as defined above. Exemplary "cyanoalkyl" groups useful in the present invention include, but are not limited to, cyanomethyl, cyanoethyl, and cyanoisopropyl.

As used herein, the term "nitro" refers to the group —$NO_2$.

As used herein, the term "aminosulfonyl" refers to the group —$S(O)_2NR_aR_b$ wherein $R_a$ and $R_b$ are independently H, $C_1$-$C_6$alkyl, aryl, aralkyl, or heteroaryl.

As used herein, the term "carbamoyl" refers to the group —OC(O)NHR$_a$ where R$_a$ is hydrogen or alkyl as defined herein.

As used herein, the term "carboxamide" refers to the group —$C(O)NR_aR_b$ wherein $R_a$ and $R_b$ are independently H, $C_1$-$C_6$alkyl, aryl, aralkyl, or heteroaryl.

As used herein, the term "sulfanyl" shall refer to the group —S—.

As used herein, the term "sulfenyl" shall refer to the group —S(O)—.

As used herein, the term "sulfonyl" shall refer to the group —$S(O)_2$— or —$SO_2$—.

As used herein, the term "acyl" refers to the group $R_aC(O)$—, where $R_a$ is alkyl, cycloalkyl, or heterocyclyl as defined herein.

As used herein, the term "aroyl" refers to the group $R_aC(O)$—, where $R_a$ is aryl as defined herein.

As used herein, the term "aroylamino" refers to the group $R_aC(O)NH$—, where $R_a$ is aryl as defined herein.

As used herein, the term "heteroaroyl" refers to the group $R_aC(O)$—, where $R_a$ is heteroaryl as defined herein.

As used herein, the term "alkoxycarbonyl" refers to the group $R_aOC(O)$—, where $R_a$ is alkyl as defined herein.

As used herein, the term "acyloxy" refers to the group $R_aC(O)O$—, where $R_a$ is alkyl, cycloalkyl, or heterocyclyl as defined herein.

As used herein, the term "aroyloxy" refers to the group $R_aC(O)O$—, where $R_a$ is aryl as defined herein.

As used herein, the term "heteroaroyloxy" refers to the group $R_aC(O)O$—, where $R_a$ is heteroaryl as defined herein.

As used herein, the term "optionally" means that the subsequently described event(s) may or may not occur, and includes both event(s), which occur, and events that do not occur.

As used herein, the term "physiologically functional derivative" refers to any pharmaceutically acceptable derivative of a compound of the present invention, for example, an ester or an amide, which upon administration to a mammal is capable of providing (directly or indirectly) a compound of the present invention or an active metabolite thereof. Such derivatives are clear to those skilled In the art, without undue experimentation, and with reference to the teaching of Burger's Medicinal Chemistry And Drug Discovery, 5$^{th}$ Edition, Vol 1: Principles and Practice, which is incorporated herein by reference to the extent that it teaches physiologically functional derivatives.

As used herein, the term "solvate" refers to a complex of variable stoichiometry formed by a solute (in this invention, a compound of formula (I) or a salt or physiologically functional derivative thereof) and a solvent. Such solvents for the purpose of the invention may not interfere with the biological activity of the solute. Examples of suitable solvents include, but are not limited to, water, methanol, ethanol and acetic acid. Preferably the solvent used is a pharmaceutically acceptable solvent. Examples of suitable pharmaceutically acceptable solvents include, without limitation, water, ethanol and acetic acid. Most preferably the solvent used is water.

As used herein, the term "substituted" refers to substitution with the named substituent or substituents, multiple degrees of substitution being allowed unless otherwise stated.

Certain of the compounds described herein may contain one or more chiral atoms, or may otherwise be capable of existing as two enantiomers. The compounds of this invention include mixtures of enantiomers as well as purified enantiomers or enantiomerically enriched mixtures. Also included within the scope of the invention are the individual Isomers of the compounds represented by formula (I) above as well as any wholly or partially equilibrated mixtures thereof. The present invention also covers the individual isomers of the compounds represented by the formulas above as mixtures with isomers thereof in which one or more chiral centers are inverted. Also, it is understood that any tautomers and mixtures of tautomers of the compounds of formula (I) are included within the scope of the compounds of formula (I).

It is to be understood that reference to compounds of formula (I), (I'), (I"), or (I'") above, following herein, refers to compounds within the scope of formula (I), (I"), (I"), and (I'") as defined above with respect to $R^1$, $R^2$, $R^3$, $R^4$, $R^5$, $R^6$, $R^7$, R', R", R'", $R^a$, X, and A unless specifically limited otherwise.

In one embodiment, X is =O. In another embodiment, X is =S. In an alternative embodiment, X is $C_1$-$C_3$ alkyl, preferably —$CH_3$. In another embodiment, X is —N(H)R, where R is as defined above, preferably X is —N(H)R, where R is —H.

It is understood that the bonds of Formula (I), represented by ✗, attached to the pyrimidine ring carbon, which is between the pyrimidine nitrogens and attached to X (see arrow in formula following)

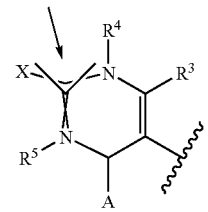

represent either single or double bonds. As is understood by those skilled In the art and specifically illustrated in the working examples following (for instance see Examples 1, 50, and 51) such bonds will independently be a single or double bond depending on which substituent of X is chosen.

It is also understood that substituent bonding locations having an unfilled valence are indicated by ⸳⸳⸳. The appropriate attachments are further illustrated in the working examples recited below.

In one embodiment, A is aryl. In another embodiment, A is selected from

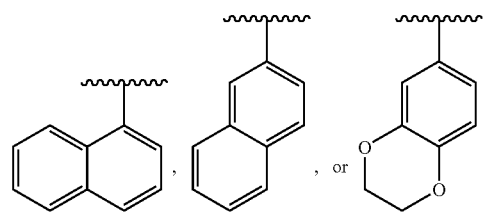

.

In one embodiment, A is selected from

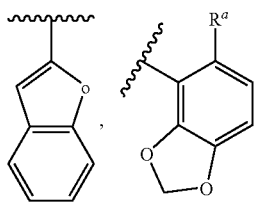

where $R^a$ is —H or —OCH$_3$,

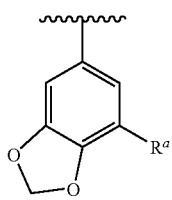

where $R^a$ is —Cl,

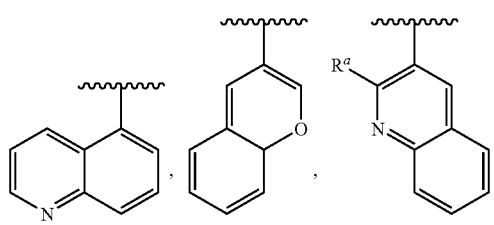

where $R^a$ is —H or —Cl, or

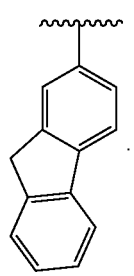

In another embodiment, A is

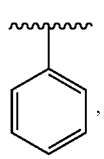

optionally substituted with one or more groups selected from halo, preferably —F or —Cl; C$_1$-C$_6$ alkoxy, preferably methoxy or ethoxy; —S(O)$_2$R$^a$, where R$^a$ is C$_1$-C$_3$ alkyl, preferably —CH$_3$; —N(H)S(O)$_2$R$^a$, where R$^a$ is C$_1$-C$_3$ alkyl, preferably —CH$_3$; —S(O)$_2$NH$_2$; —C(O)NH$_2$; —C(O)OH; —CN; —OH; —O(CH$_2$)$_r$OH, where r is 1, 2, 3, or 4; heteroaryl, preferably

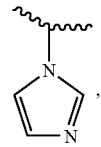

or —N(H)C(O)R$^a$, where R$_a$ is C$_1$-C$_3$ alkyl, preferably —CH$_3$; C$_1$-C$_6$ halolkyl, preferably —CF$_3$.

In one embodiment, A is

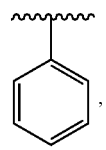

optionally substituted with one or more groups selected from halo, preferably —Br or —F; —NO$_2$; aryloxy, preferably phenoxy; aralkoxy, preferably benzyloxy; C$_1$-C$_6$ haloalkyl, preferably —CF$_3$; C$_1$-C$_6$ haloalkoxy, preferably —OCF$_3$; —NR$^a$R$^a$ where R$^a$ is independently —H, —CH$_3$ or —CH$_2$CH$_3$.

In one embodiment, A is

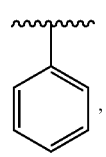

substituted with phenyl said phenyl being optionally substituted with one or more groups selected from halo, preferably —Cl or —F; C$_1$-C$_6$ haloalkyl, preferably —CF$_3$; C$_1$-C$_6$ alkoxy, preferably methoxy; —NR$^a$R$^a$ where R$^a$ is independently-H, —CH$_3$ or —CH$_2$CH$_3$; or —C(O)CH$_3$.

In one embodiment, A is

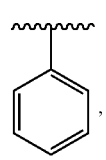

optionally substituted with a group selected from

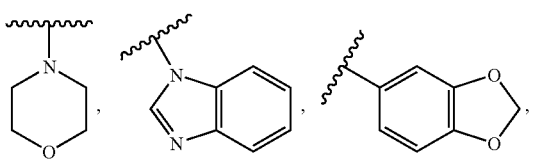

-continued

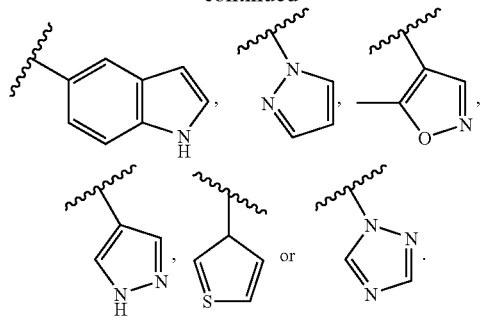

In one embodiment, A is heteroaryl. In another embodiment, A is selected from

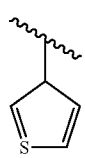

optionally substituted with halo, preferably —Br;

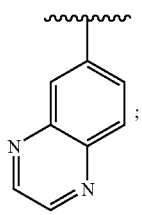

or

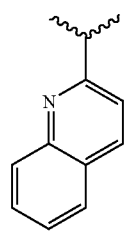

optionally substituted with —OH.

In another embodiment, A is

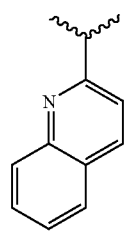

optionally substituted with

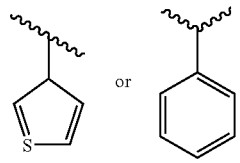

which phenyl group may be optionally substituted with one or more groups selected from halo, preferably —Cl; $C_1$-$C_6$ haloalkyl, preferably —$CF_3$; or $C_1$-$C_6$ alkoxy, preferably methoxy.

In another embodiment, A is

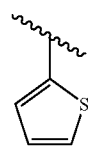

optionally substituted with $C_1$-$C_3$ alkyl, preferably —$CH_3$; aryl, preferably phenyl; halo, preferably —Cl; heteroaryl preferably

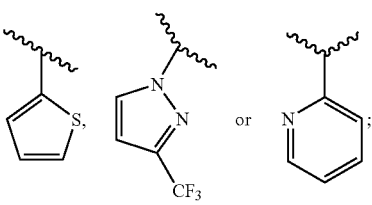

or $C_2$-$C_6$ alkynyl, preferably ethynyl substituted with phenyl.

In another embodiment, A is

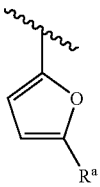

where $R^a$ is $C_1$-$C_3$ alkyl, preferably —CH; or aryl, preferably phenyl substituted with —Cl.

In another embodiment, A is

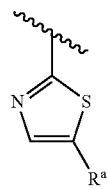

where $R^a$ is aryl, preferably phenyl; or —$SCH_3$.

In another embodiment, A is or

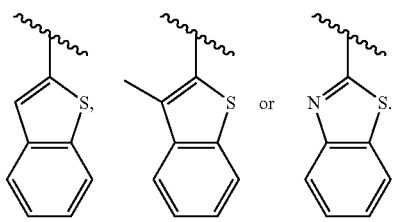

In an alternative embodiment, A is $C_1$-$C_6$ alkyl. In another embodiment A is $C_1$-$C_6$ alkyl optionally substituted with aryl, preferably

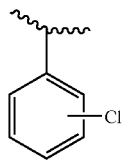

In one embodiment, A is $C_3$-$C_7$ cycloalkyl, preferably cyclohexenylene.

In an alternative embodiment, A is $C_2$-$C_6$ alkenyl. In another embodiment A is $C_2$-$C_6$ alkenyl optionally substituted with aryl, preferably phenyl or phenyl substituted with —$NO_2$ or methoxy. In another embodiment A is $C_2$-$C_6$ alkenyl optionally independently di-substituted with aryl, preferably phenyl and/or halo, preferably —Cl. In an alternative embodiment, A is $C_1$-$C_6$ alkenyl optionally substituted with heteroaryl, preferably furanyl.

In one embodiment, A is $C_2$-$C_6$ alkynyl optionally substituted with aryl, preferably phenyl.

In one embodiment, A is $C_2$-$C_6$ alkenyl or $C_2$-$C_6$ alkynyl. In another embodiment, A is —CN, —COOH, or —C(O)$NR^4R^5$. In a further embodiment, A is —NRR', —$NS(O)_2R$, —NC(O)R, or —N(R')C(O)$NR^4R^5$. Wherein R, R', $R^4$ and $R^5$ are as defined above.

In one embodiment, A is —$CH_2OCH_2R'''$, where R''' is aryl, preferably phenyl.

In one embodiment, $R^1$ is —H or —N(H)R', where R' is as defined above. In one embodiment, $R^1$ is —H. In another embodiment, $R^1$ is —N(H)R', where R' is —H. In another embodiment, $R^1$ is —N(H)R', where R' is phenyl optionally substituted with one or more halo, preferably —F.

In one embodiment, $R^1$ is halo, preferably, —Cl or —Br. In another embodiment, $R^1$ is $C_1$-$C_6$ alkyl, preferably —$CH_3$. In one embodiment, $R^1$ is aryl, preferably, phenyl optionally substituted with halo, preferably —F.

In one embodiment, $R^2$ is —H or $C_1$-$C_3$ alkyl. In one embodiment, $R^2$ is —H. In another embodiment, $R^1$ is $C_1$-$C_3$ alkyl, preferably methyl.

In one embodiment, $R^3$ is —H, $C_1$-$C_3$ alkyl, or heteroaryl. In one embodiment, $R^3$ is $C_1$-$C_3$ alkyl. In another embodiment, $R^3$ is —$CH_3$ or —$CH(CH_3)_2$. In one embodiment, $R^3$ is —$CH_3$. In another embodiment, $R^3$ is —H. In one embodiment, $R^3$ is heteroaryl, preferably furanyl. In another embodiment, $R^3$ is —$CH_2OCH_3$. In one embodiment, $R^2$ and $R^3$ together with the ring and atoms to which they are attached form a fused ring system;

As recited above $R^4$ and $R^5$ are each independently —H, $C_1$-$C_3$ alkyl or aralkyl.

In one embodiment $R^4$ is —H. In another embodiment, $R^4$ is $C_1$-$C_3$ alkyl, preferably —$CH_3$ or —$CH_2CH_3$. In another embodiment, $R^4$ is aralkyl, preferably benzyl.

In one embodiment $R^5$ is —H. In another embodiment, $R^5$ is $C_1$-$C_3$ alkyl, preferably —$CH_3$.

In one embodiment, $R^6$ is —H. In another embodiment, $R^6$ is halo, preferably —Cl or —F.

In one embodiment, $R^7$ is —H. In another embodiment, $R^7$ is halo, preferably —Cl.

Specific examples of compounds of the present invention include the following:

4-(4-fluorophenyl)-N-1H-indazol-5-yl-6-methyl-2-oxo-1,2,3,4-tetrahydro-5-pyrimidinecarboxamide;

4-[3,4-bis(ethyloxy)phenyl]-N-1H-indazol-5-yl-6-methyl-2-oxo-1,2,3,4-tetrahydro-5-pyrimidinecarboxamide;

N-1H-indazol-5-yl-6-methyl-4-[4-(methylsulfonyl)phenyl]-2-oxo-1,2,3,4-tetrahydro-5-pyrimidinecarboxamide;

N-1H-indazol-5-yl-6-methyl-2-oxo-4-(3-thienyl)-1,2,3,4-tetrahydro-5-pyrimidinecarboxamide;

N-1H-indazol-5-yl-4,6-dimethyl-2-oxo-1,2,3,4-tetrahydro-5-pyrimidinecarboxamide;

N-1H-indazol-5-yl-6-methyl-4-(1-naphthalenyl)-2-oxo-1,2,3,4-tetrahydro-5-pyrimidinecarboxamide;

N-1H-indazol-5-yl-6-methyl-4-(2-naphthalenyl)-2-oxo-1,2,3,4-tetrahydro-5-pyrimidinecarboxamide;

4-{5-[(1H-indazol-5-ylamino)carbonyl]-6-methyl-2-oxo-1,2,3,4-tetrahydro-4-pyrimidinyl}benzoic acid;

4-(2,4-difluorophenyl)-N-1H-indazol-5-yl-6-methyl-2-oxo-1,2,3,4-tetrahydro-5-pyrimidinecarboxamide;

N-1H-indazol-5-yl-6-methyl-4-[3-(methyloxy)phenyl]-2-oxo-1,2,3,4-tetrahydro-5-pyrimidinecarboxamide;

N-1H-indazol-5-yl-6-methyl-4-[2-(methyloxy)phenyl]-2-oxo-1,2,3,4-tetrahydro-5-pyrimidinecarboxamide;

4-(4-cyanophenyl)-N-1H-indazol-5-yl-6-methyl-2-oxo-1,2,3,4-tetrahydro-5-pyrimidinecarboxamide;

3-{5-[(1H-indazol-5-ylamino)carbonyl]-6-methyl-2-oxo-1,2,3,4-tetrahydro-4-pyrimidinyl}benzoic acid;

4-(2-fluorophenyl)-N-1H-indazol-5-yl-6-methyl-2-oxo-1,2,3,4-tetrahydro-5-pyrimidinecarboxamide;

4-(3-chloro-4-fluorophenyl)-N-1H-indazol-5-yl-6-methyl-2-oxo-1,2,3,4-tetrahydro-5-pyrimidinecarboxamide;

4-{3-[(2-hydroxyethyl)oxy]phenyl}-N-1H-indazol-5-yl-6-methyl-2-oxo-1,2,3,4-tetrahydro-5-pyrimidinecarboxamide 4-(4-bromo-2-thienyl)-N-1H-indazol-5-yl-6-methyl-2-oxo-1,2,3,4-tetrahydro-5-pyrimidinecarboxamide;

4-(4-hydroxyphenyl)-N-1H-indazol-5-yl-6-methyl-2-oxo-1,2,3,4-tetrahydro-5-pyrimidinecarboxamide;

4-(4-chloro-2-fluorophenyl)-N-1H-indazol-5-yl-6-methyl-2-oxo-1,2,3,4-tetrahydro-5-pyrimidinecarboxamide;

N-1H-indazol-5-yl-6-methyl-4-{3-[(methylsulfonyl)amino]phenyl}-2-oxo-1,2,3,4-tetrahydro-5-pyrimidinecarboxamide;

N-1H-indazol-5-yl-6-methyl-2-oxo-4-(6-quinoxalinyl)-1,2,3,4-tetrahydro-5-pyrimidinecarboxamide 4-[4-(aminosulfonyl)phenyl]-N-1H-indazol-5-yl-6-methyl-2-oxo-1,2,3,4-tetrahydro-5-pyrimidinecarboxamide;

N-1H-indazol-5-yl-6-methyl-2-oxo-4-(2-quinolinyl)-1,2,3,4-tetrahydro-5-pyrimidinecarboxamide;

4-[3-fluoro-4-(methyloxy)phenyl]-N-1H-indazol-5-yl-6-methyl-2-oxo-1,2,3,4-tetrahydro-5-pyrimidinecarboxamide;

4-(3-cyanophenyl)-N-1H-indazol-5-yl-6-methyl-2-oxo-1,2,3,4-tetrahydro-5-pyrimidinecarboxamide;

4-(1H-imidazol-1-yl)-N-1H-indazol-5-yl-6-methyl-2-oxo-1,2,3,4-tetrahydro-5-pyrimidinecarboxamide;

N-1H-indazol-5-yl-6-methyl-2-oxo-4-(3-quinolinyl)-1,2,3,4-tetrahydro-5-pyrimidinecarboxamide;
N-1H-indazol-5-yl-6-methyl-2-oxo-4-[(E)-2-phenylethenyl]-1,2,3,4-tetrahydro-5-pyrimidinecarboxamide;
N-1H-indazol-5-yl-6-methyl-2-oxo-4-[4-(trifluoromethyl)phenyl]-1,2,3,4-tetrahydro-5-pyrimidinecarboxamide;
4-(4-chlorophenyl)-N-1H-indazol-5-yl-6-methyl-2-oxo-1,2,3,4-tetrahydro-5-pyrimidinecarboxamide;
4-[4-(acetylamino)phenyl]-N-1H-indazol-5-yl-6-methyl-2-oxo-1,2,3,4-tetrahydro-5-pyrimidinecarboxamide;
4-(2-chlorophenyl)-N-1H-indazol-5-yl-6-methyl-2-oxo-1,2,3,4-tetrahydro-5-pyrimidinecarboxamide;
4-(2,3-dihydro-1,4-benzodioxin-6-yl)-N-1H-indazol-5-yl-6-methyl-2-oxo-1,2,3,4-tetrahydro-5-pyrimidinecarboxamide;
4-(3-hydroxyphenyl)-N-1H-indazol-5-yl-6-methyl-2-oxo-1,2,3,4-tetrahydro-5-pyrimidinecarboxamide;
4-(8-hydroxy-2-quinolinyl)-N-1H-indazol-5-yl-6-methyl-2-oxo-1,2,3,4-tetrahydro-5-pyrimidinecarboxamide;
4-[3,4-bis(methyloxy)phenyl]-N-1H-indazol-5-yl-6-methyl-2-oxo-1,2,3,4-tetrahydro-5-pyrimidinecarboxamide;
4-[2-(4-chlorophenyl)ethyl]-N-1H-indazol-5-yl-6-methyl-2-oxo-1,2,3,4-tetrahydro-5-pyrimidinecarboxamide;
4-[3-(1H-imidazol-1-yl)phenyl]-N-1H-indazol-5-yl-6-methyl-2-oxo-1,2,3,4-tetrahydro-5-pyrimidinecarboxamide;
4-(3-chlorophenyl)-N-1H-indazol-5-yl-6-methyl-2-oxo-1,2,3,4-tetrahydro-5-pyrimidinecarboxamide;
4-[4-(aminocarbonyl)phenyl]-N-1H-indazol-5-yl-6-methyl-2-oxo-1,2,3,4-tetrahydro-5-pyrimidinecarboxamide;
4-(4-fluorophenyl)-N-1H-indazol-5-yl-6-(1-methylethyl)-2-oxo-1,2,3,4-tetrahydro-5-pyrimidinecarboxamide;
4-(4-fluorophenyl)-6-(2-furanyl)-N-1H-indazol-5-yl-2-oxo-1,2,3,4-tetrahydro-5-pyrimidinecarboxamide;
4-(4-fluorophenyl)-N-1H-indazol-5-yl-1,6-dimethyl-2-oxo-1,2,3,4-tetrahydro-5-pyrimidinecarboxamide;
N-1H-indazol-5-yl-1,6-dimethyl-4-(2-naphthalenyl)-2-oxo-1,2,3,4-tetrahydro-5-pyrimidinecarboxamide;
N-1H-indazol-5-yl-6-methyl-4-(2-naphthalenyl)-2-thioxo-1,2,3,4-tetrahydro-5-pyrimidinecarboxamide;
4-(4-fluorophenyl)-N-1H-indazol-5-yl-6-methyl-2-thioxo-1,2,3,4-tetrahydro-5-pyrimidinecarboxamide;
N-1H-indazol-5-yl-6-methyl-4-(3-thienyl)-2-thioxo-1,2,3,4-tetrahydro-5-pyrimidinecarboxamide;
4-(4-fluorophenyl)-N-1H-indazol-5-yl-1,3,6-trimethyl-2-oxo-1,2,3,4-tetrahydro-5-pyrimidinecarboxamide;
4-(4-fluorophenyl)-N-1H-indazol-5-yl-6-methyl-2-oxo-1-(phenylmethyl)-1,2,3,4-tetrahydro-5-pyrimidinecarboxamide;
2-amino-4-(4-fluorophenyl)-N-1H-indazol-5-yl-6-methyl-1,4-dihydro-5-pyrimidinecarboxamide;
4-(4-fluorophenyl)-N-1H-indazol-5-yl-2,6-dimethyl-1,4-dihydro-5-pyrimidinecarboxamide;
4-(4-fluorophenyl)-N-1H-indazol-5-yl-N,6-dimethyl-2-oxo-1,2,3,4-tetrahydro-5-pyrimidinecarboxamide;
4-(4-fluorophenyl)-N-1H-indazol-5-yl-2-oxo-1,2,3,4-tetrahydro-5-pyrimidinecarboxamide;
1-ethyl-4-(4-fluorophenyl)-N-1H-indazol-5-yl-6-methyl-2-oxo-1,2,3,4-tetrahydro-5-pyrimidinecarboxamide; and
N-(3-amino-1H-indazol-5-yl)-(4-fluorophenyl)-6-methyl-2-oxo-1,2,3,4-tetrahydro-5-pyrimidinecarboxamide;

or a salt, solvate, or physiologically functional derivative thereof.

Further examples of compounds of the present invention include:
N-1H-indazol-5-yl-6-methyl-2-oxo-4-phenyl-1,2,3,4-tetrahydro-5-pyrimidinecarboxamide;
N-1H-indazol-5-yl-6-methyl-2-oxo-4-(4-pyridinyl)-1,2,3,4-tetrahydro-5-pyrimidinecarboxamide;
Methyl 3-{5-[(1H-indazol-5-ylamino)carbonyl]-6-methyl-2-oxo-1,2,3,4-tetrahydro-4-pyrimidinyl}benzoate;
Methyl 4-{5-[(1H-indazol-5-ylamino)carbonyl]-6-methyl-2-oxo-1,2,3,4-tetrahydro-4-pyrimidinyl}benzoate;
4-(3-furanyl)-N-1H-indazol-5-yl-6-methyl-2-oxo-1,2,3,4-tetrahydro-5-pyrimidinecarboxamide;
N-1H-indazol-5-yl-6-methyl-4-(2-methylpropyl)-2-oxo-1,2,3,4-tetrahydro-5-pyrimidinecarboxamide;
N-1H-indazol-5-yl-6-methyl-2-oxo-4-(2-phenylethyl)-1,2,3,4-tetrahydro-5-pyrimidinecarboxamide;
N-1H-indazol-5-yl-6-methyl-4-(4-nitrophenyl)-2-oxo-1,2,3,4-tetrahydro-5-pyrimidinecarboxamide;
4-(3-cyano-4-fluorophenyl)-N-1H-indazol-5-yl-6-methyl-2-oxo-1,2,3,4-tetrahydro-5-pyrimidinecarboxamide;
4-(4-fluoro-3-nitrophenyl)-N-1H-indazol-5-yl-6-methyl-2-oxo-1,2,3,4-tetrahydro-5-pyrimidinecarboxamide;
4-[2-hydroxy-4-(methyloxy)phenyl]-N-1H-indazol-5-yl-6-methyl-2-oxo-1,2,3,4-tetrahydro-5-pyrimidinecarboxamide; and
4-(4-biphenylyl)-N-1H-indazol-5-yl-6-methyl-2-oxo-1,2,3,4-tetrahydro-5-pyrimidinecarboxamide;

or a salt, solvate, or physiologically functional derivative thereof.

Further examples of compounds of the present invention include:
4-(1-benzofuran-2-yl)-N-1H-indazol-5-yl-6-methyl-2-oxo-1,2,3,4-tetrahydro-5-pyrimidinecarboxamide;
4-[(E)-2-(2-furanyl)ethenyl]-N-1H-indazol-5-yl-6-methyl-2-oxo-1,2,3,4-tetrahydro-5-pyrimidinecarboxamide;
N-1H-indazol-5-yl-6-methyl-4-(5-methyl-2-furanyl)-2-oxo-1,2,3,4-tetrahydro-5-pyrimidinecarboxamide;
4-[5-(4-chlorophenyl)-2-furanyl]-N-1H-indazol-5-yl-6-methyl-2-oxo-1,2,3,4-tetrahydro-5-pyrimidinecarboxamide;
4-(1,3-benzodioxol-5-yl)-N-1H-indazol-5-yl-6-methyl-2-oxo-1,2,3,4-tetrahydro-5-pyrimidinecarboxamide;
N-1H-indazol-5-yl-6-methyl-2-oxo-4-[4-(phenyloxy)phenyl]-1,2,3,4-tetrahydro-5-pyrimidinecarboxamide;
N-1H-indazol-5-yl-6-methyl-2-oxo-4-[3-(phenyloxy)phenyl]-1,2,3,4-tetrahydro-5-pyrimidinecarboxamide;
N-1H-indazol-5-yl-6-methyl-2-oxo-4-(5-quinolinyl)-1,2,3,4-tetrahydro-5-pyrimidinecarboxamide;
4-(3-Bromophenyl)-N-1H-indazol-5-yl-6-methyl-2-oxo-1,2,3,4-tetrahydro-5-pyrimidinecarboxamide;
N-1H-indazol-5-yl-6-methyl-2-oxo-4-(5-phenyl-2-thienyl)-1,2,3,4-tetrahydro-5-pyrimidinecarboxamide;
N-1H-indazol-5-yl-6-methyl-4-[(E)-2-(2-nitrophenyl)ethenyl]-2-oxo-1,2,3,4-tetrahydro-5-pyrimidinecarboxamide;
N-1H-indazol-5-yl-6-methyl-4-{(E)-2-[4-(methyloxy)phenyl]ethenyl}-2-oxo-1,2,3,4-tetrahydro-5-pyrimidinecarboxamide;
4-(1-cyclohexen-1-yl)-N-1H-indazol-5-yl-6-methyl-2-oxo-1,2,3,4-tetrahydro-5-pyrimidinecarboxamide;
N-1H-indazol-5-yl-6-methyl-4-{(E)-2-[2-(methyloxy)phenyl]ethenyl}-2-oxo-1,2,3,4-tetrahydro-5-pyrimidinecarboxamide;
4-(2,2-diphenylethenyl)-N-1H-indazol-5-yl-6-methyl-2-oxo-1,2,3,4-tetrahydro-5-pyrimidinecarboxamide;
4-[(Z)-1-chloro-2-phenylethenyl]-N-1H-indazol-5-yl-6-methyl-2-oxo-1,2,3,4-tetrahydro-5-pyrimidinecarboxamide;
N-1H-indazol-5-yl-6-methyl-2-oxo-4-{[(phenylmethyl)oxy]methyl}-1,2,3,4-tetrahydro-5-pyrimidinecarboxamide;
N-1H-Indazol-5-yl-6-methyl-2-oxo-4-(phenylethynyl)-1,2,3,4-tetrahydro-5-pyrimidinecarboxamide;

4-(2,2'-bithien-5-yl)-N-1H-indazol-5-yl-6-methyl-2-oxo-1,2,3,4-tetrahydro-5-pyrimidinecarboxamide;

N-1H-indazol-5-yl-6-methyl-4-(3-methyl-1-benzothien-2-yl)-2-oxo-1,2,3,4-tetrahydro-5-pyrimidinecarboxamide;

4-(5-chloro-2-thienyl)-N-1H-indazol-5-yl-6-methyl-2-oxo-1,2,3,4-tetrahydro-5-pyrimidinecarboxamide;

N-1H-indazol-5-yl-6-methyl-2-oxo-4-(1,3-thiazol-2-yl)-1,2,3,4-tetrahydro-5-pyrimidinecarboxamide;

N-1H-indazol-5-yl-6-methyl-4-(3-methyl-2-thienyl)-2-oxo-1,2,3,4-tetrahydro-5-pyrimidinecarboxamide;

4-(1-benzothien-2-yl)-N-1H-indazol-5-yl-6-methyl-2-oxo-1,2,3,4-tetrahydro-5-pyrimidinecarboxamide;

N-1H-indazol-5-yl-6-methyl-2-oxo-4-{3-[(phenylmethyl)oxy]phenyl}-1,2,3,4-tetrahydro-5-pyrimidinecarboxamide;

4-(9H-fluoren-2-yl)-N-1H-indazol-5-yl-6-methyl-2-oxo-1,2,3,4-tetrahydro-5-pyrimidinecarboxamide;

4-(3-bromo-4-fluorophenyl)-N-1H-indazol-5-yl-6-methyl-2-oxo-1,2,3,4-tetrahydro-5-pyrimidinecarboxamide;

N-1H-indazol-5-yl-6-methyl-4-[7-(methyloxy)-1,3-benzodioxol-5-yl]-2-oxo-1,2,3,4-tetrahydro-5-pyrimidinecarboxamide;

4-(1,3-benzodioxol-4-yl)-N-1H-indazol-5-yl-6-methyl-2-oxo-1,2,3,4-tetrahydro-5-pyrimidinecarboxamide;

N-1H-indazol-5-yl-6-methyl-2-oxo-4-{3-[(trifluoromethyl)oxy]phenyl}-1,2,3,4-tetrahydro-5-pyrimidinecarboxamide;

N-1H-indazol-5-yl-6-methyl-2-oxo-4-[3-(trifluoromethyl)phenyl]-1,2,3,4-tetrahydro-5-pyrimidinecarboxamide;

4-[3-hydroxy-4-(methyloxy)phenyl]-N-1H-indazol-5-yl-6-methyl-2-oxo-1,2,3,4-tetrahydro-5-pyrimidinecarboxamide;

4-(5-chloro-1,3-benzodioxol-4-yl)-N-1H-indazol-5-yl-6-methyl-2-oxo-1,2,3,4-tetrahydro-5-pyrimidinecarboxamide;

N-1H-indazol-5-yl-6-methyl-2-oxo-4-[5-(2-pyridinyl)-2-thienyl]-1,2,3,4-tetrahydro-5-pyrimidinecarboxamide;

N-1H-indazol-5-yl-6-methyl-2-oxo-4-(2-phenyl-1,3-thiazol-4-yl)-1,2,3,4-tetrahydro-5-pyrimidinecarboxamide;

N-1H-indazol-5-yl-6-methyl-4-[5-(methylthio)-2-thienyl]-2-oxo-1,2,3,4-tetrahydro-5-pyrimidinecarboxamide;

4-(1,3-benzothiazol-2-yl)-N-1H-indazol-5-yl-6-methyl-2-oxo-1,2,3,4-tetrahydro-5-pyrimidinecarboxamide;

4-(2H-chromen-3-yl)-N-1H-indazol-5-yl-6-methyl-2-oxo-1,2,3,4-tetrahydro-5-pyrimidinecarboxamide;

N-1H-indazol-5-yl-6-methyl-2-oxo-4-[5-(phenylethynyl)-2-thienyl]-1,2,3,4-tetrahydro-5-pyrimidinecarboxamide;

N-1H-indazol-5-yl-6-methyl-2-oxo-4-[4-(phenylethynyl)-2-thienyl]-1,2,3,4-tetrahydro-5-pyrimidinecarboxamide;

N-1H-indazol-5-yl-6-methyl-4-(5-methyl-2-thienyl)-2-oxo-1,2,3,4-tetrahydro-5-pyrimidinecarboxamide;

N-1H-indazol-5-yl-6-methyl-4-{5-[1-methyl-5-(trifluoromethyl)-1H-pyrazol-3-yl]-2-thienyl}-2-oxo-1,2,3,4-tetrahydro-5-pyrimidinecarboxamide;

N-1H-indazol-5-yl-6-methyl-2-oxo-4-[4-(2-pyridinyl)phenyl]-1,2,3,4-tetrahydro-5-pyrimidinecarboxamide;

4-[4-(dimethylamino)phenyl]-N-1H-indazol-5-yl-6-methyl-2-oxo-1,2,3,4-tetrahydro-5-pyrimidinecarboxamide;

4-[4-(diethylamino)phenyl]-N-1H-indazol-5-yl-6-methyl-2-oxo-1,2,3,4-tetrahydro-5-pyrimidinecarboxamide;

4-(2-chloro-3-quinolinyl)-N-1H-indazol-5-yl-6-methyl-2-oxo-1,2,3,4-tetrahydro-5-pyrimidinecarboxamide;

N-1H-indazol-5-yl-6-methyl-4-(4-methyl-3,4-dihydro-2H-1,4-benzoxazin-7-yl)-2-oxo-1,2,3,4-tetrahydro-5-pyrimidinecarboxamide;

N-1H-indazol-5-yl-6-methyl-4-[4-(4-morpholinyl)phenyl]-2-oxo-1,2,3,4-tetrahydro-5-pyrimidinecarboxamide;

N-1H-indazol-5-yl-6-methyl-2-oxo-4-[4-(2-thienyl)phenyl]-1,2,3,4-tetrahydro-5-pyrimidinecarboxamide;

N-1H-indazol-5-yl-6-methyl-2-oxo-4-[4-(1H-pyrazol-1-yl)phenyl]-1,2,3,4-tetrahydro-5-pyrimidinecarboxamide;

N-1H-indazol-5-yl-6-methyl-2-oxo-4-[4-(1H-1,2,4-triazol-1-yl)phenyl]-1,2,3,4-tetrahydro-5-pyrimidinecarboxamide;

4-[2,3-difluoro-4-(trifluoromethyl)phenyl]-N-1H-indazol-5-yl-6-methyl-2-oxo-1,2,3,4-tetrahydro-5-pyrimidinecarboxamide;

4-[4-(1H-benzimidazol-1-yl)phenyl]-N-1H-indazol-5-yl-6-methyl-2-oxo-1,2,3,4-tetrahydro-5-pyrimidinecarboxamide;

4-(4-Fluorophenyl)-N-[3-(4-fluorophenyl)-1H-indazol-5-yl]-6-methyl-2-oxo-1,2,3,4-tetrahydro-5-pyrimidinecarboxamide;

N-(3-Chloro-1H-indazol-5-yl)-4-(4-fluorophenyl)-6-methyl-2-oxo-1,2,3,4-tetrahydro-5-pyrimidinecarboxamide;

N-(3-Chloro-1H-indazol-5-yl)-6-methyl-4-(2-naphthalenyl)-2-oxo-1,2,3,4-tetrahydro-5-pyrimidinecarboxamide;

1-ethyl-4-(4-fluorophenyl)-N-1H-indazol-5-yl-6-methyl-2-oxo-1,2,3,4-tetrahydro-5-pyrimidinecarboxamide;

4-(4-fluorophenyl)-N-1H-indazol-5-yl-2-oxo-6-propyl-1,2,3,4-tetrahydro-5-pyrimidinecarboxamide;

N-1H-indazol-5-yl-4-(2-naphthalenyl)-2-oxo-6-propyl-1,2,3,4-tetrahydro-5-pyrimidinecarboxamide;

14-(4-fluorophenyl)-N-1H-indazol-5-yl-6-[(methyloxy)methyl]-2-oxo-1,2,3,4-tetrahydro-5-pyrimidinecarboxamide;

4-(4-fluorophenyl)-6-(1H-indazol-5-yl)hexahydro-1H-pyrrolo[3,4-d]pyrimidine-2,5-dione;

N-1H-indazol-5-yl-6-methyl-4-(3-nitrophenyl)-2-oxo-1,2,3,4-tetrahydro-5-pyrimidinecarboxamide;

4-(4-chlorophenyl)-6-(1H-indazol-5-yl)-3,4,6,7-tetrahydro-1H-pyrrolo[3,4-d]pyrimidine-2,5-dione;

4-(3-aminophenyl)-N-1H-indazol-5-yl-6-methyl-2-oxo-1,2,3,4-tetrahydro-5-pyrimidinecarboxamide;

4-(3,5-Dibromophenyl)-N-1H-indazol-5-yl-6-methyl-2-oxo-1,2,3,4-tetrahydro-5-pyrimidinecarboxamide;

4-(3,4-Difluorophenyl)-N-1H-indazol-5-yl-6-methyl-2-oxo-1,2,3,4-tetrahydro-5-pyrimidinecarboxamide;

N-1H-Indazol-5-yl-6-methyl-4-[(E)-1-methyl-2-phenylethenyl]-2-oxo-1,2,3,4-tetrahydro-5-pyrimidinecarboxamide;

4-(4-Fluorophenyl)-N-1H-indazol-5-yl-3,6-dimethyl-2-oxo-1,2,3,4-tetrahydro-5-pyrimidinecarboxamide;

6-Ethyl-4-(4-fluorophenyl)-N-1H-indazol-5-yl-2-oxo-1,2,3,4-tetrahydro-5-pyrimidinecarboxamide;

N-(6-Chloro-1H-indazol-5-yl)-4-(4-fluorophenyl)-6-methyl-2-oxo-1,2,3,4-tetrahydro-5-pyrimidinecarboxamide;

N-(6-Chloro-1H-indazol-5-yl)-6-methyl-4-(2-naphthalenyl)-2-oxo-1,2,3,4-tetrahydro-5-pyrimidinecarboxamide;

N-(6-Fluoro-1H-indazol-5-yl)-4-(4-fluorophenyl)-6-methyl-2-oxo-1,2,3,4-tetrahydro-5-pyrimidinecarboxamide;

N-(7-Chloro-1H-indazol-5-yl)-4-(4-fluorophenyl)-6-methyl-2-oxo-1,2,3,4-tetrahydro-5-pyrimidinecarboxamide;

N-(7-Chloro-1H-indazol-5-yl)-6-methyl-4-(2-naphthalenyl)-2-oxo-1,2,3,4-tetrahydro-5-pyrimidinecarboxamide;

N-(3-bromo-1H-indazol-5-yl)-4-(4-fluorophenyl)-6-methyl-2-oxo-1,2,3,4-tetrahydro-5-pyrimidinecarboxamide;

N-(3-bromo-1H-indazol-5-yl)-4-(2-naphthyl)-6-methyl-2-oxo-1,2,3,4-tetrahydro-5-pyrimidinecarboxamide;

N-(3-bromo-1H-indazol-5-yl)-4-(3-thiophenyl)-6-methyl-2-oxo-1,2,3,4-tetrahydro-5-pyrimidinecarboxamide;

4-(4-Bromophenyl)-N-1H-indazol-5-yl-6-methyl-2-oxo-1,2,3,4-tetrahydro-5-pyrimidinecarboxamide;

4-(3'-Amino-4-biphenylyl)-N-1H-indazol-5-yl-6-methyl-2-oxo-1,2,3,4-tetrahydro-5-pyrimidinecarboxamide;
N-1H-Indazol-5-yl-6-methyl-2-oxo-4-[4-(2-thienyl)phenyl]-1,2,3,4-tetrahydro-5-pyrimidinecarboxamide;
4-(2',4'-Difluoro-4-biphenylyl)-N-1H-indazol-5-yl-6-methyl-2-oxo-1,2,3,4-tetrahydro-5-pyrimidinecarboxamide;
N-1H-Indazol-5-yl-6-methyl-4-[4'-(methyloxy)-4-biphenylyl]-2-oxo-1,2,3,4-tetrahydro-5-pyrimidinecarboxamide;
4-(4'-Chloro-4-biphenylyl)-N-1H-indazol-5-yl-6-methyl-2-oxo-1,2,3,4-tetrahydro-5-pyrimidinecarboxamide;
4-(3'-Acetyl-4-biphenylyl)-N-1H-indazol-5-yl-6-methyl-2-oxo-1,2,3,4-tetrahydro-5-pyrimidinecarboxamide;
4-(3'-Chloro-4-biphenylyl)-N-1H-indazol-5-yl-6-methyl-2-oxo-1,2,3,4-tetrahydro-5-pyrimidinecarboxamide;
4-[4-(1,3-Benzodioxol-5-yl)phenyl]-N-1H-indazol-5-yl-6-methyl-2-oxo-1,2,3,4-tetrahydro-5-pyrimidinecarboxamide;
N-1H-Indazol-5-yl-6-methyl-2-oxo-4-[4'-(trifluoromethyl)-4-biphenylyl]-1,2,3,4-tetrahydro-5-pyrimidinecarboxamide;
4-(2'-Chloro-4-biphenylyl)-N-1H-indazol-5-yl-6-methyl-2-oxo-1,2,3,4-tetrahydro-5-pyrimidinecarboxamide;
4-[4'-(Dimethylamino)-4-biphenylyl]-N-1H-indazol-5-yl-6-methyl-2-oxo-1,2,3,4-tetrahydro-5-pyrimidinecarboxamide;
4-[4'-(Dimethylamino)-4-biphenylyl]-N-1H-indazol-5-yl-6-methyl-2-oxo-1,2,3,4-tetrahydro-5-pyrimidinecarboxamide;
N-1H-Indazol-5-yl-6-methyl-4-[2'-(methyloxy)-4-biphenylyl]-2-oxo-1,2,3,4-tetrahydro-5-pyrimidinecarboxamide;
N-1H-Indazol-5-yl-6-methyl-4-[3'-(methyloxy)-4-biphenylyl]-2-oxo-1,2,3,4-tetrahydro-5-pyrimidinecarboxamide;
N-1H-Indazol-5-yl-4-[4-(1H-indol-5-yl)phenyl]-6-methyl-2-oxo-1,2,3,4-tetrahydro-5-pyrimidinecarboxamide;
4-[4-(3,5-Dimethyl-4-isoxazolyl)phenyl]-N-1H-indazol-5-yl-6-methyl-2-oxo-1,2,3,4-tetrahydro-5-pyrimidinecarboxamide;
N-1H-Indazol-5-yl-6-methyl-2-oxo-4-[4-(1H-pyrazol-4-yl)phenyl]-1,2,3,4-tetrahydro-5-pyrimidinecarboxamide;
4-[3',5'-Bis(trifluoromethyl)-4-biphenylyl]-N-1H-indazol-5-yl-6-methyl-2-oxo-1,2,3,4-tetrahydro-5-pyrimidinecarboxamide;
4-[2-Fluoro-4-(trifluoromethyl)phenyl]-N-1H-indazol-5-yl-6-methyl-2-oxo-1,2,3,4-tetrahydro-5-pyrimidinecarboxamide;
4-[2-Fluoro-3-(trifluoromethyl)phenyl]-N-1H-indazol-5-yl-6-methyl-2-oxo-1,2,3,4-tetrahydro-5-pyrimidinecarboxamide;
4-(2,6-Difluorophenyl)-N-1H-indazol-5-yl-6-methyl-2-oxo-1,2,3,4-tetrahydro-5-pyrimidinecarboxamide;
4-(3'-Amino-3-biphenylyl)-N-1H-indazol-5-yl-6-methyl-2-oxo-1,2,3,4-tetrahydro-5-pyrimidinecarboxamide;
4-(2',4'-Difluoro-3-biphenylyl)-N-1H-indazol-5-yl-6-methyl-2-oxo-1,2,3,4-tetrahydro-5-pyrimidinecarboxamide;
4-(3-Biphenylyl)-N-1H-indazol-5-yl-6-methyl-2-oxo-1,2,3,4-tetrahydro-5-pyrimidinecarboxamide;
N-1H-Indazol-5-yl-6-methyl-2-oxo-4-[3-(3-thienyl)phenyl]-1,2,3,4-tetrahydro-5-pyrimidinecarboxamide;
N-1H-Indazol-5-yl-6-methyl-2-oxo-4-{5-[4-(trifluoromethyl)phenyl]-2-thienyl}-1,2,3,4-tetrahydro-5-pyrimidinecarboxamide;
4-[5-(4-Chlorophenyl)-2-thienyl]-N-1H-indazol-5-yl-6-methyl-2-oxo-,1,2,3,4-tetrahydro-5-pyrimidinecarboxamide;
N-1H-Indazol-5-yl-6-methyl-4-{5-[4-(methyloxy)phenyl]-2-thienyl}-2-oxo-1,2,3,4-tetrahydro-5-pyrimidinecarboxamide;
4-(2,3'-Bithien-5-yl)-N-1H-indazol-5-yl-6-methyl-2-oxo-1,2,3,4-tetrahydro-5-pyrimidinecarboxamide; and
6-methyl-N-(3-methyl-1H-indazol-5-yl)-4-(2-naphthalenyl)-2-oxo-1,2,3,4-tetrahydro-5-pyrimidinecarboxamide;

or a salt, solvate, or physiologically functional derivative thereof.

Further examples of compounds of the present invention include:
4-(3,5-difluoro-phenyl)-6-methyl-2-oxo-1,2,3,4-tetrahydro-pyrimidine-5-carboxylic acid [3-(3-fluoro-phenylamino)-1H-indazol-5-yl]-amide;
4-(3,5-difluoro-phenyl)-6-methyl-2-oxo-1,2,3,4-tetrahydro-pyrimidine-5-carboxylic acid [3-(3,5-difluoro-phenylamino)-1H-indazol-5-yl]-amide;
4-(3,4-difluoro-phenyl)-6-methyl-2-oxo-1,2,3,4-tetrahydro-pyrimidine-5-carboxylic acid [3-(3,5-difluoro-phenylamino)-1H-indazol-5-yl]-amide;
4-(3,4-difluoro-phenyl)-6-methyl-2-oxo-1,2,3,4-tetrahydro-pyrimidine-5-carboxylic acid [3-(3-fluoro-phenylamino)-1H-indazol-5-yl]-amide;
6-methyl-2-oxo-4-(4-trifluoromethyl-phenyl)-1,2,3,4-tetrahydro-pyrimidine-5 -carboxylic acid [3-(3,5-difluoro-phenylamino)-1H-indazol-5-yl]-amide;
4-(4-chloro-2-fluoro-phenyl)-6-methyl-2-oxo-1,2,3,4-tetrahydro-pyrimidine-5-carboxylic acid [3-(3,5-difluoro-phenylamino)-1H-indazol-5-yl]-amide;
4-(3,5-difluoro-phenyl)-6-methyl-2-oxo-1,2,3,4-tetrahydro-pyrimidine-5-carboxylic acid [3-(4-fluoro-phenylamino)-1H-indazol-5-yl]-amide;
4-(3,4-difluoro-phenyl)-6-methyl-2-oxo-1,2,3,4-tetrahydro-pyrimidine-5-carboxylic acid [3-(4-fluoro-phenylamino)-1H-indazol-5-yl]-amide; and
4-(3,5-difluoro-phenyl)-6-methyl-2-oxo-1,2,3,4-tetrahydro-pyrimidine-5-carboxylic acid [3-(4-fluoro-phenyl)-1H-indazol-5-yl]-amide;

or a salt, solvate, or physiologically functional derivative thereof.

Typically, the salts of the present invention are pharmaceutically acceptable salts. Salts encompassed within the term "pharmaceutically acceptable salts" refer to non-toxic salts of the compounds of this invention. Salts of the compounds of the present invention may comprise acid addition salts derived from a nitrogen on a substituent in the compound of formula (I). Representative salts include the following salts: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, Iodide, isethionate, lactate, lactobionate, laurate, malate, maleate, mandelate, mesylate, methylbromide, methylnitrate, methylsulfate, monopotassium maleate, mucate, napsylate, nitrate, N-methylglucamine, oxalate, pamoate (embonate), palmitate, pantothenate, phosphateldiphosphate, polygalacturonate, potassium, salicylate, sodium, stearate, subacetate, succinate, tannate, tartrate, teoclate, tosylate, triethiodide, trimethylammonium and valerate. Other salts, which are not pharmaceutically acceptable, may be useful in the preparation of compounds of this invention and these form a further aspect of the invention.

While it is possible that, for use in therapy, therapeutically effective amounts of a compound of formula (I), as well as salts, solvates and physiological functional derivatives thereof, may be administered as the raw chemical, it is possible to present the active ingredient as a pharmaceutical composition. Accordingly, the invention further provides pharmaceutical compositions, which include therapeutically effective amounts of compounds of the formula (I) and salts, solvates and physiological functional derivatives thereof, and one or more pharmaceutically acceptable carriers, diluents, or excipients. The compounds of the formula (I) and salts, solvates and physiological functional derivatives thereof, are as described above. The carrier(s), diluent(s) or excipient(s) must be acceptable in the sense of being compatible with the other ingredients of the formulation and not deleterious to the recipient thereof. In accordance with another aspect of the invention there is also provided a process for the preparation of a pharmaceutical formulation including admixing a compound of the formula (I), or salts, solvates and physiological functional derivatives thereof, with one or more pharmaceutically acceptable carriers, diluents or excipients.

Pharmaceutical formulations may be presented In unit dose forms containing a predetermined amount of active ingredient per unit dose. Such a unit may contain, for example, 0.5 mg to 1 g, preferably 1 mg to 700 mg, more preferably 5 mg to 100 mg of a compound of the formula (I), depending on the condition being treated, the route of administration and the age, weight and condition of the patient, or pharmaceutical formulations may be presented in unit dose forms containing a predetermined amount of active ingredient per unit dose. Preferred unit dosage formulations are those containing a daily dose or sub-dose, as herein above recited, or an appropriate fraction thereof, of an active Ingredient. Furthermore, such pharmaceutical formulations may be prepared by any of the methods well known in the pharmacy art.

Pharmaceutical formulations may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules are made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing Inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax or the like.

The compounds of formula (I), and salts, solvates and physiological functional derivatives thereof, can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of formula (I) and salts, solvates and physiological functional derivatives thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamide-phenol, polyhydroxyethylaspartamldephenol, or polyethyleneoxidepolylysine substituted with palmitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986).

Pharmaceutical formulations adapted for topical administration may be formulated as ointments, creams, suspensions, lotions, powders, solutions, pastes, gels, sprays, aerosols or oils.

For treatments of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles and mouth washes.

Pharmaceutical formulations adapted for rectal administration may be presented as suppositories or as enemas.

Pharmaceutical formulations adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include fine particle dusts or mists, which may be generated by means of various types of metered, dose pressurised aerosols, nebulizers or insufflators.

Pharmaceutical formulations adapted for vaginal administration may be presented as pessaries, tampons, creams, gels, pastes, foams or spray formulations.

Pharmaceutical formulations adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented In unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

It should be understood that In addition to the ingredients particularly mentioned above, the formulations may include other agents conventional in the art having regard to the type of formulation in question, for example those suitable for oral administration may include flavouring agents.

A therapeutically effective amount of a compound of the present invention will depend upon a number of factors including, for example, the age and weight of the human or other animal, the precise condition requiring treatment and its severity, the nature of the formulation, and the route of administration, and will ultimately be at the discretion of the attendant physician or veterinarian. However, an effective amount of a compound of formula (I) for the treatment of neoplastic growth, for example colon or breast carcinoma, will generally be in the range of 0.1 to 100 mg/kg body weight of recipient (mammal) per day and more usually in the range of 1 to 10 mg/kg body weight per day. Thus, for a 70 kg adult mammal, the actual amount per day would usually be from 70 to 700 mg and this amount may be given in a single dose per day or more usually in a number (such as two, three, four, five or six) of sub-doses per day such that the total daily dose is the same. An effective amount of a salt or solvate, or physiologically functional derivative thereof, may be determined as a proportion of the effective amount of the compound of formula (I) per se. It is envisaged that similar dosages would be appropriate for treatment of the other conditions referred to above.

The compounds of this invention may be made by a variety of methods, including standard chemistry. Any previously defined variable will continue to have the previously defined meaning unless otherwise indicated. Illustrative general synthetic methods are set out below and then specific compounds of the invention are prepared in the Working Examples.

Compounds of general formula (I) may be prepared by methods known in the art of organic synthesis as set forth in part by the following synthesis schemes. In all of the schemes described below, it is well understood that protecting groups for sensitive or reactive groups are employed where necessary in accordance with general principles of chemistry. Protecting groups are manipulated according to standard methods of organic synthesis (T. W. Green and P. G. M. Wuts (1991) *Protecting Groups in Organic Synthesis*, John Wiley & Sons). These groups are removed at a convenient stage of the compound synthesis using methods that are readily apparent to those skilled in the art. The selection of processes as well as the reaction conditions and order of their execution shall be consistent with the preparation of compounds of Formula (I).

Compounds of general formula (I) can be prepared according to the synthetic sequences illustrated in Schemes 1-5 and further detailed in the Examples section following.

Scheme 1

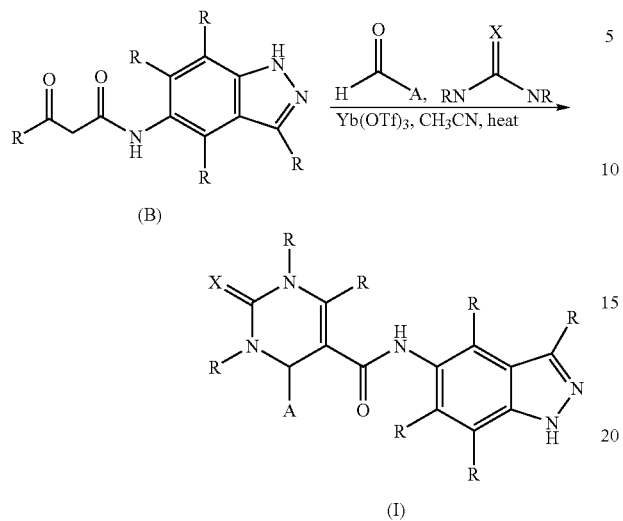

As illustrated in Scheme 1, compounds of general formula (I) may be synthesized from the beta-ketoamide (B). One way this beta-ketoamide can be converted to the pyrimidinone product is by condensation with an aldehyde and urea in an appropriate solvent at temperatures between 100 and 180° C. in the presence of an appropriate additive. For example, heating the beta-ketoamide with an aldehyde and urea in $CH_3CN$ at 100° C. In a microwave for 10 minutes, in the presence of ytterbium triflate provides the pyrimidinone (I).

Scheme 2

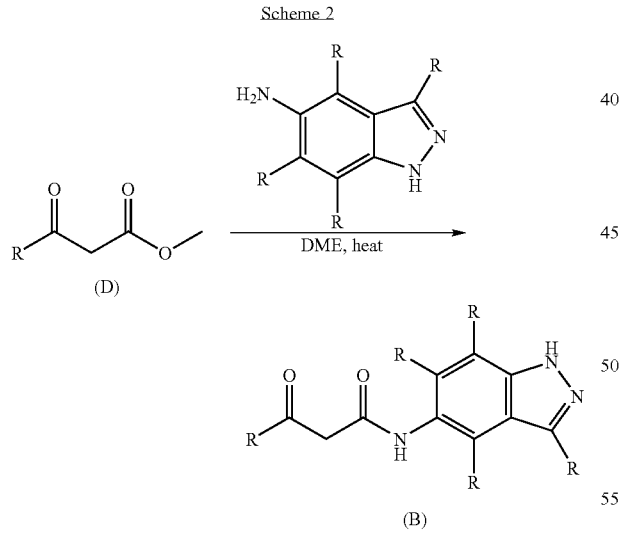

Compounds of general formula (B) can be prepared as shown in Scheme 2.

For example, microwave heating of 5-aminoindazole in an excess of a beta-ketoester at 200° C. for 200 seconds provides the corresponding beta-ketoamide (B). This transformation can also be accomplished by heating the reagents in an appropriate solvent, such as ethyleneglycol dimethylether.

Scheme 3

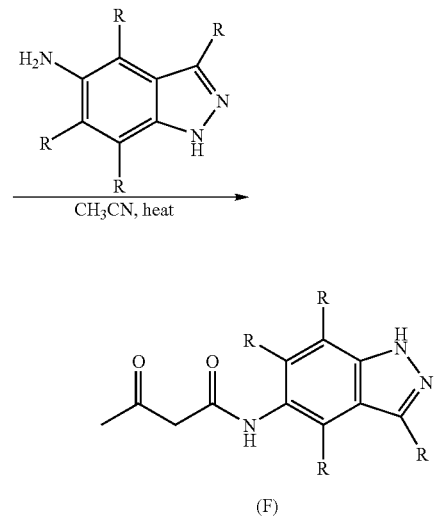

Another method which can be used to generate, specifically, N-1H-indazol-5-yl-3-oxobutanamide (F) is shown in Scheme 3. This transformation involves combining 5-aminoindazole and diketene (E) in acetonitrile and heating to 50° C. in a sealed tube.

Scheme 4

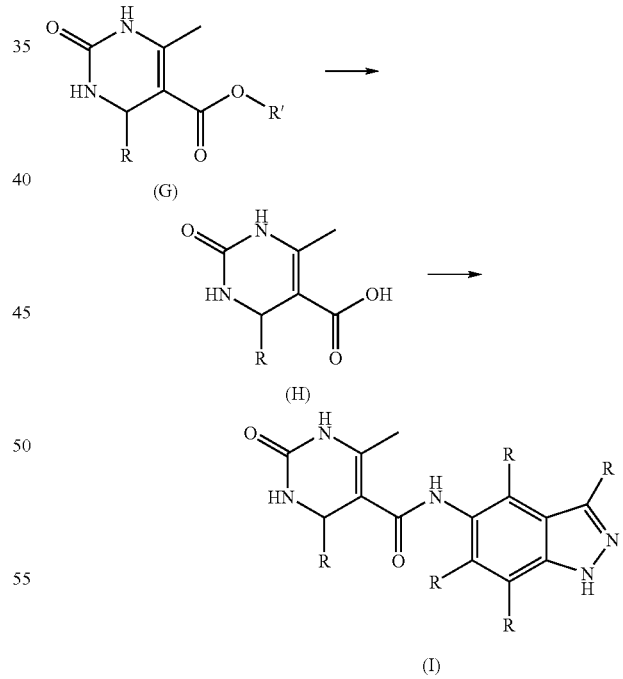

Compounds of general formula (I) may also be synthesized from compounds of general formula (H), as depicted in Scheme 4. Compounds of general formula (H) may be synthesized from compounds of general formula (G) by conversion of the ester to a carboxylic acid. This transformation is dependent upon the type of ester used, and can be accomplished with a variety of conditions for each type of ester, examples of which can be found in the literature, specifically "Protective Groups on Organic Synthesis" by Greene and Wuts. Coupling of the resulting carboxylic acid with 5-aminoindazole provides the compound of general formula (I). This conversion from the carboxylic acid to the amide can be executed using a variety of reaction conditions. For example, dissolving the carboxylic acid and 5-aminoindazole in dimethylformamide and heating with diisopropylethylamine, 4-(dimethylamino)-pyridine and dicyclohexylcarbodiimide provides the desired pyrimidinone (1).

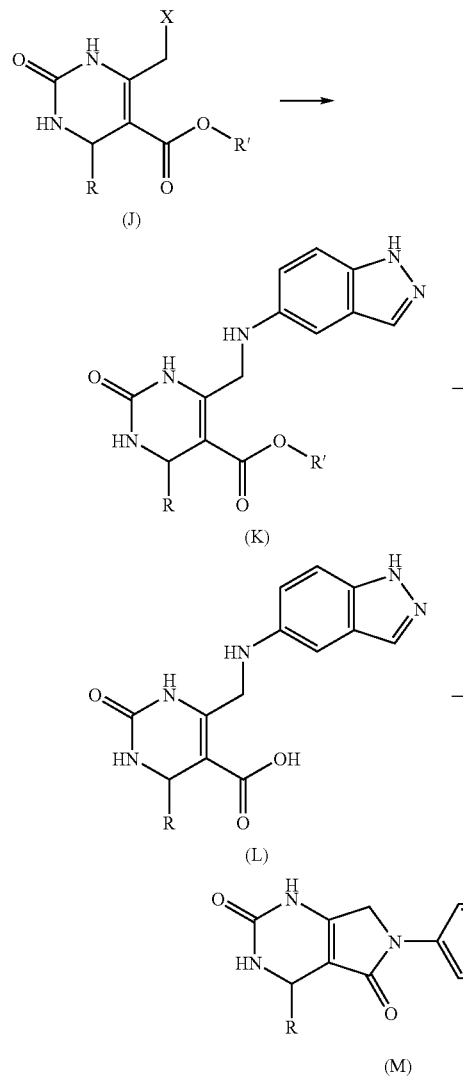

Compounds of formula (J) can be further transformed to compounds of formula L. Displacement of a suitable leaving group (X), for example chlorine, with aminoindazoles generates amines of general formula (K). Compounds of general formula (L) may be synthesized from compounds of general formula (K) by conversion of the ester to a carboxylic acid. This transformation is dependent upon the type of ester used, and can be accomplished with a variety of conditions for each type of ester, examples of which can be found in the literature, specifically "Protective Groups on Organic Synthesis" by Greene and Wuts. Dehydration of the resulting amino acid affords amide (M). This conversion from the carboxylic acid to the amide can be executed using a variety of reaction conditions. For example, dissolving the carboxylic acid and 5-aminoindazole in dimethylformamide and heating with diisopropylethylamine, 4-(dimethylamino)-pyridine and dicyclohexylcarbodiimide provides the desired pyrimidinone (1).

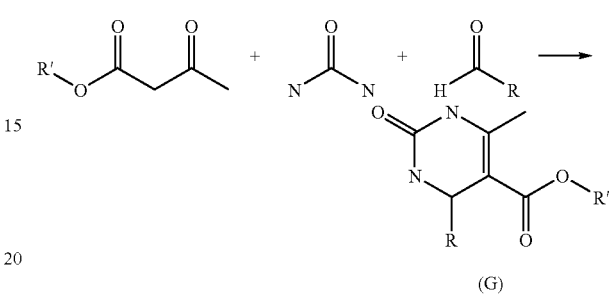

Compounds of formula (G) may be synthesized by reaction of a beta-ketoester, an aldehyde and urea in an appropriate solvent containing a suitable additive. There are a variety of conditions known In the chemical literature that are useful for preparing this type of compound. For example, one can combine these reagents in ethanol containing a catalytic amount of hydrochloric acid and heat to reflux for several hours. For this type of reaction, a number of catalysts, solvents, and temperature combinations have been explored and have proven useful for carrying out the desired transformation.

Certain embodiments of the present invention will now be illustrated by way of example only. The physical data given for the compounds exemplified is consistent with the assigned structure of those compounds.

EXAMPLES

As used herein the symbols and conventions used in these processes, schemes and examples are consistent with those used in the contemporary scientific literature, for example, the Journal of the American Chemical Society or the Journal of Biological Chemistry. Standard single-letter or three-letter abbreviations are generally used to designate amino acid residues, which are assumed to be in the L-configuration unless otherwise noted. Unless otherwise noted, all starting materials were obtained from commercial suppliers and used without further purification. Specifically, the following abbreviations may be used in the examples and throughout the specification:

g (grams); mg (milligrams);
L (liters); mL (milliliters);
μL (microliters); psi (pounds per square inch);
M (molar); mM (millimolar);
i.v. (intravenous); Hz (Hertz);
MHz (megaHertz); mol (moles);
mmol (millimoles); rt (room temperature);
min (minutes); h (hours);
mp (melting point); TLC (thin layer chromatography);
$T_r$ (retention time); RP (reverse phase);
MeOH (methanol); i-PrOH (isopropanol);
TEA (triethylamine); TFA (trifluoroacetic acid);
TFAA (trifluoroacetic anhydride); THF (tetrahydrofuran);
DMSO (dimethylsulfoxide); AcOEt or EtOAc (ethyl acetate);

DME (1,2-dimethoxyethane); DCM (dichloromethane); DCE (dichloroethane); DMF (N,N-dimethylformamide); DMPU (N,N'-dimethylpropyleneurea); CDI (1,1'-carbonyldiimidazole);
IBCF (isobutyl chloroformate); HOAc (acetic acid);
HOSu (N-hydroxysuccinimide); HOBT (1-hydroxybenzotriazole);
mCPBA (meta-chloroperbenzoic acid);
EDC (1-[(3-dimethylamino) propyl]-3-ethylcarbodiimide hydrochloride);
BOC (tert-butyloxycarbonyl); FMOC (9-fluorenylmethoxycarbonyl);
DCC (dicyclohexylcarbodiimide); CBZ (benzyloxycarbonyl);
Ac (acetyl); atm (atmosphere);
TMSE (2-(trimethylsilyl)ethyl); TMS (trimethylsilyl);
TIPS (triisopropylsilyl); TBS (t-butyldimethylsilyl);
DMAP (4-dimethylaminopyridine); BSA (bovine serum albumin)
ATP (adenosine triphosphate); HRP (horseradish peroxidase);
DMEM (Dulbecco's modified Eagle medium);
HPLC (high pressure liquid chromatography);
BOP (bis(2-oxo-3-oxazolidinyl)phosphinic chloride);
TBAF (tetra-n-butylammonium fluoride);
HBTU (O-Benzotriazole-1-yl-N,N,N',N'-tetramethyluroniumhexafluoro phosphate).
HEPES (4-(2-hydroxyethyl)-1-piperazine ethane sulfonic acid);
DPPA (diphenylphosphoryl azide);
fHNO$_3$ (fuming HNO$_3$); and
EDTA (ethylenediaminetetraacetic acid).

All references to ether are to diethyl ether; brine refers to a saturated aqueous solution of NaCl. Unless otherwise indicated, all temperatures are expressed in ° C. (degrees Centigrade). All reactions are conducted under an inert atmosphere at room temperature unless otherwise noted.

$^1$H NMR spectra were recorded on a Varian VXR-300, a Varian Unity-300, a Varian Unity-400 instrument, a Brucker AVANCE-400, or a General Electric QE-300. Chemical shifts are expressed in parts per million (ppm, δ units). Coupling constants are in units of Hertz (Hz). Splitting patterns describe apparent multiplicities and are designated as s (singlet), d (doublet), t (triplet), q (quartet), quint (quintet), m (multiplet), br (broad).

HPLC were recorded on a Gilson HPLC or Shimadzu HPLC system by the following conditions. Column: 50×4.6 mm (id) stainless steel packed with 5 μm Phenomenex Luna C-18; Flow rate: 2.0 mL/min; Mobile phase: A phase =50 mM ammonium acetate (pH 7.4), B phase =acetonitrile, 0-0.5 min LA: 100%, B: 0%), 0.5-3.0 min (A: 100-0%, B: 0-100%), 3.0-3.5 min (A: 0%, B: 100%), 3.5-3.7 min (A: 0-100%, B: 100-0%), 3.7-4.5 min (A: 100%, B: 0%); Detection: UV 254 nm; Injection volume: 3 □L. Low-resolution mass spectra (MS) were recorded on a JOEL JMS-AX505HA, JOEL SX-102, or a SCIEX-APIiii spectrometer; LC-MS were recorded on a micromass 2MD and Waters 2690; high resolution MS were obtained using a JOEL SX-102A spectrometer. All mass spectra were taken under electrospray ionization (ESI), chemical ionization (CI), electron impact (EI) or by fast atom bombardment (FAB) methods. Infrared (IR) spectra were obtained on a Nicolet 510 FT-IR spectrometer using a 1-mm NaCl cell. Most of the reactions were monitored by thin-layer chromatography on 0.25 mm E. Merck silica gel plates (60 F-254), visualized with UV light, 5% ethanolic phosphomolybdic acid or p-anisaldehyde solution. Flash column chromatography was performed on silica gel (230-400 mesh, Merck).

Example 1

4-(4-fluorophenyl)-N-1H-indazol-5-yl-6-methyl-2-oxo-1,2,3,4-tetrahydro-5-pyrimidinecarboxamide

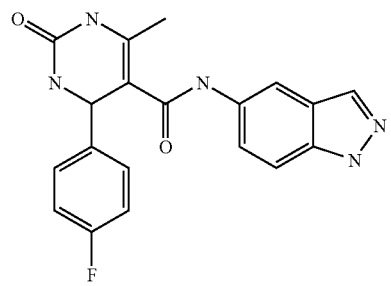

(a) N-1H-indazol-5-yl-3-oxobutanamide

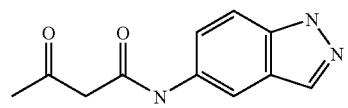

In a round-bottomed flask 5-aminoindazole (500 mg, 3.75 mmol, 1 equiv) was suspended in acetonitrile (1 mL). In a separate flask, diketene (stabilized w/copper sulfate, 0.289 mL, 3.75 mmol, 1 equiv) was dissolved in acetonitrile. The diketene solution was added to the amine suspension in four portions. The reaction was sealed and heated to 50° C. for 14 h. The mixture was diluted with diethyl ether (approx. 2 mL) and the solid product was collected by filtration and washed several times with diethyl ether. The ketoamide was isolated as a white powder (761 mg, 94%).

NMR $^1$H NMR (400 MHz, DMSO-D6) δ ppm 12.98 (s, 1H), 10.08 (s, 1H), 8.12 (s, 1H), 8.02 (s, 1H), 7.48 (d, 1H), 7.38 (d, 1H), 3.56 (s, 2H), 2.22 (s, 3H). MS m/z 218 (M+1)$^+$.

(b) preparation of 4-(4-fluorophenyl)-N-1H-indazol-5-yl-6-methyl-2-oxo-1,2,3,4-tetrahydro-5-pyrimidinecarboxamide

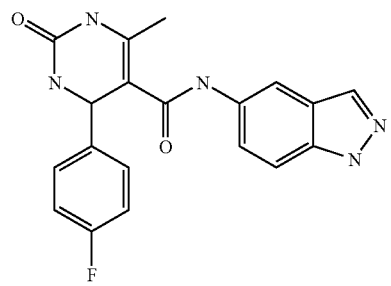

Method A: Urea (21 mg, 1.5 equiv), p-fluorobenzaldehyde (27 μL, 1.1 equiv), N-1H-indazol-5-yl-3-oxobutanamide (made in example 1(a), 50 mg, 1 equiv) and ytterbium triflate (14 mg, 0.1 equiv) were combined in acetonitrile (1 mL) and heated to 100° C. in a SmithSynthesizer for 10 minutes. The residue was diluted with 0.5 mL of water and the product was collected by filtration. The solids were washed with a 1:1 solution of acetonitrile and diethyl ether then air-dried to provide the final product (62 mg, 80%). Any products of unacceptable purity were purified further by silica gel chromatography.

1H NMR (400 MHz, DMSO-D6) δ ppm 12.94 (s, 1H), 9.58 (s, 1H), 8.74 (s, 1H), 8.02 (s, 1H), 7.98 (s, 1H), 7.60 (s, 1H), 7.40 (m, 2H), 7.32 (m, 2H), 7.17 (m, 2H), 5.42 (s, 1H), 2.05 (s, 3H). MS (ES+) m/e 366 [M+H]+

Method B: Urea (21 mg, 1.5 equiv), p-fluorobenzaldehyde (27 μL, 1.1 equiv), N-1H-indazol-5-yl-3-oxobutanamide (made in example 1(a), 50 mg, 1 equiv) and ytterbium triflate (14 mg, 0.1 equiv) were combined in acetonitrile (1 mL) and heated to 100° C. in a sealed tube for three hours. The residue was diluted with 0.5 mL of water and the product was collected by filtration. The solids were washed with a 1:1 solution of acetonitrile and diethyl ether then air-dried to provide the final product (62 mg, 80%). Any products of unacceptable purity were purified further by silica gel chromatography.

1H NMR (400 MHz, DMSO-D6) δ ppm 12.94 (s, 1H), 9.58 (s, 1H), 8.74 (s, 1H), 8.02 (s, 1H), 7.98 (s, 1H), 7.60 (s, 1H), 7.40 (m, 2H), 7.32 (m, 2H), 7.17 (m, 2H), 5.42 (s, 1H), 2.05 (s, 3H). MS (ES+) m/e 366 [M+H]+

Example 2

4-[3,4-bis(ethyloxy)phenyl]-N-1H-indazol-5-yl-6-methyl-2-oxo-1,2,3,4-tetrahydro-5-pyrimidinecarboxamide

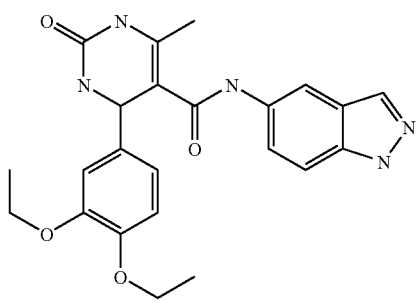

The title compound was synthesized using the procedure recited in Example 1(b), except 3,4-dimethoxybenzaldehyde was utilized.

1H NMR (400 MHz, DMSO-D6) δ ppm 12.90 (s, 1H), 9.52 (s, 1H), 8.61 (s, 1H), 8.02 (s, 1H), 7.96 (s, 1H), 7.45 (s, 1H), 7.40 (m, 2H), 6.75-6.90 (m, 3H), 5.35 (s, 1H), 3.80-4.00 (m, 4H), 2.02 (s, 3H), 1.20-1.30 (m, 6H). MS (ES−) m/z 434.

Example 3

N-1H-indazol-5-yl-6-methyl-4-[4-(methylsulfonyl)phenyl]-2-oxo-1,2,3,4-tetrahydro-5-pyrimidinecarboxamide

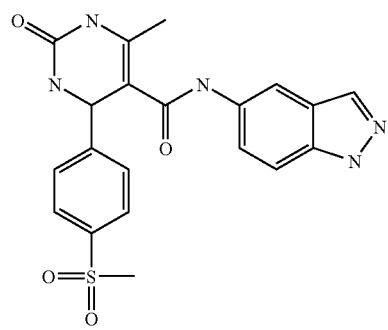

The title compound was synthesized using the procedure recited in Example 1(b), except 4-methansulfonylbenzaldehyde was utilized.

1H NMR (400 MHz, DMSO-D6) δ ppm 12.96 (s, 1H), 9.43 (s, 1H), 8.82 (s, 1H), 8.02 (s, 1H), 7.98 (s, 1H), 7.92 (d, 2H), 7.72 (s, 1H), 7.55 (d, 2H), 7.42 (m, 2H), 5.51 (s, 1H), 3.20 (s, 3H), 2.06 (s, 3H). MS (ES+) m/e 426 [M+H]+.

Example 4

N-1H-indazol-5-yl-6-methyl-2-oxo-4-(3-thienyl)-1,2,3,4-tetrahydro-5-pyrimidinecarboxamide

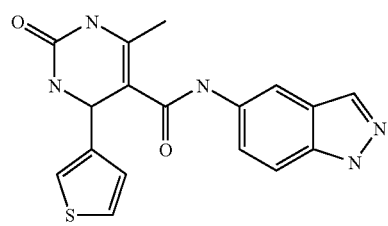

The title compound was synthesized using the procedure recited in Example 1(b), except 3-thiophenecarboxaldehyde was utilized.

1H NMR (400 MHz, DMSO-D6) δ ppm 12.92 (s, 1H), 9.58 (s, 1H), 8.68 (s, 1H), 8.02 (s, 1H), 7.98 (s, 1H), 7.60 (s, 1H), 7.45 (m, 1H), 7.40 (s, 2H), 7.22 (s, 1H), 7.02 (m, 1H), 5.42 (s, 1H), 2.02 (s, 3H). MS (ES+) m/e 354 [M+H]+.

Example 5

N-1H-indazol-5-yl-4,6-dimethyl-2-oxo-1,2,3,4-tetrahydro-5-pyrimidinecarboxamide

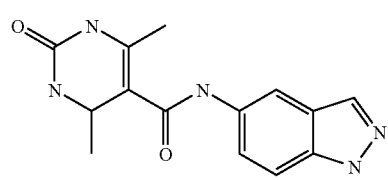

The title compound was synthesized using the procedure recited in Example 1(b), except acetaldehyde was utilized.

1H NMR (400 MHz, DMSO-D6) δ ppm 12.93 (s, 1H), 9.58 (s, 1H), 8.45 (s, 1H), 8.06 (s, 1H), 7.98 (s, 1H), 7.40-7.48 (m, 2H), 7.02 (s, 1H), 4.25 (m, 1H), 1.92 (s, 3H), 1.16 (d, 3H). MS (ES+) m/e 286 [M+H]+.

Example 6

N-1H-indazol-5-yl-6-methyl-4-(1-naphthalenyl)-2-oxo-1,2,3,4-tetrahydro-5-pyrimidinecarboxamide

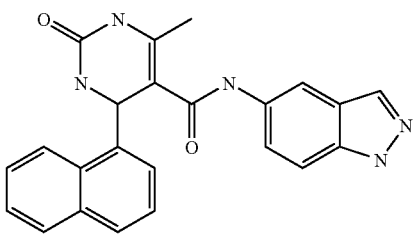

The title compound was synthesized using the procedure recited in Example 1(b), except 1-naphthaldehyde was utilized.

1H NMR (400 MHz, DMSO-D6) δ ppm 12.86 (s, 1H), 9.61 (s, 1H), 8.78 (s, 1H), 8.32 (d, 1H), 7.92 (m, 3H), 7.83 (d, 1H), 7.45-7.60 (m, 5H), 7.35 (d, 1H), 7.29 (d, 1H), 6.24 (s, 1H), 2.12 (s, 3H). MS (ES+) m/e 398 [M+H]+.

Example 7

N-1H-indazol-5-yl-6-methyl-4-(2-naphthalenyl)-2-oxo-1,2,3,4-tetrahydro-5-pyrimidinecarboxamide

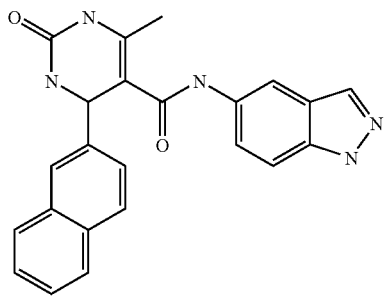

The title compound was synthesized using the procedure recited In Example 1(b), except 2-naphthaldehyde was utilized.

1H NMR (400 MHz, DMSO-D6) δ ppm 12.88 (s, 1H), 9.60 (s, 1H), 8.72 (s, 1H), 7.80-8.00 (m, 5H), 7.71 (s, 1H), 7.63 (s, 1H), 7.45-7.50 (m, 3H), 7.38 (m; 2H), 5.59 (s, 1H), 2.05 (s, 3H). MS (ES+) m/e 398 [M+H]+.

Example 8

4-{5-[(1H-indazol-5-ylamino)carbonyl]-6-methyl-2-oxo-1,2,3,4-tetrahydro-4-pyrimidinyl}benzoic acid

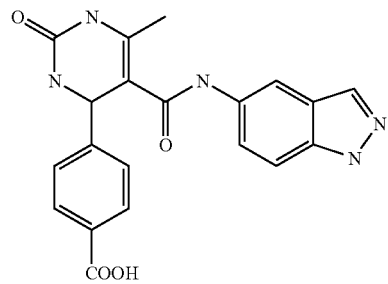

The title compound was synthesized using the procedure recited in Example 1 (b), except 4-formylbenzoic acid was utilized. 1H NMR (400 MHz, DMSO-D6) δ ppm 12.88 (s, 1H), 9.61 (s, 1H), 8.78 (s, 1H), 8.05 (d, 2H), 7.93 (d 2H), 7.71 (s, 1H), 7.45 (d, 4H), 5.5 (s, 1H), 2.12 (s, 3H). MS (ES+) m/e 392 [M+H]+.

Example 9

4-(2,4-difluorophenyl)-N-1H-indazol-5-yl-6-methyl-2-oxo-1,2,3,4-tetrahydro-5-pyrimidinecarboxamide

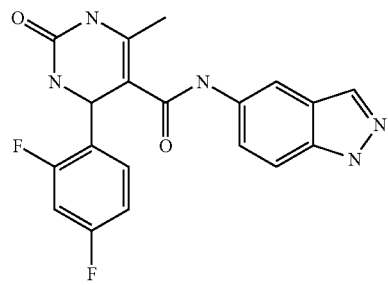

The title compound was synthesized using the procedure recited in Example 1 (b), except 2,4-difluorobenzaldehyde was utilized. 1H NMR (400 MHz, DMSO-D6) δ ppm 12.88 (s, 1H), 9.63 (s, 1H), 8.8 (s, 1H), 8 (d, 2H), 7.55 (s, 1H), 7.42 (m, 3H), 7.15 (m, 2H), 5.62 (s, 1H), 2.12 (s, 3H). MS (ES+) m/e 384 [M+H]+.

Example 10

N-1H-indazol-5-yl-6-methyl-4-[3-(methyloxy)phenyl]-2-oxo-1,2,3,4-tetrahydro-5-pyrimidinecarboxamide

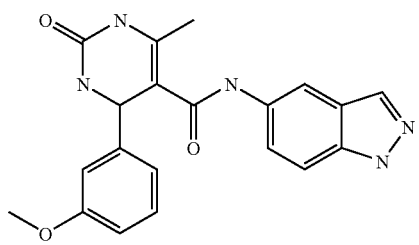

The title compound was synthesized using the procedure recited in Example 1 (b), except 3-methoxybenzaldehyde was utilized. $^1$H NMR (400 MHz, DMSO-D6) δ ppm 12.88 (s, 1H), 9.62 (s, 1H), 8.65 (s, 1H), 8.05 (d, 2H), 7.6 (s, 1H), 7.46 (s, 2H), 7.26 (t, 1H), 6.8 (m, 3H), 5.45 (s, 1H), 3.71 (s, 3H), 2.15 (s, 3H). MS (ES+) m/e 378 [M+H]$^+$.

Example 11

N-1H-indazol-5-yl-6-methyl-4-[2-(methyloxy)phenyl]-2-oxo-1,2,3,4-tetrahydro-5-pyrimidinecarboxamide

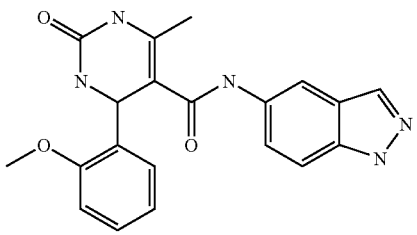

The title compound was synthesized using the procedure recited in Example 1 (b), except 2-methoxybenzaldehyde was utilized. $^1$H NMR (400 MHz, DMSO-D6) δ ppm 12.88 (s, 1H), 9.6 (s, 1H), 8.6 (s, 1H), 8.12 (d, 2H), 7.45 (s, 2H), 7.35 (m, 2H), 7.1 (s, 1H), 6.85 (m, 2H), 5.71 (s, 1H), 3.72 (s, 3H), 2.16 (s, 3H). MS (ES+) m/e 378 [M+H]$^+$.

Example 12

4-(4-cyanophenyl)-N-1H-indazol-5-yl-6-methyl-2-oxo-1,2,3,4-tetrahydro-5-pyrimidinecarboxamide

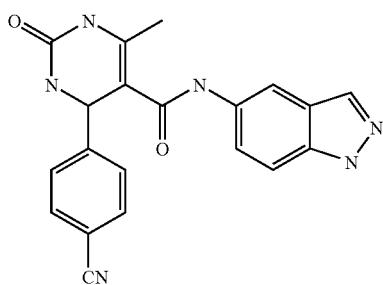

The title compound was synthesized using the procedure recited in Example 1 (b), except 4-cyanobenzaldehyde was utilized. $^1$H NMR (400 MHz, DMSO-D6) δ ppm 12.88 (s, 1H), 9.62 (s, 1H), 8.81 (s, 1H), 8.03 (d, 2H), 7.83 (s, 1H), 7.5 (d, 2H), 7.43 (d, 2H), 5.5 (s, 1H), 2.08 (s, 3H). MS (ES+) m/e 373 [M+H]$^+$.

Example 13

3-{5-[(1H-indazol-5-ylamino)carbonyl]-6-methyl-2-oxo-1,2,3,4-tetrahydro-4-pyrimidinyl}benzoic acid

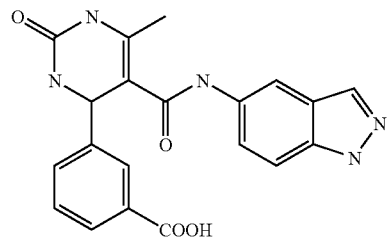

The title compound was synthesized using the procedure recited in Example 1 (b), except 3-formylbenzoic acid was utilized. 1H NMR (400 MHz, DMSO-D6) δ ppm 13 (s, 2H), 9.63 (s, 1H), 8.8 (s, 1H), 8 (m, 3H), 7.86 (d, 1H), 7.66 (s, 1H), 7.45 (m, 4H), 5.45 (s, 1H), 2.07 (s, 2H). MS (ES+) m/e 392 [M+H]$^+$.

Example 14

4-(2-fluorophenyl)-N-1H-indazol-5-yl-6-methyl-2-oxo-1,2,3,4-tetrahydro-5-pyrimidinecarboxamide

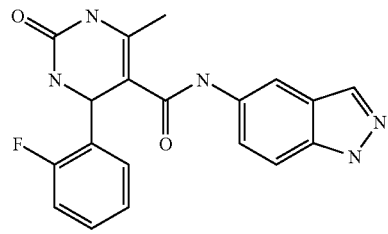

The title compound was synthesized using the procedure recited in Example 1(b), except 2-fluorobenzaldehyde was utilized. 1H NMR (400 MHz, DMSO-D6) δ ppm 12.88 (s, 1H), 9.65 (s, 1H), 8.77 (s, 1H), 8 (d, 2H), 7.53 (s, 1H), 7.4 (m, 3H), 7.3 (m, 1H), 7.15 (m, 2H), 5.66 (s, 1H), 2.05 (s, 3H). MS (ES+) m/e 366 [M+H]$^+$.

Example 15

4-(3-chloro-4-fluorophenyl)-N-1H-indazol-5-yl-6-methyl-2-oxo-1,2,3,4-tetrahydro-5-pyrimidinecarboxamide

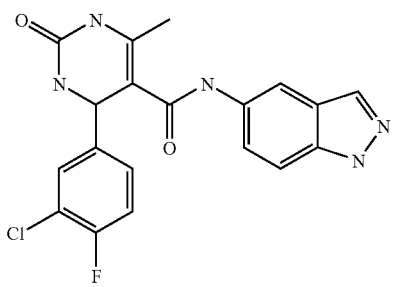

The title compound was synthesized using the procedure recited in Example 1(b), except 3-chloro-4-fluorobenzaldehyde was utilized. $^1$H NMR (400 MHz, DMSO-D6) δ ppm 12.9 (s, 1H), 9.6 (s, 1H), 8.82 (s, 1H), 8.02 (d, 2H), 7.66 (s, 1H), 7.45 (m, 4H), 7.32 (m, 1H), 5.42 (s, 1H), 2.05 (s, 3H). MS (ES+) m/e 400 [M+H]$^+$.

Example 16

4-{3-[(2-hydroxyethyl)oxy]phenyl}-N-1H-indazol-5-yl-6-methyl-2-oxo-1,2,3,4-tetrahydro-5-pyrimidinecarboxamide

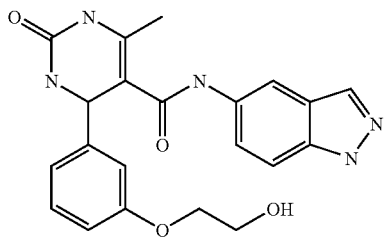

The title compound was synthesized using the procedure recited in Example 1(b), except 3-[(2-hydroxyethyl)oxy]benzaldehyde was utilized. 1H NMR (400 MHz, DMSO-D6) δ ppm 13 (s, 1H), 9.6 (s, 1H), 8.65 (s, 1H), 8.02 (d, 2H), 7.6 (s, 1H), 7.4 (s, 2H), 7.22 (t, 1H), 7.82 (m, 3H), 5.41 (s, 1H), 4.85 (t, 1H), 3.86 (t, 2H), 3.65 (t, 2H), 2.05 (s, 3H). MS (ES+) m/e 408 [M+H]$^+$.

Example 17

4-(4-bromo-2-thienyl)-N-1H-indazol-5-yl-6-methyl-2-oxo-1,2,3,4-tetrahydro-5-pyrimidinecarboxamide

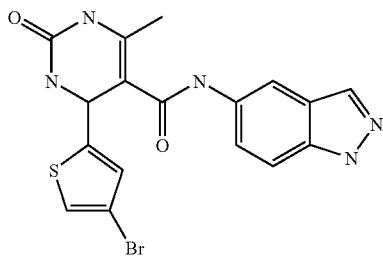

The title compound was synthesized using the procedure recited in Example 1 (b), except 4-bromo-2-thiophenecarbaldehyde was utilized. $^1$H NMR (400 MHz, DMSO-D6)$_6$ ppm 12.9 (s, 1H), 9.6 (s, 1H), 8.89 (s, 1H), 8.06 (d, 2H), 7.83 (s, 1H), 7.6(s, 1H), 7.45 (s, 2H), 6.95 (s, 1H), 5.65 (s, 1H), 2.1 (s, 3H). MS (ES+) m/e 433 [M+H]$^+$.

Example 18

4-(4-hydroxyphenyl)-N-1H-indazol-5-yl-6-methyl-2-oxo-1,2,3,4-tetrahydro-5-pyrimidinecarboxamide

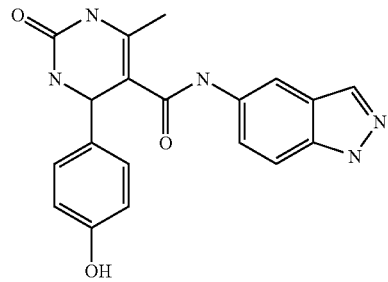

The title compound was synthesized using the procedure recited in Example 1(b), except 4-hydroxybenzaldehyde was utilized. $^1$H NMR (400 MHz, DMSO-D6) δ ppm 12.98 (s, 1H), 9.45 (s, 1H), 9.34 (s, 1H), 8.64 (s, 1H), 8.06 (d, 2H), 7.45 (d, 3H), 7.22 (d, 2H), 6.73 (d, 2H), 5.32 (s, 1H), 2.05 (s, 3H). MS (ES+) m/e 364 [M+H]$^+$.

Example 19

4-(4-chloro-2-fluorophenyl)-N-1H-indazol-5-yl-6-methyl-2-oxo-1,2,3,4-tetrahydro-5-pyrimidinecarboxamide

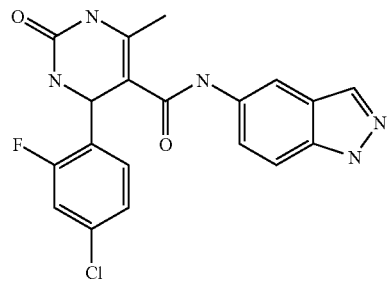

The title compound was synthesized using the procedure recited in Example 1 (b), except 2-fluoro-4-chlorobenzaldehyde was utilized. $^1$H NMR (400 MHz, DMSO-D6) δ ppm 13 (s, 1H), 9.64 (s, 1H), 8.82 (s, 1H), 8 (d, 2H), 7.57 (s, 1H), 7.4 (s, 5H), 5.61 (s, 1H), 2.02 (s, 3H). MS (ES+) m/e 400 [M+H]$^+$.

Example 20

N-1H-indazol-5-yl-6-methyl-4-{3-[(methylsulfonyl)amino]phenyl}-2-oxo-1,2,3,4-tetrahydro-5-pyrimidinecarboxamide

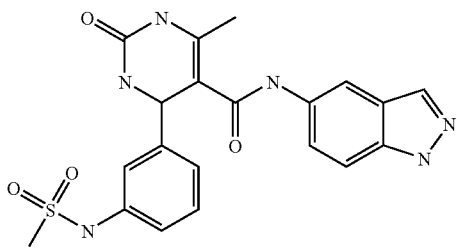

The title compound was synthesized using the procedure recited in Example 1(b), except N-(3-formylphenyl)methanesulfonamide was utilized. 1H NMR (400 MHz, DMSO-D6) δ ppm 13 (s, 1H), 9.79 (s, 1H), 9.6 (s, 1H), 8.75 (s, 1H), 8 (d, 2H), 7.6 (s, 1H), 7.43 (s, 2H), 7.3 (t, 2H), 7.2 (s, 1H), 7.08 (t, 2H), 5.41 (s, 1H), 2.9 (s, 3H), 2.05 (s, 3H). MS (ES+) m/e 441 [M+H]+.

Example 21

N-1H-indazol-5-yl-6-methyl-2-oxo-4-(6-quinoxalinyl)-1,2,3,4-tetrahydro-5-pyrimidinecarboxamide

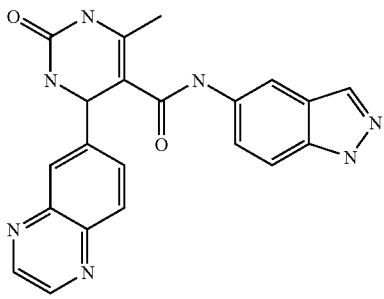

The title compound was synthesized using the procedure recited in Example 1(b), except 6-quinoxalinecarbaldehyde was utilized. $^1$H NMR (400 MHz, DMSO-D6) δ ppm 13 (s, 1H), 9.7 (s, 1H), 8.95 (d, 2H), 8.9 (s, 1H), 8.14 (d, 1H), 8.04 (s, 1H), 7.97 (d, 2H), 7.86 (m, 2H), 7.43 (s, 2H), 5.7 (s, 1H), 2.05 (s, 3H). MS (ES+) m/e 400 [M+H].

Example 22

4-[4-(aminosulfonyl)phenyl]-N-1H-indazol-5-yl-6-methyl-2-oxo-1,2,3,4-tetrahydro-5-pyrimidinecarboxamide

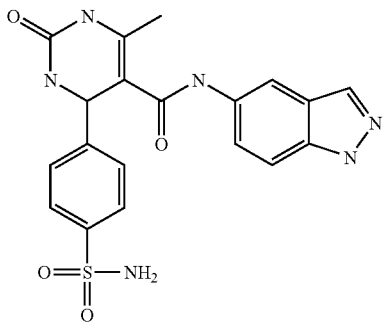

The title compound was synthesized using the procedure recited in Example 1 (b), except 4-formylbenzenesulfonamide was utilized. $^1$H NMR (400 MHz, DMSO-D6) δ ppm 13 (s, 1H), 9.65 (s, 1H), 8.82 (s, 1H), 8.02 (d, 2H), 7.82 (d, 2H), 7.69 (s, 1H), 7.46 (m, 4H), 7.32 (s, 2H), 5.5 (s, 1H), 2.05 (s, 3H). MS (ES+) m/e 427 [M+H]+.

Example 23

N-1H-indazol-5-yl-6-methyl-2-oxo-4-(2-quinolinyl)-1,2,3,4-tetrahydro-5-pyrimidinecarboxamide

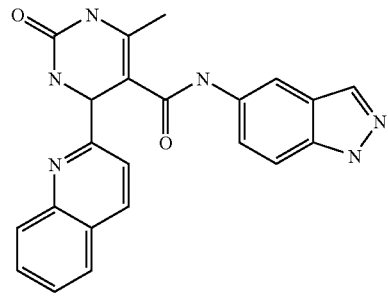

The title compound was synthesized using the procedure recited in Example 1(b), except 2-quinolinecarbaldehyde was utilized. $^1$H NMR (400 MHz, DMSO-D6) δ ppm 13 (s, 1H), 10.08 (s, 1H), 8.95 (s, 1H), 8.55 (d, 1H), 8.1 (s, 1H), 8.09 (m, 3H), 7.83 (t, 2H), 7.63 (m, 2H), 7.48 (s, 2H), 5.63 (s, 1H), 2.11 (s, 3H). MS (ES+) m/e 399 [M+H]+.

Example 24

4-[3-fluoro-4-(methyloxy)phenyl]-N-1H-indazol-5-yl-6-methyl-2-oxo-1,2,3,4-tetrahydro-5-pyrimidinecarboxamide

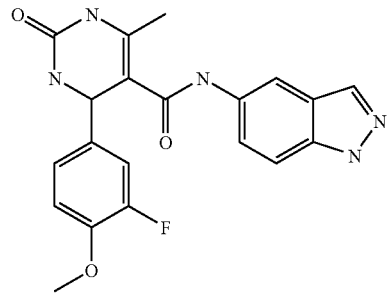

The title compound was synthesized using the procedure recited in Example 1 (b), except 3-fluoro-4-methoxybenzaldehyde was utilized. $^1$H NMR (400 MHz, DMSO-D6) δ ppm 12.96 (s, 1H), 9.59 (s, 1H), 8.74 (s, 1H), 8.03 (d, 2H), 7.59 (s, 1H), 7.44 (s, 1H), 7.29 (s, 1H), 7.13 (m, 2H), 6.95 (s, 1H), 5.39 (s, 1H), 3.82 (s, 3H), 2.1 (s, 3H). MS (ES+) m/e 396 [M+H]+.

Example 25

4-(3-cyanophenyl)-N-1H-indazol-5-yl-6-methyl-2-oxo-1,2,3,4-tetrahydro-5-pyrimidinecarboxamide

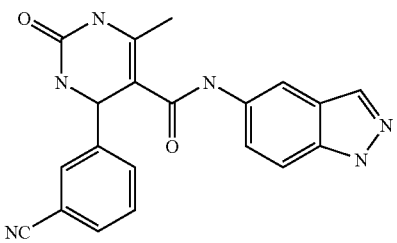

The title compound was synthesized using the procedure recited in Example 1(b), except 3-cyanobenzaldehyde was utilized. 1H NMR (400 MHz, DMSO-D6) δ ppm 12.97 (s, 1H), 9.65 (s, 1H), 8.86 (s, 1H), 8.01 (s, 2H), 7.67 (m, 5H), 7.42 (m, 2H), 5.47 (s, 1H), 2.11 (s, 3H). MS (ES+) m/e 373 [M+H]+.

Example 26

4-(1H-imidazol-1-yl)-N-1H-indazol-5-yl-6-methyl-2-oxo-1,2,3,4-tetrahydro-5-pyrimidinecarboxamide

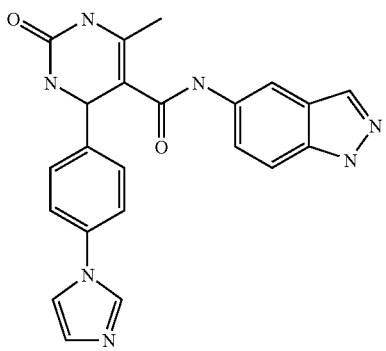

The title compound was synthesized using the procedure recited in Example 1(b), except 4-(1H-imidazol-1-yl)benzaldehyde was utilized. ¹H NMR (400 MHz, DMSO-D6) δ ppm 13 (br s, 1H), 9.68 (s, 1H), 9.63 (s, 1H), 8.85 (s, 1H), 8.26 (s, 1H), 8.07 (s, 1H), 8.01 (s, 1H), 7.91 (s, 1H), 7.78 (d, 2H), 7.74 (s, 1H), 7.56 (d, 2H), 7.46 (s, 2H), 5.55 (s, 1H), 2.13 (s, 3H). MS (ES+) m/e 414 [M+H].

Example 27

N-1H-indazol-5-yl-6-methyl-2-oxo-4-(3-quinolinyl)-1,2,3,4-tetrahydro-5-pyrimidinecarboxamide

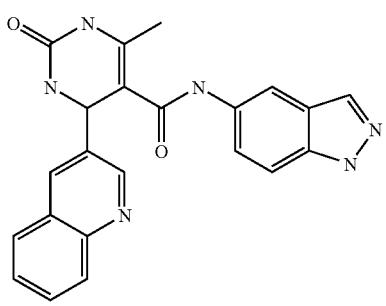

The title compound was synthesized using the procedure recited in Example 1(b), except 3-quinolinecarbaldehyde was utilized. ¹H NMR (400 MHz, DMSO-D6) δ ppm 9.73 (s, 1H), 9.05 (s, 1H), 8.97 (s, 1H), 8.47 (s, 1H), 8.15 (m, 2H), 8 (d, 2H), 7.9 (t, 1H), 7.8 (s, 1), 7.65 (t, 1H), 7,4 (m, 3H), 5.69 (s, 1H), 2.16 (s, 3H). MS (ES+) m/e 399 [M+H].

Example 28

N-1H-indazol-5-yl-6-methyl-2-oxo-4-[(E)-2-phenylethenyl]-1,2,3,4-tetrahydro-5-pyrimidinecarboxamide

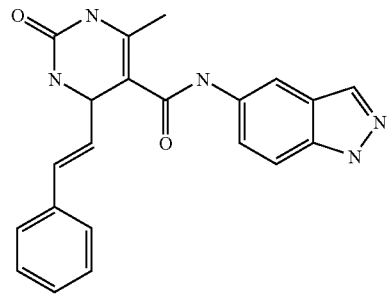

The title compound was synthesized using the procedure recited in Example 1 (b), except (2E)-3-phenyl-2-propenal was utilized. ¹H NMR (400 MHz, DMSO-D6) δ ppm 13 (br s, 1H), 9.63 (s, 1H), 8.69 (s, 1H), 8.11 (s, 1H), 8.02 (s, 1H), 7.48 (s, 1H), 7.41 (d, 2H), 7.3 (m, 5H), 6.46 (d (1H), 6.29 (d, 1H), 4.95 (s, 1H), 2.06 (s, 3H). MS (ES+) m/e 374 [M+H]+.

Example 29

N-1H-indazol-5-yl-6-methyl-2-oxo-4-[4-(trifluoromethyl)phenyl]-1,2,3,4-tetrahydro-5-pyrimidinecarboxamide

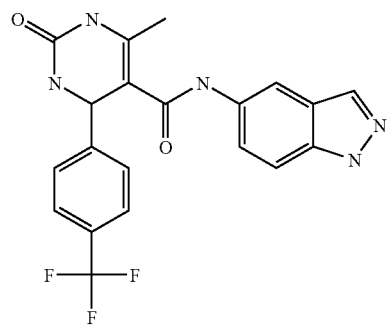

The title compound was synthesized using the procedure recited in Example 1(b), except 4-trifluoromethylbenzaldehyde was utilized. 1H NMR (400 MHz, DMSO-D6) δ ppm 13 (s, 1H), 9.65 (s, 1H), 8.82 (s, 1H), 8.04 (d, 2H), 7.76 (d, 2H), 7.7 (s, 1H), 7.54 (d, 2H), 7.44 (d, 2H), 5.52 (s, 1H), 2.05 (s, 3H). MS (ES+) m/e 416 [M+H]+.

Example 30

4-(4-chlorophenyl)-N-1H-indazol-5-yl-6-methyl-2-oxo-1,2,3,4-tetrahydro-5-pyrimidinecarboxamide

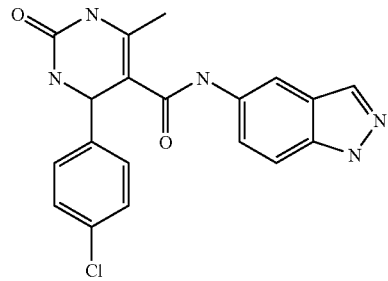

The title compound was synthesized using the procedure recited in Example 1 (b), except 4-chloro-benzaldehyde was utilized. ¹H NMR (400 MHz, DMSO-D6) δ ppm 13 (s, 1H), 9.6 (s, 1H), 8.8 (s, 1H), 8 (d, 2H), 7.6 (s, 1H), 7.4 (d, 4H), 7.3 (d, 2H), 5.4 (s, 1H), 2.05 (s, 3H). MS (ES+) m/e 382 [M+H]⁺.

Example 31

4-[4-(acetylamino)phenyl]-N-1H-indazol-5-yl-6-methyl-2-oxo-1, Z 3,4-tetrahydro-5-pyrimidinecarboxamide

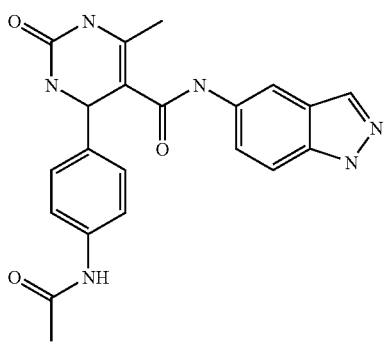

The title compound was synthesized using the procedure recited in Example 1 (b), except N-(4-formylphenyl)-acetamide was utilized. ¹H NMR (400 MHz, DMSO-D6) δ ppm 12.96 (s, 1H), 9.93 (s, 1H), 9.55 (s, 1H), 8.68 (s, 1H), 8.01 (d, 2H), 7.47 (m, 5H), 7.23 (d, 2H), 5.39 (s, 1H), 2.06 (s, 3H), 2.03 (s, 3H). MS (ES+) m/e 405 [M+H]⁺.

Example 32

4-(2-chlorophenyl)-N-1H-indazol-5-yl-6-methyl-2-oxo-1,2,3,4-tetrahydro-5-pyrimidinecarboxamide

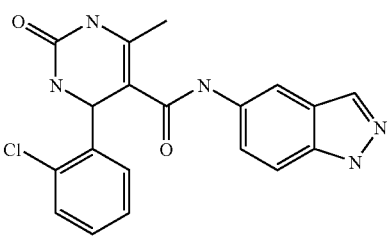

The title compound was synthesized using the procedure recited in Example 1(b), except 2-chlorobenzaldehyde was utilized. ¹H NMR (400 MHz, DMSO-D6) δ ppm 12.88 (br s, 1H), 9.7 (s, 1H), 8.78 (s, 1H), 8 (d, 2H), 7.53 (d, 2H), 7.4 (m, 4H), 7.28 (m, 1H), 5.84 (s, 1H), 2.08 (s, 3H). MS (ES+) m/e 383 [M+H]⁺.

Example 33

4-(2,3-dihydro-1,4-benzodioxin-6-yl)-N-1H-indazol-5-yl-6-methyl-2-oxo-1,2,3,4-tetrahydro-5-pyrimidinecarboxamide

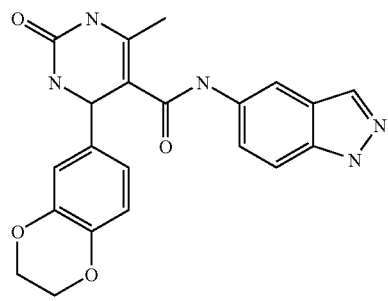

The title compound was synthesized using the procedure recited in Example 1 (b), except 2,3-dihydro-1,4-benzodioxin-6-carbaldehyde was utilized. ¹H NMR (400 MHz, DMSO-D6) δ ppm 12.97 (s, 1H), 9.56 (s, 1H), 8.68 (s, 1H), 8.03 (s, d, 2H), 7.5 (s, 1H), 7.45 (s, 2H), 6.79 (m, 3H), 5.35 (s, 1H), 4.22 (s, 3H), 2.09 (s, 3H). MS (ES+) m/e 406 [M+H]⁺.

Example 34

4-(3-hydroxyphenyl)-N-1H-indazol-5-yl-6-methyl-2-oxo-1,2,3,4-tetrahydro-5-pyrimidinecarboxamide

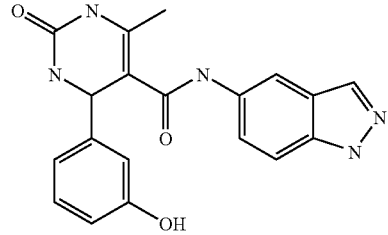

The title compound was synthesized using the procedure recited in Example 1 (b), except 3-hydroxybenzaldehyde was utilized. ¹H NMR (400 MHz, DMSO-D6) δ ppm 12.96 (s, 1H), 9.57 (s, 1H), 9.4 (s, 1H), 8.68 (s, 1H), 8.04 (d, 2H), 7.54 (s, 1H), 7.45 (s, 2H), 7.12 (t, 1H), 6.69 (m, 3H), 5.38 (s, 1H), 2.07 (s, 3H). MS (ES+) m/e 364 [M+H]⁺.

Example 35

4-(8-hydroxy-2-quinolinyl)-N-1H-indazol-5-yl-6-methyl-2-oxo-1,2,3,4-tetrahydro-5-pyrimidinecarboxamide

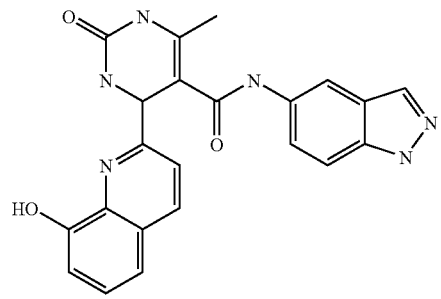

The title compound was synthesized using the procedure recited in Example 1(b), except 8-hydroxy-2-quinolinecarbaldehyde was utilized. 1H NMR (400 MHz, DMSO-D6) δ ppm 12.9 (br s, 1H), 10.21 (s, 1H), 9.89 (br s, 1H), 9.02 (s, 1H), 8.51 (d, 1H), 8.14 (s, 1H), 8 (s, 1H), 7.65 (d, 1H), 7.5 (d, 1H), 7.48 (t, 2H), 7.2 (d, 3H), 5.64 (s, 1H), 2.14 (s, 3H). MS (ES+) m/e 415 [M+H]+.

Example 36

4-[3,4-bis(methyloxy)phenyl]-N-1H-indazol-5-yl-6-methyl-2-oxo-1,2,3,4-tetrahydro-5-pyrimidinecarboxamide

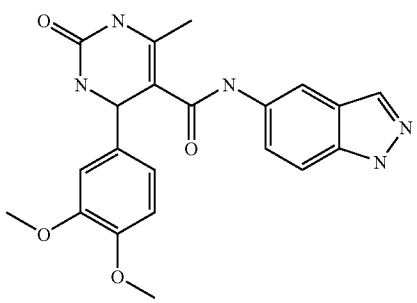

The title compound was synthesized using the procedure recited in Example 1 (b), except 3,4-dimethoxybenzaldehyde was utilized. $^1$H NMR (400 MHz, DMSO-D6) δ ppm 12.96 (s, 1H), 9.57 (s, 1H), 8.67 (s, 1H), 8.03 (d, 2H), 7.52 (s, 1H), 7.45 (s, 2H), 6.89 (m, 3H), 5.42 (s, 1H), 3.73 (s, 3H), 3.69 (s, 3H), 2.08 (s, 3H). MS (ES+) m/e 409 [M+H]+.

Example 37

4-[2-(4-chlorophenyl)ethyl]-N-1H-indazol-5-yl-6-methyl-2-oxo-1,2,3,4-tetrahydro-5-pyrimidinecarboxamide

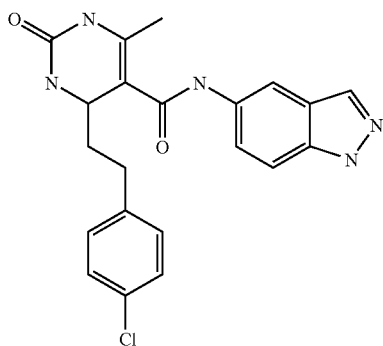

The title compound was synthesized using the procedure recited in Example 1 (b), except 3-(4-chlorophenyl)propanal was utilized. 1H NMR (400 MHz, DMSO-D6) δ ppm 12.98 (s, 1H), 9.66 (s, 1H), 8.53 (s, 1H), 8.07 (d, 2H), 7.48 (s, 2H), 7.26 (m, 5H), 4.31 (s, 1H), 2.75 (t, 2H), 2.01 (s, 3H), 1.77 (t, 2H). MS (ES+) m/e 409 [M+H]+.

Example 38

4-[3-(1H-imidazol-1-yl)phenyl]-N-1H-indazol-5-yl-6-methyl-2-oxo-1,2,3,4-tetrahydro-5-pyrimidinecarboxamide

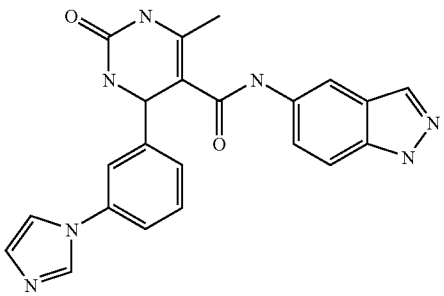

The title compound was synthesized using the procedure recited in Example 1 (b), except 3-(1H-imidazol-1-yl)benzaldehyde was utilized. $^1$H NMR (400 MHz, DMSO-D6) δ ppm 12.99 (s, 1H), 9.68 (s, 1H), 9.39 (s, 1H), 8.83 (s, 1H), 8.13 (d, 1H), 8.01 (d, 2H), 7.81 (s, 1H), 7.64 (m, 4H), 7.52 (m, 1H), 7.42 (m, 2H), 5.52 (s, 1H), 2.13 (s, 3H). MS (ES+) m/e 414 [M+H]+.

Example 39

4-(3-chlorophenyl)-N-1H-indazol-5-yl-6-methyl-2-oxo-1,2,3,4-tetrahydro-5-pyrimidinecarboxamide

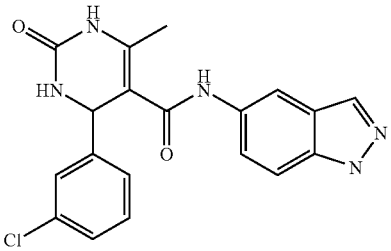

The title compound was synthesized using the procedure recited in Example 1 (b), except 4-formylbenzamide was utilized. 1H NMR (400 MHz, DMSO-D6) δ ppm 13 (s, 1H), 9.63 (s, 1H), 8.61 (s, 1H), 8.05 (d, 2H), 7.65 (s, 1H), 7.45 (m, 5H), 7.25 (d, 1H), 5.4 (s, 1H), 2.09 (s, 3H). MS (ES+) m/e 383 [M+H]+.

Example 40

4-[4-(aminocarbonyl)phenyl]-N-1H-indazol-5-yl-6-methyl-2-oxo-1,2,3,4-tetrahydro-5-pyrimidinecarboxamide

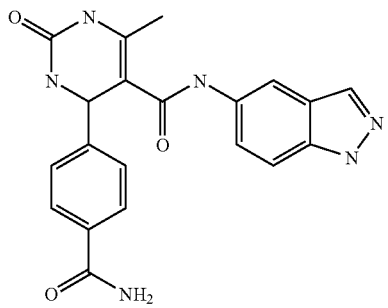

The title compound was synthesized using the procedure recited in Example 1 (b), except 4-formylbenzamide was utilized. 1H NMR (400 MHz, DMSO-D6) δ ppm 13 (s, 1H), 9.63 (s, 1H), 8.77 (s, 1H), 8.05 (d, 2H), 7.95 (d, 2H), 7.65 (s, 1H), 7.4 (m, 4H), 5.5 (s, 1H), 3.58 (s, 2H), 2.09 (s, 3H). MS (ES+) m/e 391 [M+H]+.

Example 41

N-1H-indazol-5-yl-6-methyl-2-oxo-4-phenyl-1,2,3,4-tetrahydro-5-pyrimidinecarboxamide

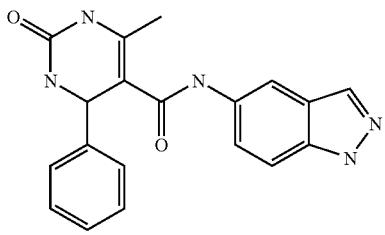

The title compound was synthesized using the procedure recited in Example 1 (b), except benzaldehyde was utilized. ¹H NMR (400 MHz, DMSO-D6) δ ppm 12.96 (s, 1H), 9.6 (s, 1H), 8.72 (s, 1H), 8.02 (d, 2H), 7.6 (s, 1H), 7.44 (s, 2H), 7.34 (m, 5H), 5.46 (s, 1H), 2.09 (s, 3H). MS (ES+) m/e 348 [M+H]+.

Example 42

N-1H-indazol-5-yl-6-methyl-2-oxo-4-(4-pyridinyl)-1,2,3,4-tetrahydro-5-pyrimidinecarboxamide

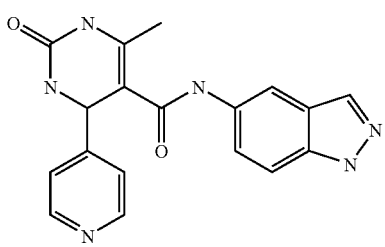

The title compound was synthesized using the procedure recited in Example 1 (b), except 4-pyridyl aldehyde was utilized. ¹H NMR (400 MHz, DMSO-D6) δ ppm 13 (s, 1H), 9.7 (s, 1H), 8.87 (s, 1H), 8.58 (d, 2H), 8.03 (d, 2H), 7.76 (s, 1H), 7.45 (m, 2H), 7.35 (d, 2H), 5.44 (s, 1H), 2.1 (s, 3H). MS (ES+) m/e 349 [M+H]+.

Example 43

Methyl 3-{5-[(1H-indazol-5-ylamino)carbonyl]-6-methyl-2-oxo-1,2,3,4-tetrahydro-4-pyrimidinyl}benzoate

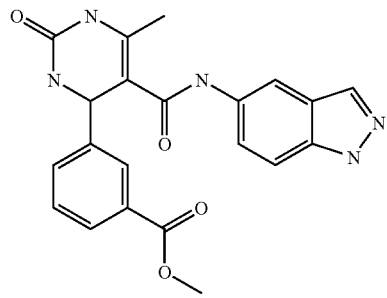

The title compound was synthesized using the procedure recited in Example 1 (b), except methyl 3-formylbenzoate was utilized. 1H NMR (400 MHz, DMSO-D6) δ ppm 12.97 (s, 1H), 9.63 (s, 1H), 8.81 (s, 1H), 7.99 (d, 3H) 7.87 (d, 1H), 7.69 (s, 1H), 7.52 (m, 4H), 5.53 (s, 1H), 3.37 (s, 3H), 2.1 (s, 3H). MS (ES+) m/e 406 [M+H]+.

Example 44

Methyl 4-{5-[(1H-indazol-5-ylamino)carbonyl]-6-methyl-2-oxo-1,2,3,4-tetrahydro-4-pyrimidinyl}benzoate

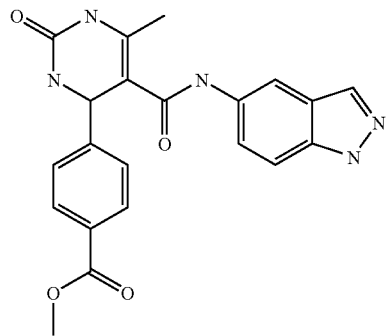

The title compound was synthesized using the procedure recited in Example 1 (b), except methyl 4-formylbenzoate was utilized. 1H NMR (400 MHz, DMSO-D6) δ ppm 12.96 (s, 1H), 9.63 (s, 1H), 8.8 (s, 1H), 7.99 (m, 4H), 7.69 (s, 1H), 7.44 (m, 4H), 5.52 (s, 1H), 3.85 (s, 3H), 2.09 (s, 3H). MS (ES+) m/e 406 [M+H]+.

Example 45

4-(3-furanyl)-N-1H-indazol-5-yl-6-methyl-2-oxo-1,2,3,4-tetrahydro-5-pyrimidinecarboxamide

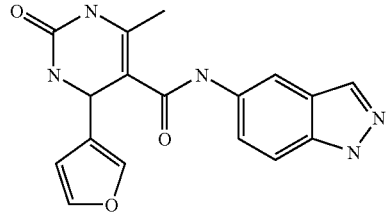

The title compound was synthesized using the procedure recited in Example 1 (b), except 3-furancarbaldehyde was utilized. 1H NMR (400 MHz, DMSO-D6) δ ppm 12.95 (br s, 1H), 9.58 (s, 1H), 8.7 (s, 1H), 8.04 (d, 2H), 7.61 (s, 1H), 7.5 (m, 4H), 6.45 (s, 1H), 5.36 (s, 1H), 2.08 (s, 3H). MS (ES+) m/e 338 [M+H]r.

Example 46

N-1H-indazol-5-yl-6-methyl-4-(2-methylpropyl)-2-oxo-1,2,3,4-tetrahydro-5-pyrimidinecarboxamide

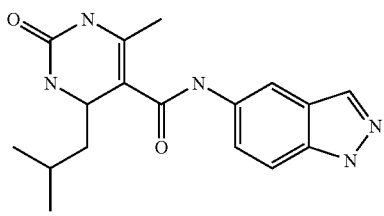

The title compound was synthesized using the procedure recited in Example 1 (b), except 3-methylbutanal was utilized. 1H NMR (400 MHz, DMSO-D6) δ ppm 13.32 (br s, 1H), 9.64 (s, 1H), 8.49 (s, 1H), 8.08 (d, 2H), 7.49 (s, 2H), 7.25 (s, 1H), 4.26 (s, 1H), 2.01 (s, 3H), 1.78 (m, 1H), 1.35 (m, 2H), 0.87 (d, 6H). MS (ES+) m/e 328 [M+H]$^+$.

Example 47

N-1H-indazol-5-yl-6-methyl-2-oxo-4-(2-phenylethyl)-1,2,3,4-tetrahydro-5-pyrimidinecarboxamide

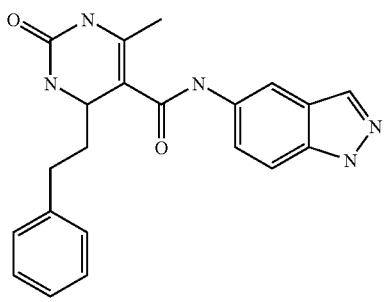

The title compound was synthesized using the procedure recited in Example 1 (b), except 3-phenylpropanal was utilized. $^1$H NMR (400 MHz, DMSO-D6) δ ppm 12.98 (s, 1H), 9.68 (s, 1H), 8.52 (s, 1H), 8.07 (d, 2H), 7.49 (s, 2H), 7.23 (m, 6H), 4.25 (s, 1H), 3.36 2.53 (t, 4H), 2.02 (s, 3H). MS (ES+) m/e 376 [M+H]$^+$.

Example 48

N-1H-indazol-5-yl-6-methyl-4-(4-nitrophenyl)-2-oxo-1,2,3,4-tetrahydro-5-pyrimidinecarboxamide

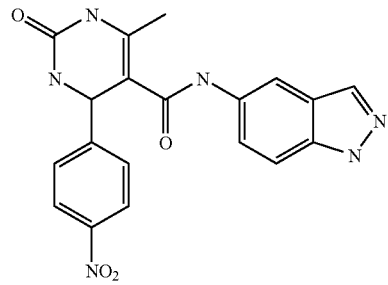

The title compound was synthesized using the procedure recited in Example 1 (b), except 4-nitrobenzaldehyde was utilized. $^1$H NMR (400 MHz, DMSO-D6) δ ppm 12.97 (s, 1H), 9.67 (s, 1H), 8.89 (s, 1H), 8.26 (d, 2H), 8.02 (d, 2H), 7.78 (s, 1H), 7.58 (d, 2H) 7.43 (m, 2H), 5.56 (s, 1H), 2.1 (s, 3H). MS (ES+) m/e 393 [M+H]$^+$.

Example 49

4-(3-cyano-4-fluorophenyl)-N-1H-indazol-5-yl-6-methyl-2-oxo-1,2,3,4-tetrahydro-5-pyrimidinecarboxamide

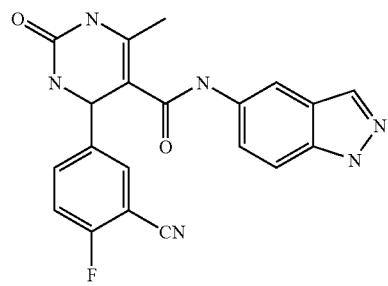

The title compound was synthesized using the procedure recited in Example 1(b), except 2-fluoro-5-formylbenzonitrile was utilized. $^1$H NMR (400 MHz, DMSO-D6) δ ppm 12.98 (s, 1H), 9.65 (s, 1H), 8.89 (s, 1H), 8.01 (s, 2H), 7.81 (d, 1H), 7.75 (m, 1H), 7.69 (s, 1H), 7.57 (t, 1H), 7.42 (m, 2H), 5.44 (s, 1H), 2.12 (s, 3H). MS (ES+) m/e 391 [M+H]$^+$.

Example 50

4-(4-fluoro-3-nitrophenyl)-N-1H-indazol-5-yl-6-methyl-2-oxo-1,2,3,4-tetrahydro-5-pyrimidinecarboxamide

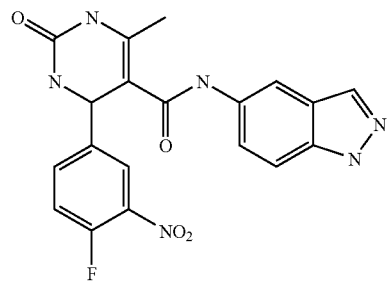

The title compound was synthesized using the procedure recited in Example 1 (b), except 4-fluoro-3-nitrobenzaldehyde was utilized. $^1$H NMR (400 MHz, DMSO-D6) δ ppm 12.98 (s, 1H), 9.67 (s, 1H), 8.93 (s, 1H), 8.05 (m, 3H), 7.75 (m, 2H), 7.63 (m, 1H), 7.42 (m, 2H), 5.51 (s, 1H), 2.13 (s, 3H). MS (ES+) m/e 411 [M+H]$^+$.

Example 51

4-[2-hydroxy-4-(methyloxy)phenyl]-N-1H-indazol-5-yl-6-methyl-2-oxo-1,2,3,4-tetrahydro-5-pyrimidinecarboxamide

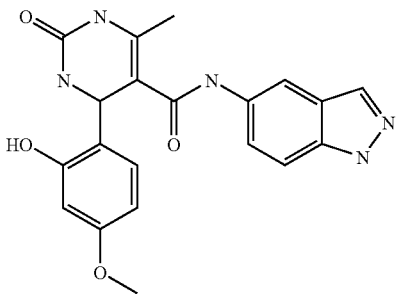

The title compound was synthesized using the procedure recited in Example 1(b), except 2-hydroxy-4-(methyloxy)benzaldehyde was utilized. $^1$H NMR (400 MHz, DMSO-D6) δ ppm 13.01 (s, 1H), 10.18 (s, 1H), 8.18 (s, 1H), 8.04 (s, 1H), 7.52 (d, 2H), 7.43 (d, 1H), 7.12 (m, 2H), 6.55 (d, 1H), 6.42 (d, 1H), 4.53 (s, 1H), 3.74 (s, 3H), 3.17 (s, 1H), 1.76 (s, 3H). MS (ES+) m/e 394 [M+H]$^+$.

Example 52

4-(4-biphenylyl)-N-1H-indazol-5-yl-6-methyl-2-oxo-1,2,3,4-tetrahydro-5-pyrimidinecarboxamide

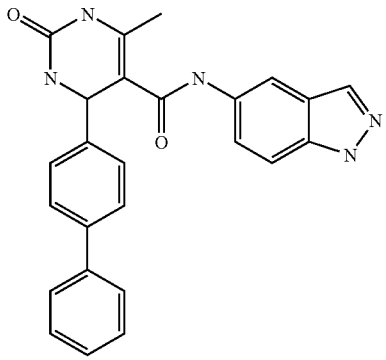

The title compound was synthesized using the procedure recited in Example 1 (b), except 4-biphenylcarbaldehyde was utilized. $^1$H NMR (400 MHz, DMSO-D6) δ ppm 12.96 (s, 1H), 9.65 (s, 1H), 8.76 (s, 1H), 8.05 (d, 2H), 7.66 (m, 5H) 7.42 (M, 7H), 5.51 (s, 1H), 2.11 (s, 3H). MS (ES+) m/e 424 [M+H]$^+$.

Example 53

4-(4-fluorophenyl)-N-1H-indazol-5-yl-6-(1-methylethyl)-2-oxo-1,2,3,4-tetrahydro-5-pyrimidinecarboxamide

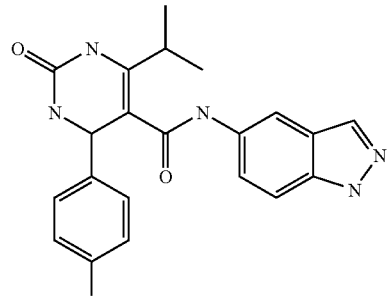

(a) N-1H-indazol-5-yl-4-methyl-3-oxopentanamide

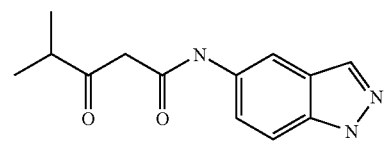

Methyl isobutyrylacetate (3 mL) was mixed with 5-aminoindazole (0.50 g) and heated In a SmithSynthesizer to 180° C. for 300 seconds. The crude mixture was then purified by silica gel chromatography to yield the title compound as a purple solid. 1H NMR (keto- tautomer) (400 MHz, DMSO-D6) δ ppm 12.98 (s, 1H), 10.06 (s, 1H), 8.11 (s, 1H), 8.02 (s, 1H), 7.48 (d, 1H), 7.38 (d, 1H), 3.62 (s, 2H), 2.78 (sept, 1H), 1.06 (d, 6H). MS m/z 246 (M+1)$^+$.

(b) 4-(4-fluorophenyl)-N-1H-indazol-5-yl-6-(1-methylethyl)-2-oxo-1,2,3,4-tetrahydro-5-pyrimidinecarboxamide

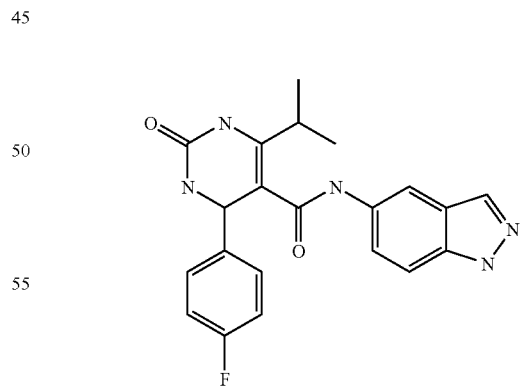

The title compound was synthesized using the procedure recited in Example 1(b), except N-1H-indazol-5-yl-4-methyl-3-oxopentanamide was utilized. NMR $^1$H NMR (400 MHz, DMSO-D6) δ ppm 13 (s, 1H), 9.8 (s, 1H), 8.5 (s, 1H), 8 (s, 2H), 7.58 (s, 1H), 7.44 (d, 1H), 7.35 (m, 3H), 7.2 (t, 2H), 5.4 (s, 1H), 3.2 (m, 1H), 1.1 (d, 3H), 1.06 (d, 3H). MS m/z 394 (M+1)$^+$.

Example 54

4-(4-fluorophenyl)-6-(2-furanyl)-N-1H-indazol-5-yl-2-oxo-1,2,3,4-tetrahydro-5-pyrimidinecarboxamide

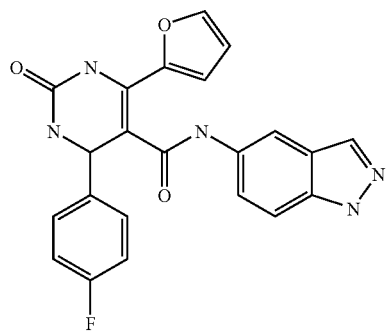

(a) 3-(2-furanyl)-N-1H-indazol-5-yl-3-oxopropanamide

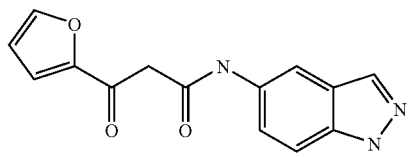

Ethyl 2-(fur-2-oyl)acetate (3 mL) was mixed with 5-aminoindazole (0.50 g) and heated in a SmithSynthesizer to 180° C. for 300 seconds. The crude mixture was then purified by silica gel chromatography to yield the title compound as a light purple solid. $^1$H NMR (keto tautomer) (400 MHz, DMSO-D6) δ ppm 12.99 (s, 1H), 10.22 (s, 1H), 8.11 (s, 1H), 8.05 (s, 1H), 8.02 (s, 1H), 7.58 (d, 1H), 7.49 (d, 1H), 7.40 (dd, 1H), 6.77 (dd, 1H), 3.96 (s, 2H). MS m/z 270 (M+1)$^+$.

(b) 4-(4-fluorophenyl)-6-(2-furanyl)-N-1H-indazol-5-yl-2-oxo-1,2,3,4-tetrahydro-5-pyrimidinecarboxamide

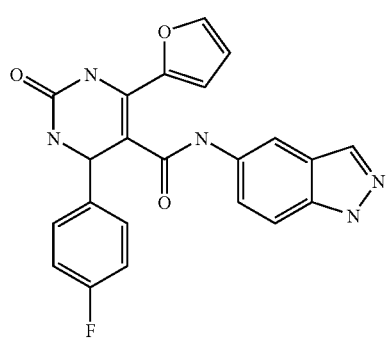

The title compound was synthesized using the procedure recited in Example 1(b), except 3-(2-furanyl)-N-1H-indazol-5-yl-3-oxopropanamide was utilized. NMR $^1$H NMR (400 MHz, DMSO-D6) δ ppm 13 (s, 1H), 9.8 (s, 1H), 8.8 (s, 1H), 8 (d, 2H), 7.7 (d, 2H), 7.4 (m, 3H), 7.2 (m, 3H), 6.95 (d, 1H), 6.5 (d, 1H), 5.3 (s, 1H). MS m/z 418 (M+)$^+$.

Example 55

4-(4-fluorophenyl)-N-1H-indazol-5-yl-1,6-dimethyl-2-oxo-1,2,3,4-tetrahydro-5-pyrimidinecarboxamide

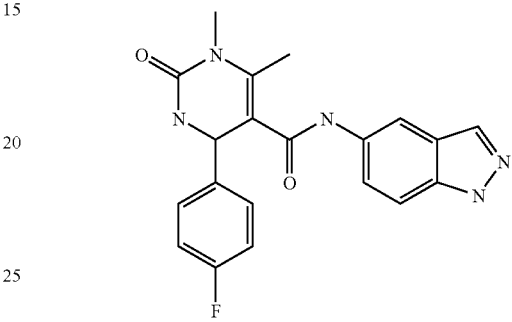

The title compound was synthesized using the procedure recited in Example 1(b), except 2.0 equivalents of N-methylurea and 1.5 equivalents of 4-fluorobenzaldehyde were used to yield 64 mg (74%). NMR $^1$H NMR (400 MHz, DMSO-D6) δ ppm 12.95 (s, 1H), 9.83 (s, 1H), 8.05 (s, 1H), 7.99 (s, 1H), 7.75 (d, 1H, 3.03 Hz), 7.42-7.44 (m, 2H), 7.29-7.33 (m, 2H), 7.14-7.19 (m, 2H), 3.09 (s, 3H), 2.19 (s, 3H). MS (ES+) m/e 380 [M+H]$^+$.

Example 56

N-1H-indazol-5-yl-1,6-dimethyl-4-(2-naphthalenyl)-2-oxo-1,2,3,4-tetrahydro-5-pyrimidinecarboxamide

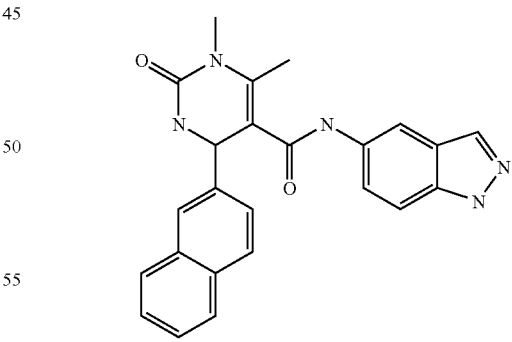

The title compound was synthesized using the procedure recited in Example 1(b), except 2.0 equivalents of N-methylurea and 1.0 equivalents of 2-naphthaldehyde were used. The title compound was triturated with CH$_2$Cl$_2$ to yield 127 mg (67%). NMR $^1$H NMR (400 MHz, DMSO-D6) δ ppm 12.94 (s, 1H), 9.87 (s, 1H), 8.04 (s, 1H), 7.97 (s, 1H), 7.82-7.91 (m, 4H), 7.72 (s, 1H), 7.41-7.50 (m, 5H), 5.49 (s, 1H), 3.13 (s, 3H), 2.21 (s, 3H). MS (ES+) m/e 412 [M+H]$^+$.

Example 57

N-1H-indazol-5-yl-6-methyl-4-(2-naphthalenyl)-2-thioxo-1,2,3,4-tetrahydro-5-pyrimidinecarboxamide

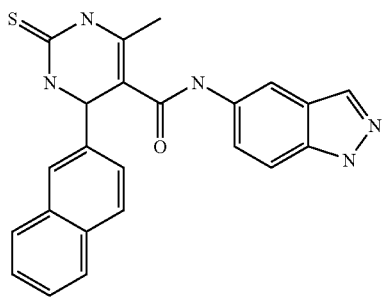

The title compound was synthesized using the procedure recited in Example 1(b), except 1.0 equivalents of 2-naphthaldehyde, 0.05 equivalents of ytterium triflate and thiourea were used. The title compound was purified by RP-HPLC (retention time 8.12 min, 0-80% $CH_3CN/H_2O/0.1\%$ TFA over 10 minutes) to yield 30 mg (32%). NMR 1H NMR (400 MHz, DMSO-D6) δ ppm 10.04 (s, 1H), 9.78 (s, 1H), 9.52 (s, 1H), 7.87-8.01 (m, 5H), 7.73 (s, 1H), 7.37-7.53 (m, 5H), 5.58-5.60 (m, 2H), 2.12 (s, 3H). MS (ES+) m/e 414 [M+H]$^+$.

Example 58

4-(4-fluorophenyl)-N-1H-indazol-5-yl-6-methyl-2-thioxo-1,2,3,4-tetrahydro-5-pyrimidinecarboxamide

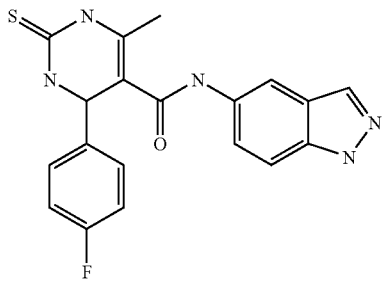

The title compound was synthesized using the procedure recited in Example 1(b), except thiourea was used in place of urea and 1.0 equivalent of 4-fluorobenzaldehyde was used to yield 650 mg (81%). NMR $^1$H NMR (400 MHz, DMSO-D6) δ ppm 10.03 (s, 1H), 9.75 (s, 1H), 9.45 (s, 1H), 8.01 (d, 2H, 12.88 Hz), 7.40-7.46 (m, 2H), 7.30-7.33 (m, 2H), 7.18-7.23 (m, 2H), 5.42 (d, 1H, 8.85 Hz), 2.10 (s, 3H). MS (ES+) m/e 382 [M+H]$^+$.

Example 59

N-1H-indazol-5-yl-6-methyl-4-(3-thienyl)-2-thioxo-1,2,3,4-tetrahydro-5-pyrimidinecarboxamide

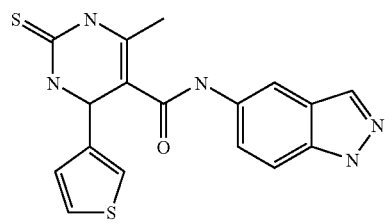

The title compound was synthesized using the procedure recited in Example 1(b), except 2.0 equivalents of thiourea, 1.5 equivalents of 3-thiophenecarboxaldehyde and 0.05 equivalents of ytterbium triflate were used. The title compound was purified by RP-HPLC (retention time 7.20 min, 0-80% $CH_3CN/H_2O/0.1\%$ TFA over 10 minutes) to yield 2 mg (1%). NMR $^1$H NMR (400 MHz, DMSO-D6) δ ppm 10.00 (s, 1H), 9.75 (s, 1H), 9.49 (s, 1H), 8.06 (s, 1H), 8.00 (s, 1H), 7.52-7.54 (m, 1H), 7.42-7.47 (m, 2H), 7.29 (d, 1H, 2.53 Hz), 7.06 (dd, 1H, 1.26 Hz, 5.05 Hz), 5.45 (d, 1H, 3.03 Hz), 2.10 (s, 3H). MS (ES+) m/e 370 [M+H]$^+$.

Example 60

4-(4-fluorophenyl)-N-1H-indazol-5-yl-1,3,6-trimethyl-2-oxo-1,2,3,4-tetrahydro-5-pyrimidinecarboxamide

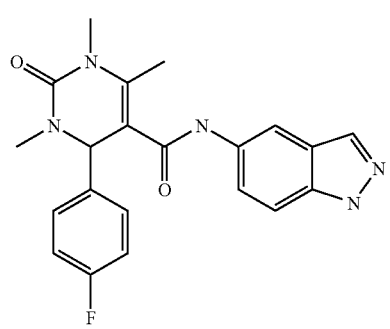

The title compound was synthesized using the procedure recited in Example 1(b), except N,N'-dimethylurea was used in place of urea, 1.0 equivalent of 4-fluorobenzaldehyde was used, and 0.05 equivalents of ytterbium triflate were used.

The title compound was purified by RP-HPLC (retention time 7.69 min, 0-80% $CH_3CN/H_2O/0.1\%$ TFA over 10 minutes) to yield 14 mg (8%). NMR $^1$H NMR (400 MHz, DMSO-D6) δ ppm 9.82 (s, 1H), 8.05 (s, 1H), 8.00 (s, 1H), 7.39-7.47 (m, 2H), 7.17-7.27 (m, 4H), 5.34 (s, 1H), 3.15 (s, 3H), 2.79 (s, 3H), 2.17 (s, 3H). MS (ES+) m/e 394 [M+H]$^+$.

Example 61

4-(4-fluorophenyl)-N-1H-indazol-5-yl-6-methyl-2-oxo-1-(phenylmethyl)-1,2,3,4-tetrahydro-5-pyrimidinecarboxamide

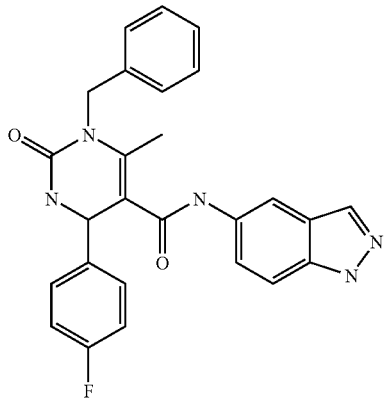

The title compound was synthesized using the procedure recited in Example 1(b), except N-benzylurea was used in place of urea, 1.0 equivalent of 4-fluorobenzaldehyde were used, and 0.05 equivalents of ytterbium triflate was used.

The title compound was purified by RP-HPLC (retention time 8.69 min, 0-80% CH$_3$CN/H$_2$O/0.1% TFA over 10 minutes) to yield 37 mg (18%). NMR $^1$H NMR (400 MHz, DMSO-D6) δ ppm 9.91 (s, 1H), 7.99-8.01 (m, 2H), 7.92 (d, 1H, 2.77 Hz), 7.32-7.45 (m, 5H), 7.24-7.28 (m, 1H), 7.15-7.20 (m, 4H), 5.39 (s, 1H), 5.04 (d, 1H, 16.93 Hz), 4.81 (d, 1H, 16.68 Hz), 2.09 (s, 3H), 1.25 (s, 1H), 0.45-0.88 (m, 1H). MS (ES+) m/e 456 [M+H]$^+$.

Example 62

2-amino-4-(4-fluorophenyl)-N-1H-indazol-5-yl-6-methyl-1,4-dihydro-5-pyrimidinecarboxamide

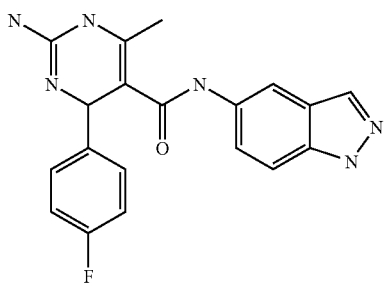

(a) Preparation of title compound: Guanidine hydrochloride (48 mg, 1.2 equiv), p-fluorobenzaldehyde (52 mg, 1.0 equiv), N-1H-indazol-5-yl-3-oxobutanamide (Example 1(a), 100 mg, 1.1 equiv), and sodium bicarbonate (141 mg, 4.0 equiv) were combined in DMF (1 mL) and heated to 70° C. in a sealed tube for three hours. The residue was poured onto ice (2 mL), diluted with ether (2 mL) and the product was collected by filtration. The solid was washed with water and ether and air dried. The title compound was purified further by RP-HPLC (retention time 5.99 min, 0-80% CH$_3$CN/H$_2$O/ 0.1% TFA over 10 minutes) to yield 9 mg (6%). NMR $^1$H NMR (400 MHz, DMSO-D6) δ ppm 10.30 (s, 1H), 9.91 (s, 1H), 9.19 (s, 1H), 8.01 (s, 2H), 7.68 (s, 2H), 7.45 (d, 1H, 0.51 Hz), 7.38-7.40 (m, 3H), 7.23-7.27 (m, 2H), 5.62 (s, 1H), 2.15 (s, 3H). MS (ES+) m/e 385 [M+H]$^+$.

Example 63

4-(4-fluorophenyl)-N-1H-indazol-5-yl-2,6-dimethyl-1,4-dihydro-5-pyrimidinecarboxamide

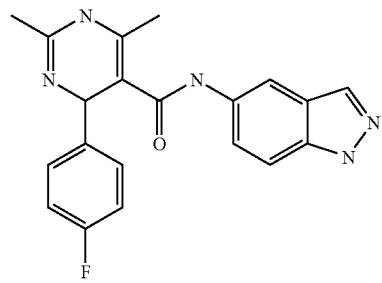

The title compound was synthesized using the procedure recited in Example 62 (a), except acetamidine hydrochloride was used in place of guanidine hydrochloride. The title compound was purified further by RP-HPLC (retention time 5.25 min, 0-80% CH$_3$CN/H$_2$O/0.1% TFA over 10 minutes) to yield 26 mg (17%). NMR $^1$H NMR (400 MHz, DMSO-D6) δ ppm 11.26 (s, 1H), 11.07 (s, 1H), 9.99 (s, 1H), 8.01 (d, 1H, 1.01 Hz), 7.96 (s, 1H), 7.45-7.53 (m, 3H), 7.26-7.33 (m, 3H), 5.86 (s, 1H), 2.30 (s, 3H), 2.12 (s, 3H). MS (ES+) m/e 364 [M+H]$^+$.

Example 64

4-(4-fluorophenyl)-N-1H-indazol-5-yl-N,6-dimethyl-2-oxo-1,2,3,4-tetrahydro-5-pyrimidinecarboxamide

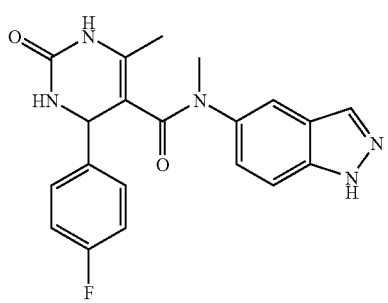

a) ethyl 1H-indazol-5-ylcarbamate

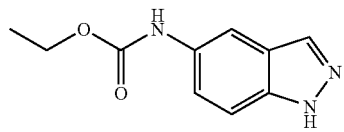

5-aminoindazole (3.0 g, 22.6 mmol, 1 equiv) was dissolved in pyridine (20 mL). The solution was cooled to 0° C., and ethyl chloroformate (2.27 mL, 23.7 mmol, 1.05 equiv) was added. After 45 minutes, the reaction was quenched with water, and diluted with ethyl acetate. The layers were separated, and the organic layer was washed with 1N HCl (2×), satd. NaCl (1×). The organic layer was dried over $Na_2SO_4$, filtered and concentrated. Trituration of the residue with $CH_2Cl_2$/hexanes afforded an off-white powder (1.19 g, 26%). $^1$H NMR (400 MHz, DMSO-D6) δ ppm 12.92 (s, 1H), 9.54 (s, 1H), 7.99 (s, 1H), 7.88 (s, 1H), 7.45 (d, J=8.8 Hz, 1H), 7.37 (dd, J=1.8, 9.1 Hz, 1H), 4.13 (q, J=7.1 Hz, 1H), 1.26 (t, J=7.3 Hz, 1H) MS (ES+) m/e 206 [M+H]$^+$.

(b) N-methyl-1H-indazol-5-amine

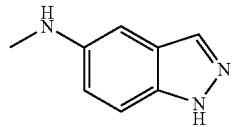

The product of Example 50(a) (1.19 g, 5.8 mmol, 1 equiv) was dissolved in THF (23 mL) and cooled to 0° C. Lithium aluminum hydride (11.6 mL of a 1M solution in THF, 11.6 mmol, 2 equiv) was added slowly (gas evolved!) The reaction was warmed to room temperature over 20 minutes, then heated to reflux for 2.5 hours. The mixture was cooled to room temperature and quenched with a 1:1 mixture of $Na_2SO_4.12H_2O$:celite. The resulting slurry was filtered and the solids were washed with methanol. The product was purified by trituration with $CH_2Cl_2$/hexanes to provide the product as a white powdery solid (0.350 g, 41%). $^1$H NMR (400 MHz, DMSO-D6) δ ppm 12.57 (br s, 1H), 7.76 (d, J=0.7 Hz, 1H), 7.27 (d, J=8.9 Hz, 1H), 6.79 (dd, J=2.3, 8.8 Hz, 1H), 6.56 (d, J=1.7 Hz, 1H), 5.38 (q, J=5.3 Hz, 1H), 2.69 (d, J=5.3 Hz, 3H) MS (ES+) m/e 148 [M+H]$^+$.

(c) N-1H-indazol-5-yl-N-methyl-3-oxobutanamide

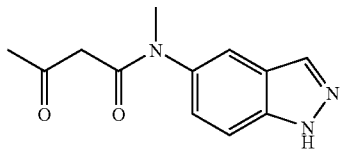

The product of Example 52(b) (350 mg, 2.38 mmol, 1 equiv) was dissolved in acetonitrile (1.5 mL). Diketene (0.183 mL, 2.38 mmol, 1 equiv) was added in a single portion. The reaction was sealed and heated to 50° C. for 2 hours. The mixture was cooled to room temperature and concentrated to a pale brown foam, which was sufficiently pure for use in the subsequent reaction (549 mg, 100%). $^1$H NMR (400 MHz, DMSO-D6) δ ppm 13.25 (br s, 1H), 8.12 (s, 1H), 7.77 (d, J=1.5 Hz, 1H), 7.60 (d, J=8.8 Hz, 1H), 7.26 (dd, J=1.7, 8.5 Hz, 1H), 3.26 (s, 2H), 3.20 (s, 3H), 1.96 (s, 3H) MS (ES+) m/e 231 [M+H]$^+$.

(d) 4-(4-fluorophenyl)-N-1H-indazol-5-yl-N,6-dimethyl-2-oxo-1,2,3,4-tetrahydro-5-pyrimidinecarboxamide

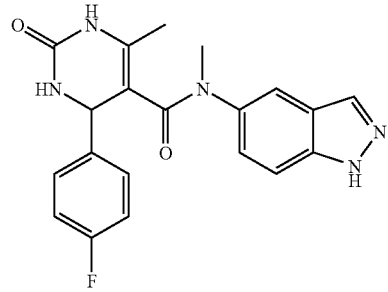

The title compound was synthesized using the procedure recited in Example 1(b), except N-1H-indazol-5-yl-N-methyl-3-oxobutanamide was utilized. 1H NMR (400 MHz, $CDCl_3$) δ ppm 13.25 (br s, 1H), 8.02 (s, 1H), 7.44 (d, J=8.8 Hz, 1H), 7.26 (m, 2H), 7.11 (t, J=8.5 Hz, 2H), 7.05 (br s, 1H), 6.94 (dd, J=1.7, 8.6 Hz, 1H), 6.07 (s, 1H), 5.09 (s, 1H), 4.93 (s, 1H), 3.24 (s, 3H), 1.90 (s, 3H) MS (ES+) m/e 380 [M+H]$^+$.

Example 65

4-(4-fluorophenyl)-N-1H-indazol-5-yl-2-oxo-1,2,3,4-tetrahydro-5-pyrimidinecarboxamide

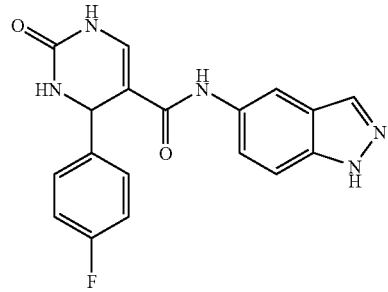

(b) methyl 4-(4-fluorophenyl)-2-oxo-1,2,3,4-tetrahydro-5-pyrimidinecarboxylate

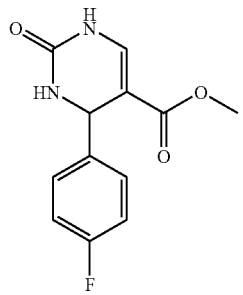

A round bottom flask was charged with 4-fluorobenzaldehyde (2.00 mL, 18.6 mmol, 1 equiv), methyl 3,3-dimethoxypropionate (2.49 mL, 18.6 mmol, 1 equiv), urea (1.68 g, 28.0 mmol, 1.5 equiv), and copper (I) chloride (184 mg, 1.86 mmol, 0.1 equiv). THF (18.6 mL) was added, followed by acetic acid (0.110 mL, 1.86 mmol, 0.1 equiv) and BF$_3$.OEt$_2$ (3.07 mL, 24.2 mmol, 1.3 equiv). The slurry was heated to reflux for 24 hours, then stirred at room temperature for an additional 36 hours. The mixture was diluted with water and carefully neutralized with satd. NaHCO$_3$. Ethyl acetate was added, and the biphasic solution was filtered through celite. The layers were separated, and the aqueous layer was washed with an additional portion of ethyl acetate. The combined organic extracts were washed with satd. NaCl, dried over Na$_2$SO$_4$, filtered and concentrated to a foamy solid. The residue was purified by flash chromatography (50% Ch$_2$Cl$_2$/ethyl acetate) to provide 535 mg of the product as an off-white powder (535 mg, 11%). NMR $^1$H NMR (400 MHz, DMSO-D6) δ ppm 9.25 (d, J=5 Hz, 1H), 7.72 (br s, 1H), 7.30-7.26 (m, 3H), 7.17 (t, J=8.9 Hz, 2H), 5.14 (d, J=3 Hz, 1H), 3.56 (s, 3H) MS m/z 251 [M+H]+

(b) 4-(4-fluorophenyl)-2-oxo-1,2,3,4-tetrahydro-5-pyrimidinecarboxylic acid

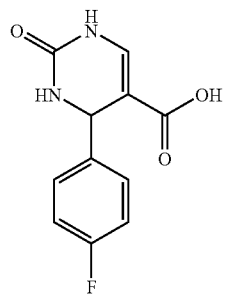

The product of from Step A above (360 mg, 1.44 mmol, 1 equiv) was suspended in methanol (6.75 mL) and 2.5 M NaOH (2.25 mL) was added. The solution was heated to 60° C. for 6 hours, then cooled to room temperature and stirred for 18 hours. The reaction was diluted with ethyl acetate and water. The mixture was separated, and the pH of the aqueous layer was adjusted to 2 with 6N HCl. The acidified aqueous layer was extracted with ethyl acetate (2×). The combined organic layers were dried over Na$_2$SO$_4$, filtered, and concentrated. The residue was azeotroped several times with hexane to provide a pale yellow powder which was essentially pure (290 mg, 85%) NMR $^1$H NMR (400 MHz, DMSO-D6) δ ppm 11.9 (br s, 1H), 9.11 (dd, J=1.7, 5.8 Hz, 1H), 7.65 (br t, J=2 Hz, 1H), 7.30 (dd, J=5.6, 8.9 Hz, 2H), 7.23(d, J=5.8 Hz, 1H), 7.18 (t, J=8.8 Hz, 2H), 5.10 (d, J=2.8 Hz, 1H), 1 MS m/z 236 [M+H]$^+$ (c) 4-(4-fluorophenyl)-N-1H-indazol-5-yl-2-oxo-1,2,3,4-tetrahydro-5-pyrimidinecarboxamide

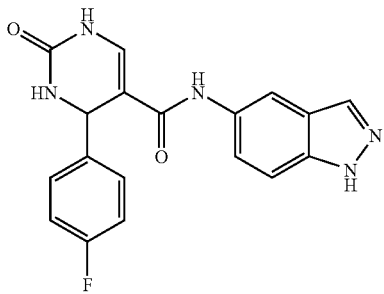

The product of Step b above (258 mg, 1.09 mmol, 1 equiv) was combined with 5-aminoindazole (303 mg, 2.28 mmol, 1.2 equiv) and EDC (437 mg, 2.28 mmol, 1.2 equiv) in a round bottom flask. DMF (4.5 mL) was added, followed by DMAP (30 mg) and triethylamine (0.318 mL, 2.28 mmol, 1.2 equiv). The reaction mixture was heated to 80° C. for 2 hours. The reaction was cooled to room temperature and poured into a separatory funnel containing ethyl acetate and water. The layers were separated, and the organic layer was washed with 1M HCl (2×), satd. NaHCO$_3$ (1×), and satd. NaCl (1×). The organic extracts were dried over Na2SO4, filtered and concentrated to a yellow solid. One-fourth of the residue was further purified by reverse-phase HPLC (0-80% CH$_3$CN/H$_2$O/0.1% TFA over 10 minutes, retention time 6.26 min) to provide 9 mg of the product as a colorless solid. NMR $^1$H NMR (400 MHz, DMSO-D6) 5 ppm 12.92 (br s, 1H), 9.56 (s, 1H), 9.12 (dd, J=1.6, 5.9 Hz, 1H), 8.04 (t, J=1.3 Hz, 1H), 7.97 (s, 1H), 7.43 (d, J=1.3 Hz, 2H), 7.40 (d, J=5.8 Hz, 1H), 7.34 (m, 2H), 7.17 (t, J=9.1 Hz, 2H), 5.45 (d, J=3.1 Hz, 1H) MS m/z 352 [M+H]+

Example 66

1-ethyl-4-(4-fluorophenyl)-N-1H-indazol-5-yl-6-methyl-2-oxo-1,2,3,4-tetrahydro-5-pyrimidinecarboxamide

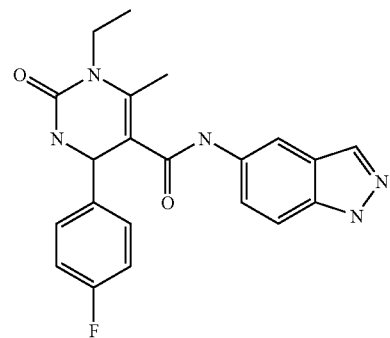

The title compound was synthesized using the procedure recited in Example 1 (b), except 2.0 equivalents of N-ethylurea was used in place of urea, and 1.2 equivalents of p-fluorobenzaldehyde was used to yield 5 mg (3%). NMR $^1$H NMR (400 MHz, DMSO-D6) δ ppm 12.97 (s, 1H), 9.83 (s, 1H), 8.02 (d, 2H, 18.7 Hz), 6.65 (d, 1H, 3.03 Hz), 7.39-7.46 (m, 2H), 7.29-7.32 (m, 1H), 7.15-7.19 (m, 2H), 6.54 (s, 1H), 5.27 (s, 1H), 3.76-3.81 (m, 1H), 3.52-3.55 (m, 1H), 2.19 (s, 3H), 1.11 (t, 3H, 6.82 Hz). MS (ES+) m/e 394 [M+H]$^+$.

Example 67

N-(3-amino-1H-indazol-5-yl)-4-(4-fluorophenyl)-6-methyl-2-oxo-1,2,3,4-tetrahydro-5-pyrimidinecarboxamide

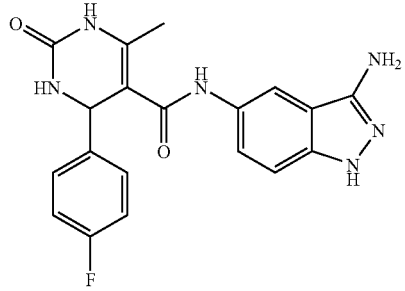

(a) 5-nitro-1H-indazol-3-amine

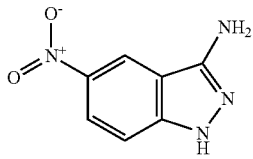

Hydrazine monohydrate (2.1 mL, 44 mmol) was added to a solution of 2-chloro-5-nitrobenzonitrile (7.30 g, 40 mmol) in pyridine (30 mL) and the mixture was heated to reflux overnight. The dark red solution was then cooled, poured into H$_2$O and the resulting solid filtered and dried to give the title compound as a dark red powder (5.7 g, 80%). NMR $^1$H NMR (400 MHz, DMSO-D6) δ ppm 8.95 (d, J=2.0, 1H), 8.06 (dd, J=9.2, 2.0, 1H), 7.34 (d, J=9.2, 1H), 5.98 (br s, 2H) MS m/z 179.0 [M+H]$^+$ (b) N-(1-acetyl-5-nitro-1H-indazol-3-yl)acetamide

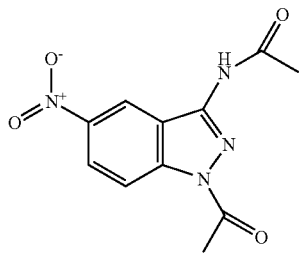

The product from Step (a) above (3.6 g, 20.2 mmol) was dissolved in pyridine (30 mL), acetic anhydride (4.15 mL, 44 mmol) was added and the mixture was stirred overnight at rt. The red solution was pouted into H$_2$O and the resulting solid was filtered to give the title compunt as a red solid (4.8 g, 91%). NMR $^1$H NMR (400 MHz, DMSO-D6) δ 11.21 (br s, 1H), 9.08 (s, 1H), 8.46 (s, 2H), 2.51 (s, 3H), 2.23 (s, 3H) (MS m/z 263.2.0 [M+H]$^+$ (c) N-(1-acetyl-5-amino-1H-indazol-3-yl)acetamide

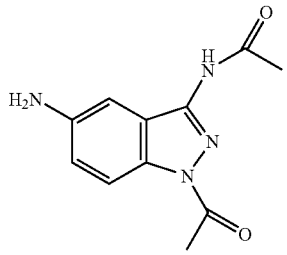

The product from Step (b) above (3.0 g, 11.4 mmol) and 5% Pd/C (1 g) were combined in MeOH (40 mL) and hydrogenated uner a balloon of H$_2$ for 3 h. The mixture was filtered through Celite and the filtrate was concentrated to give the title compound as a dark solid (2.6 g, 98%). NMR $^1$H NMR (400 MHz, DMSO-D6) δ 10.62 (s, 1H), 7.97 (dd, J=7.9, 1.8, 1H), 6.93-6.89 (m, 2H), 5.26 (s, 2H), 2.52 (s, 3H), 2.08 (s, 3H) (MS m/z 233.2 [M+H]$^+$ (d) N-[1-acetyl-3-(acetylamino)-1H-indazol-5-yl]-3-oxobutanamide

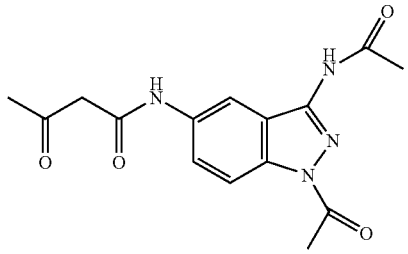

The product from Step (c) above (2.6 g, 11.4 mmol) was dissolved in acetonitrile (20 mL) and diketene (0.86 mL, 11.2 mmol) was added in portions over min, then the solution was sealed and heated to 50° C. overnight. The reaction mixture was then cooled, filtered and the filtrate was concentrated to give the title compound as a dark tan solid (2.6 g, 73%). NMR $^1$H NMR (400 MHz, DMSO-D6) δ 10.86 (s, 1H), 10.32 (s, 1H), 8.25-8.20 (m, 2H), 7.75 (dd, J=8.9, 2.0, 1H), 3.59 (s, 2H), 2.63 (s, 3H), 2.22 (s, 3H), 3.18 (s, 3H) MS m/z 317.0 [M+H]$^+$ (d) N-(3-amino-1H-indazol-5-yl)-4-(4-fluorophenyl)-6-methyl-2-oxo-1,2,3,4-tetrahydro-5-pyrimidinecarboxamide

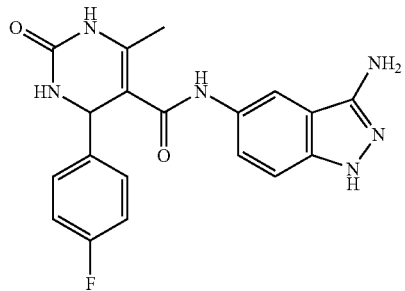

The product from Step (d) above (1.35 g, 4.2 mmol) was treated as in Example 1b, Method B, except that heating was continued overnight. The reaction mixture was concentrated to give a mixture of bis-acetyl and mono-acetyl. The crude solid was dissolved in THF (15 mL) and 6M aq. HCl (5 mL) was added and the mixture was heated to reflux for 3 h. The reaction mixture was cooled, concentrated and the residue poured into sat. aq. K$_2$CO$_3$ and extracted with EtOAc/THF. The organic extracts were washed with brine, dried (MgSO$_4$), filtered and the filtrate was concentrated to give a solid, a portion of which was purified by reverse-phase HPLC to give the title compound as a tan solid. (NMR $^1$H NMR (400 MHz, MeOD) δ (8.28 (s, 1H), 7.53 (dd, J=9.1, 2.0), 7.43-7.39 (m, 3H), 7.11-7.06 (m, 3H), 5.54 (s, 1H), 3.33 (s, 3H), MS m/z 381.3 [M+H]+

Example 68

4-(1-benzofuran-2-yl)-N-1H-indazol-5-yl-6-methyl-2-oxo-1,2,3,4-tetrahydro-5-pyrimidinecarboxamide

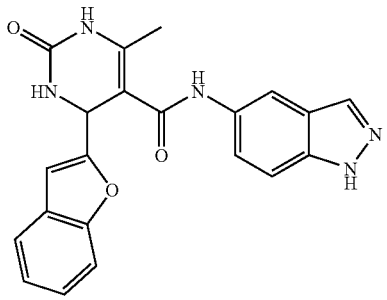

The title compound was synthesized using the procedure recited in Example 1(b), except benzo[b]furan-2-carboxaldehyde was utilized. MS (ES+) m/z 388 [M+H]$^+$.

Example 69

4-[(E)-2-(2-furanyl)ethenyl]-N-1H-indazol-5-yl-6-methyl-2-oxo-1,2,3,4-tetrahydro-5-pyrimidinecarboxamide

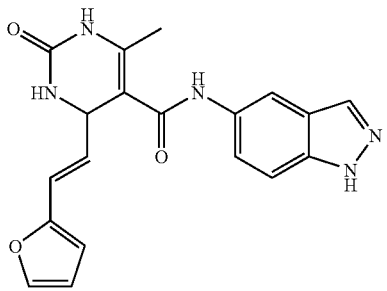

The title compound was synthesized using the procedure recited in Example 1(b), except 3-(2-furyl)acrolein was utilized. Purified on reverse phase HPLC (xterra column) 10-99 ACN/H$_2$O (0.1% TFA) over 15 min. MS (ES+) m/z 364 [M+H]$^+$.

Example 70

N-1H-indazol-5-yl-6-methyl-4-(5-methyl-2-furanyl)-2-oxo-1,2,3,4-tetrahydro-5-pyrimidinecarboxamide

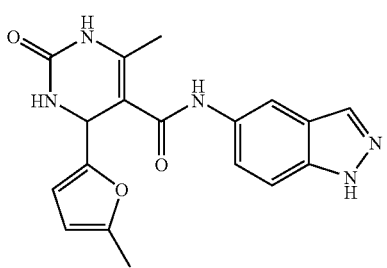

The title compound was synthesized using the procedure recited in Example 1(b), except 5-methylfurfural was utilized. MS (ES+) m/z 352 [M+H]$^+$.

Example 71

4-[5-(4-chlorophenyl)-2-furanyl]-N-1H-indazol-5-yl-6-methyl-2-oxo-1,2,3,4-tetrahydro-5-pyrimidinecarboxamide

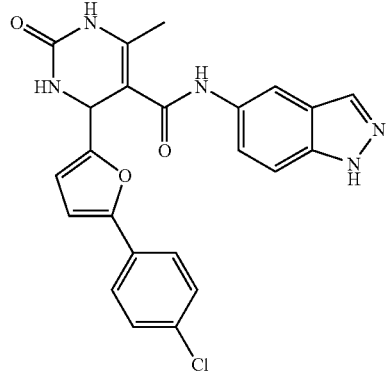

The title compound was synthesized using the procedure recited in Example 1(b), except 5-(4-chlorophenyl)-2-furaldehyde was utilized. MS (ES+) m/z 448 [M+H]$^+$.

Example 72

4-(1,3-benzodioxol-5-yl)-N-1H-indazol-5-yl-6-methyl-2-oxo-1,2,3,4-tetrahydro-5-pyrimidinecarboxamide

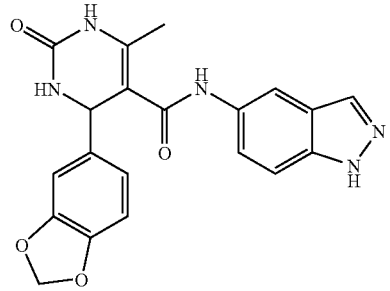

The title compound was synthesized using the procedure recited in Example 1(b), except piperonal was utilized. MS (ES+) m/z 392 [M+H]$^+$.

Example 73

N-1H-indazol-5-yl-6-methyl-2-oxo-4-[4-(phenyloxy)phenyl]-1,2,3,4-tetrahydro-5-pyrimidinecarboxamide

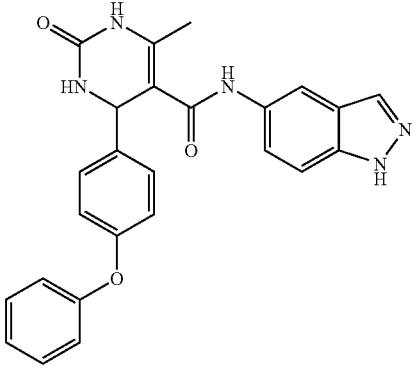

The title compound was synthesized using the procedure recited in Example 1(b), except 4-phenoxybenzaldehyde was utilized. MS (ES+) m/z 440 [M+H]$^+$.

Example 74

N-1H-indazol-5-yl-6-methyl-2-oxo-4-[3-(phenyloxy)phenyl]-1,2,3,4-tetrahydro-5-pyrimidinecarboxamide

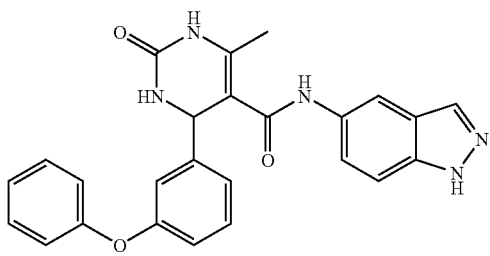

The title compound was synthesized using the procedure recited in Example 1(b), except 3-phenoxybenzaldehyde was utilized. MS (ES+) m/z 440 [M+H]$^+$.

Example 75

N-1H-indazol-5-yl-6-methyl-2-oxo-4-(5-quinolinyl)-1,2,3,4-tetrahydro-5-pyrimidinecarboxamide

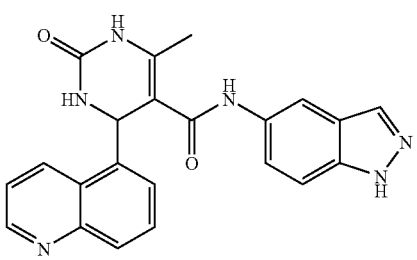

The title compound was synthesized using the procedure recited in Example 1(b), except quinoline-5-carboxaldehyde was utilized. MS (ES+) m/z 400 [M+H]$^+$.

Example 76

4-(3-Bromophenyl)-N-1H-indazol-5-yl-6-methyl-2-oxo-1,2,3,4-tetrahydro-5-pyrimidinecarboxamide

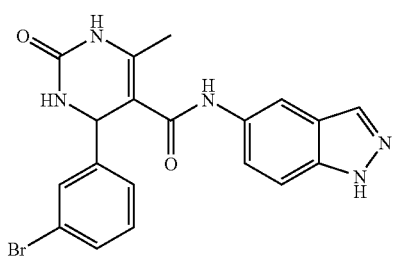

The title compound was synthesized using the procedure recited in Example 1, except 3-bromobenzaldehyde was utilized. Filtration afforded the title compound as a pale grey solid which required no additional purification. MS m/e 427 [M+H]$^+$.

Example 77

N-1H-indazol-5-yl-6-methyl-2-oxo-4-(5-phenyl-2-thienyl)-1,2,3,4-tetrahydro-5-pyrimidinecarboxamide

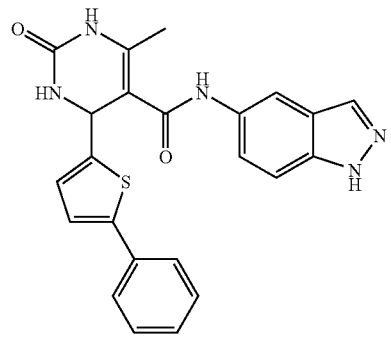

The title compound was synthesized using the procedure recited in Example 1(b), except 5-phenyl-2-thiophenecarbaldehyde was utilized. MS (ES+) m/z 430 [M+H]$^+$.

Example 78

N-1H-indazol-5-yl-6-methyl-4-[(E)-2-(2-nitrophenyl)ethenyl]-2-oxo-1,2,3,4-tetrahydro-5-pyrimidinecarboxamide

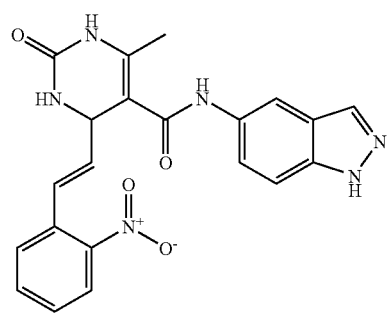

The title compound was synthesized using the procedure recited in Example 1(b), except (2E)-3-(2-nitrophenyl)-2-propenal was utilized. The title compound was purified by reverse phase HPLC (xterra column, 10-99 CH$_3$CN/H$_2$O (0.1% TFA) over 15 min) MS (ES+) m/z 419 [M+H]$^+$.

Example 79

N-1H-indazol-5-yl-6-methyl-4-{(E)-2-[4-(methyloxy)phenyl]ethenyl}-2-oxo-1,2,3,4-tetrahydro-5-pyrimidinecarboxamide

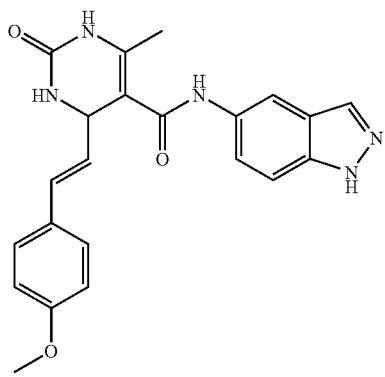

The title compound was synthesized using the procedure recited in Example 1(b), except (2E)-3-[4-(methyloxy)phenyl]-2-propenal was utilized. MS (ES+) m/z 404 [M+H]⁺.

Example 80

4-(1-cyclohexen-1-yl)-N-1H-indazol-5-yl-6-methyl-2-oxo-1,2,3,4-tetrahydro-5-pyrimidinecarboxamide

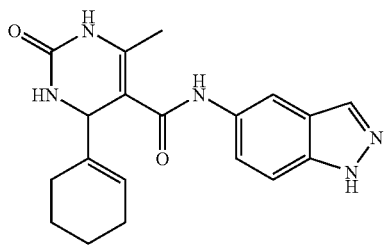

The title compound was synthesized using the procedure recited in Example 1(b), except 2-cyclohexene-1-carbaldehyde was utilized. MS (ES+) m/z 352 [M+H]⁺.

Example 81

N-1H-indazol-5-yl-6-methyl-4-{(E)-2-[2-(methyloxy)phenyl]ethenyl}-2-oxo-, 1,2,3,4-tetrahydro-5-pyrimidinecarboxamide

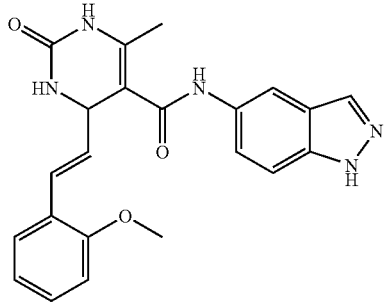

The title compound was synthesized using the procedure recited in Example 1 (b), except (2E)-3-[2-(methyloxy)phenyl]-2-propenal was utilized. MS (ES+) m/z 404 [M+H]⁺.

Example 82

4-(2,2-diphenylethenyl)-N-1H-indazol-5-yl-6-methyl-2-oxo-1,2,3,4-tetrahydro-5-pyrimidinecarboxamide

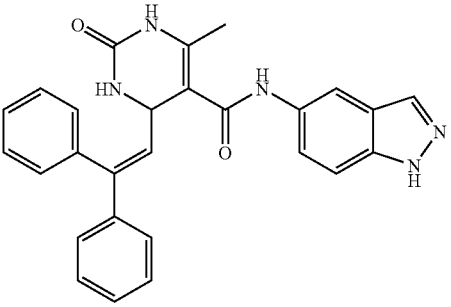

The title compound was synthesized using the procedure recited in Example 1(b), except 3,3-diphenyl-2-propenal was utilized. MS (ES+) m/z 450 [M+H]⁺.

Example 83

4-[(Z)-1-chloro-2-phenylethenyl]-N-1H-indazol-5-yl-6-methyl-2-oxo-1,2,3,4-tetrahydro-5-pyrimidinecarboxamide

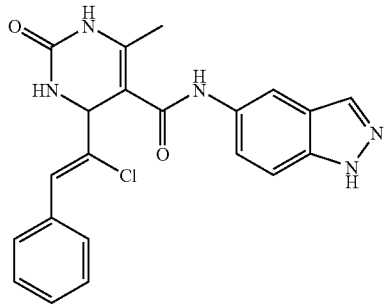

The title compound was synthesized using the procedure recited in Example 1(b), except (2Z)-2-chloro-3-phenyl-2-propenal was utilized. MS (ES+) m/z 408 [M+H]⁺.

Example 84

N-1H-indazol-5-yl-6-methyl-2-oxo-4-{[(phenylmethyl)oxy]methyl}-1,2,3,4-tetrahydro-5-pyrimidinecarboxamide

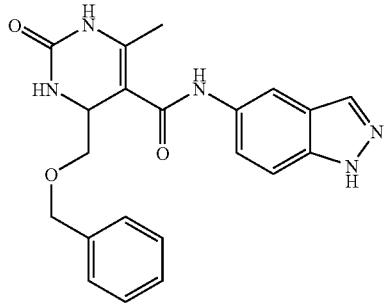

The title compound was synthesized using the procedure recited in Example 1(b), except [(phenylmethyl)oxy]acetaldehyde was utilized. MS (ES+) m/z 392 [M+H]⁺.

Example 85

N-1H-indazol-5-yl-6-methyl-2-oxo-4-(phenylethynyl)-1,2,3,4-tetrahydro-5-pyrimidinecarboxamide

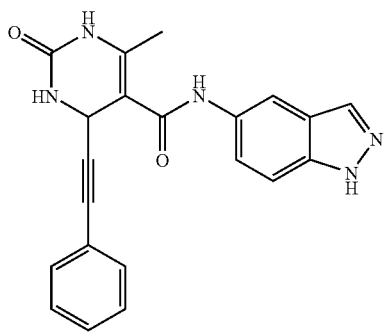

The title compound was synthesized using the procedure recited in Example 1(b), except 3-phenyl-2-propynal was utilized. MS (ES+) m/z 372 [M+H]+.

Example 86

4-(2,2'-bithien-5-yl)-N-1H-indazol-5-yl-6-methyl-2-oxo-1,2,3,4-tetrahydro-5-pyrimidinecarboxamide

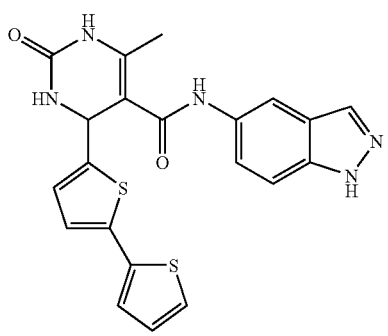

The title compound was synthesized using the procedure recited in Example 1(b), except 2,2'-bithiophene-5-carbaldehyde was utilized. MS (ES+) m/z 436 [M+H]+.

Example 87

N-1H-indazol-5-yl-6-methyl-4-(3-methyl-1-benzothien-2-yl)-2-oxo-1,2,3,4-tetrahydro-5-pyrimidinecarboxamide

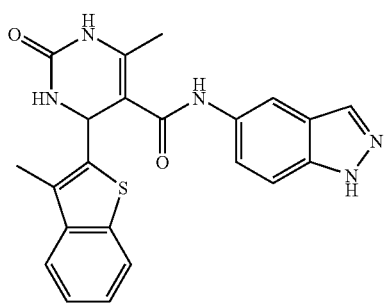

The title compound was synthesized using the procedure recited in Example 1(b), except 3-methyl-1-benzothiophene-2-carbaldehyde was utilized. MS (ES+) m/z 418 [M+H]+.

Example 87

4-(5-chloro-2-thienyl)-N-1H-indazol-5-yl-6-methyl-2-oxo-1,2,3,4-tetrahydro-5-pyrimidinecarboxamide

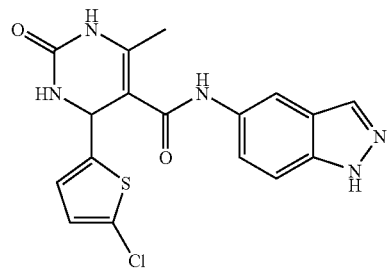

The title compound was synthesized using the procedure recited in Example 1(b), except 5-chloro-2-thiophenecarbaldehyde was utilized. MS (ES+) m/z 388 [M+H]+.

Example 88

N-1H-indazol-5-yl-6-methyl-2-oxo-4-(1,3-thiazol-2-yl)-1,2,3,4-tetrahydro-5-pyrimidinecarboxamide

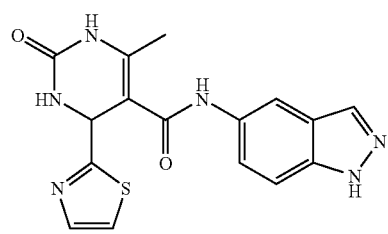

The title compound was synthesized using the procedure recited in Example 1(b), except 1,3-thiazole-2-carbaldehyde was utilized. MS (ES+) m/z 355 [M+H]+.

Example 89

N-1H-indazol-5-yl-6-methyl-4-(3-methyl-2-thienyl)-2-oxo-1,2,3,4-tetrahydro-5-pyrimidinecarboxamide

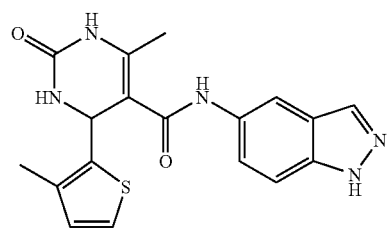

The title compound was synthesized using the procedure recited in Example 1(b), except 3-methyl-2-thiophenecarbaldehyde was utilized. MS (ES+) m/z 368 [M+H]+.

Example 90

4-(1-benzothien-2-yl)-N-1H-indazol-5-yl-6-methyl-2-oxo-1,2,3,4-tetrahydro-5-pyrimidinecarboxamide

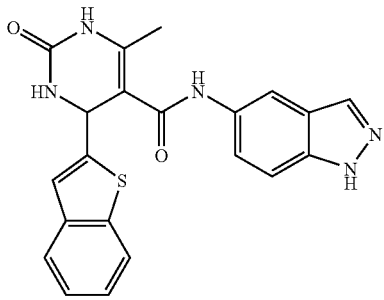

The title compound was synthesized using the procedure recited in Example 1(b), except 1-benzothiophene-2-carbaldehyde was utilized. MS (ES+) m/z 404 [M+H]$^+$.

Example 91

N-1H-indazol-5-yl-6-methyl-2-oxo-4-{3-[(phenylmethyl)oxy]phenyl}-1,2,3,4-tetrahydro-5-pyrimidinecarboxamide

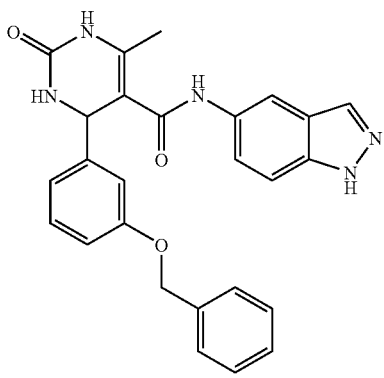

The title compound was synthesized using the procedure recited in Example 1(b) except 3-[(phenylmethyl)oxy]benzaldehyde was utilized. MS (ES+) m/z 454 [M+H]$^+$.

Example 92

4-(9H-fluoren-2-yl)-N-1H-indazol-5-yl-6-methyl-2-oxo-1,2,3,4-tetrahydro-5-pyrimidinecarboxamide

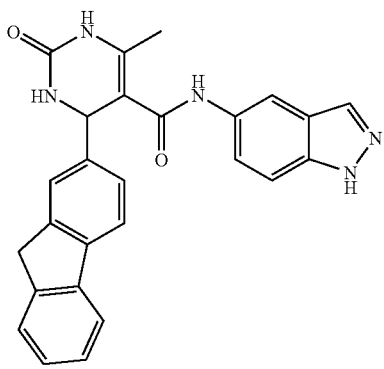

The title compound was synthesized using the procedure recited in Example 1(b), except 9H-fluorene-2-carbaldehyde was utilized. MS (ES+) m/z 436 [M+H]$^+$.

Example 93

4-(3-bromo-4-fluorophenyl)-N-1H-indazol-5-yl-6-methyl-2-oxo-1,2,3,4-tetrahydro-5-pyrimidinecarboxamide

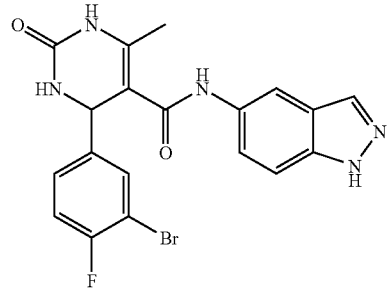

The title compound was synthesized using the procedure recited in Example 1(b), except 3-bromo-4-fluorobenzaldehyde was utilized. MS (ES+) m/z 445 [M+H]$^+$.

Example 94

N-1H-indazol-5-yl-6-methyl-4-[7-(methyloxy)-1,3-benzodioxol-5-yl]-2-oxo-1,2,3,4-tetrahydro-5-pyrimidinecarboxamide

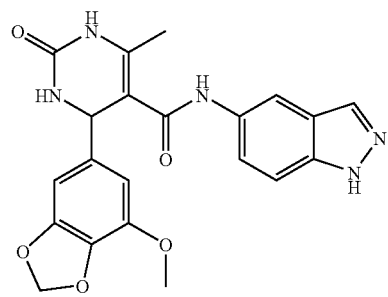

The title compound was synthesized using the procedure recited in Example 1(b), except 7-(methyloxy)-1,3-benzodioxole-5-carbaldehyde was utilized. MS (ES+) m/z 422 [M+H]$^+$.

Example 95

4-(1,3-benzodioxol-4-yl)-N-1H-indazol-5-yl-6-methyl-2-oxo-1,2,3,4-tetrahydro-5-pyrimidinecarboxamide

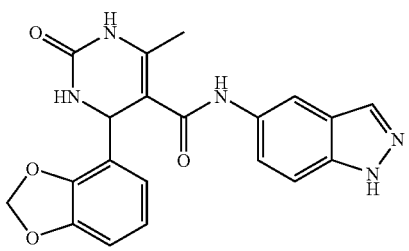

The title compound was synthesized using the procedure recited in Example 1(b), except 1,3-benzodioxole-4-carbaldehyde was utilized. MS (ES+) m/z 392 [M+H]$^+$.

Example 96

N-1H-indazol-5-yl-6-methyl-2-oxo-4-{3-[(trifluoromethyl)oxy]phenyl}-1,2,3,4-tetrahydro-5-pyrimidinecarboxamide

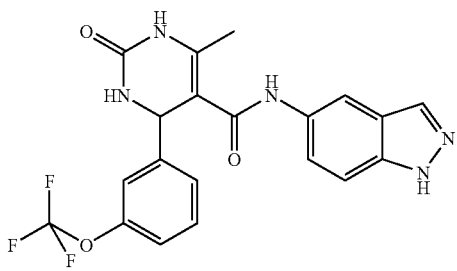

The title compound was synthesized using the procedure recited in Example 1(b), except 3-[(trifluoromethyl)oxy]benzaldehyde was utilized. MS (ES+) m/z 432 [M+H]$^+$.

Example 97

N-1H-indazol-5-yl-6-methyl-2-oxo-4-[3-(trifluoromethyl)phenyl]-1, Z 3,4-tetrahydro-5-pyrimidinecarboxamide

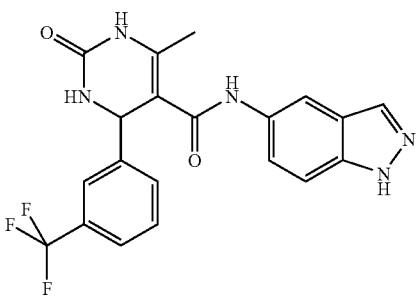

The title compound was synthesized using the procedure recited in Example 1(b), except 3-(trifluoromethyl)benzaldehyde was utilized. MS (ES+) m/z 416 [M+H]$^+$.

Example 98

4-[3-Hydroxy-4-(methyloxy)phenyl]-N-1H-indazol-5-yl-6-methyl-2-oxo-1,2,3,4-tetrahydro-5-pyrimidinecarboxamide

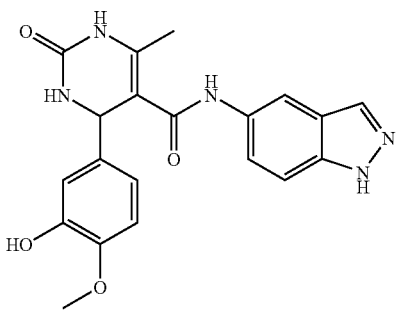

The title compound was synthesized using the procedure recited in Example 1(b), except 3-hydroxy-4-(methyloxy)benzaldehyde was utilized. MS (ES+) m/z 394 [M+H]$^+$.

Example 99

4-(5-Chloro-1,3-benzodioxol-4-yl)-N-1H-indazol-5-yl-6-methyl-2-oxo-1,2,3,4-tetrahydro-5-pyrimidinecarboxamide

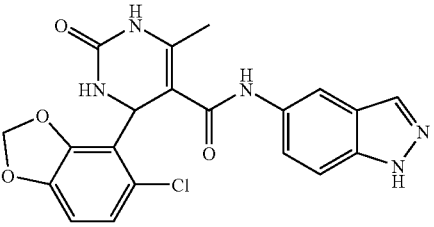

The title compound was synthesized using the procedure recited in Example 1(b), except 5-chloro-1,3-benzodioxole-4-carbaldehyde was utilized. MS (ES+) m/z 426 [M+H]$^+$.

Example 100

N-1H-indazol-5-yl-6-methyl-2-oxo-4-[5-(2-pyridinyl)-2-thienyl]-1,2,3,4-tetrahydro-5-pyrimidinecarboxamide

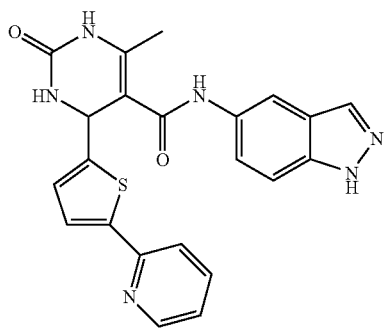

The title compound was synthesized using the procedure recited in Example 1(b), except 5-(2-pyridinyl)-2-thiophenecarbaldehyde was utilized. MS (ES+) m/z 431 [M+H]$^+$.

Example 101

N-1H-indazol-5-yl-6-methyl-2-oxo-4-(2-phenyl-1,3-thiazol-4-yl)-1,2,3,4-tetrahydro-5-pyrimidinecarboxamide

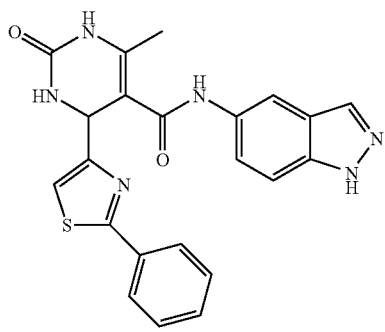

The title compound was synthesized using the procedure recited in Example 1(b), except 2-phenyl-1,3-thiazole-4-carbaldehyde was utilized. MS (ES+) m/z 431 [M+H]$^+$.

Example 102

N-1H-indazol-5-yl-6-methyl-4-[5-(methylthio)-2-thienyl]-2-oxo-1,2,3,4-tetrahydro-5-pyrimidinecarboxamide

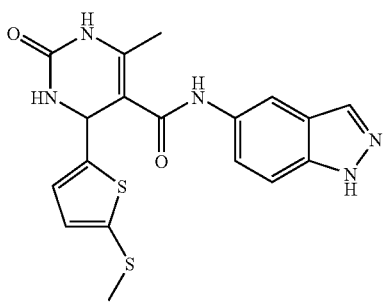

The title compound was synthesized using the procedure recited in Example 1(b), except 5-(methylthio)-2-thiophenecarbaldehyde was utilized. MS (ES+) m/z 400 [M+H]$^+$.

Example 103

4-(1,3-benzothiazol-2-yl)-N-1H-indazol-5-yl-6-methyl-2-oxo-1,2,3,4-tetrahydro-5-pyrimidinecarboxamide

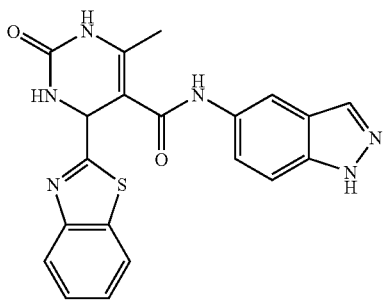

The title compound was synthesized using the procedure recited in Example 1(b), except 1,3-benzothiazole-2-carbaldehyde was utilized. MS (ES+) m/z 405 [M+H]$^+$.

Example 104

4-(2H-Chromen-3-yl)-N-1H-indazol-5-yl-6-methyl-2-oxo-1,2,3,4-tetrahydro-5-pyrimidinecarboxamide

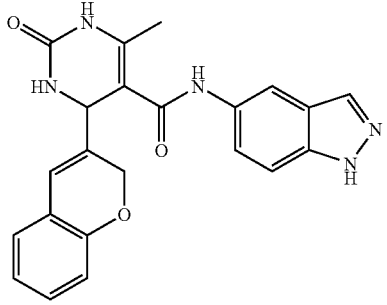

The title compound was synthesized using the procedure recited in Example 1(b), except 2H-chromene-3-carbaldehyde was utilized. MS (ES+) m/z 402 [M+H]$^+$.

Example 105

N-1H-indazol-5-yl-6-methyl-2-oxo-4-[5-(phenylethynyl)-2-thienyl]-1,2,3,4-tetrahydro-5-pyrimidinecarboxamide

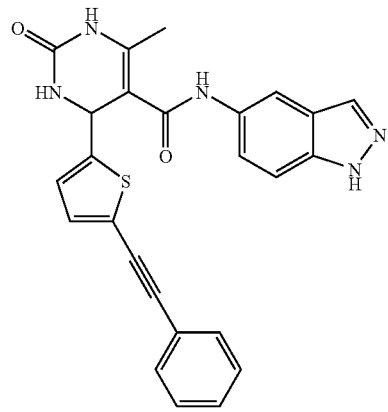

The title compound was synthesized using the procedure recited in Example 1(b), except 5-(phenylethynyl)-2-thiophenecarbaldehyde was utilized. MS (ES+) m/z 454 [M+H]$^+$.

Example 106

N-1H-indazol-5-yl-6-methyl-2-oxo-4-[4-(phenylethynyl)-2-thienyl]-1,2,3,4-tetrahydro-5-pyrimidinecarboxamide

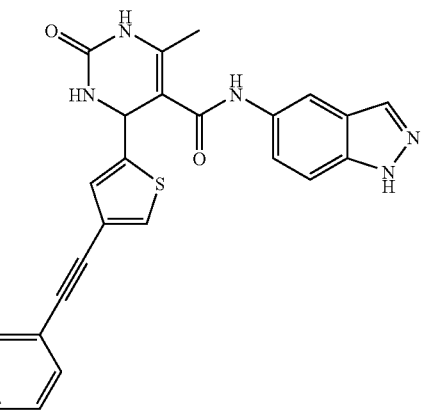

The title compound was synthesized using the procedure recited in Example 1(b), except 4-(phenylethynyl)-2-thiophenecarbaldehyde was utilized. MS (ES+) m/z 454

Example 107

N-1H-Indazol-5-yl-6-methyl-4-(5-methyl-2-thienyl)-2-oxo-1,2,3,4-tetrahydro-5-pyrimidinecarboxamide

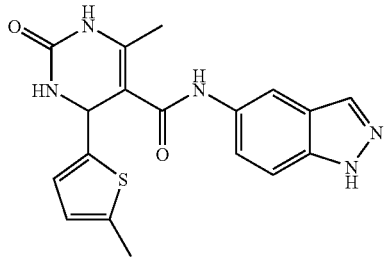

The title compound was synthesized using the procedure recited in Example 1(b), except 5-methyl-2-thiophenecarbaldehyde was utilized. MS (ES+) m/z 368 [M+H]$^+$.

Example 108

N-1H-Indazol-5-yl-6-methyl-4-{5-[1-methyl-5-(trifluoromethyl)-1H-pyrazol-3-yl]-2-thienyl}-2-oxo-1,2,3,4-tetrahydro-5-pyrimidinecarboxamide

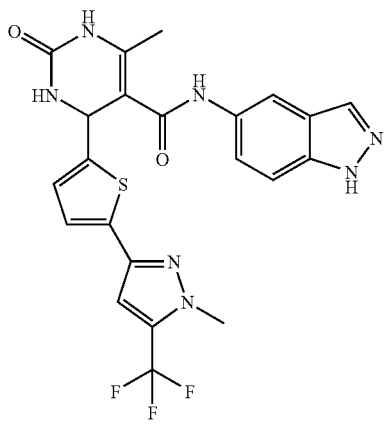

The title compound was synthesized using the procedure recited in Example 1(b), except 5-[1-methyl-5-(trifluoromethyl)-1H-pyrazol-3-yl]-2-thiophenecarbaldehyde was utilized. MS (ES+) m/z 502 [M+H]$^+$.

Example 109

N-1H-Indazol-5-yl-6-methyl-2-oxo-4-[4-(2-pyridinyl)phenyl]-1,2,3,4-tetrahydro-5-pyrimidinecarboxamide

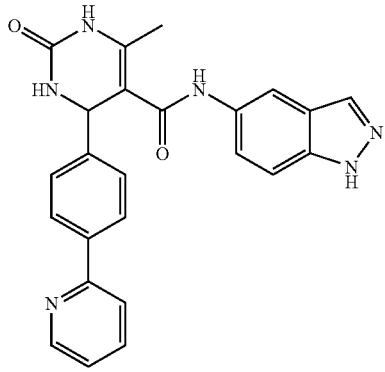

The title compound was synthesized using the procedure recited in Example 1(b), except 4-(2-pyridinyl)benzaldehyde was utilized. MS (ES+) m/z 425 [M+H]$^+$.

Example 110

4-[4-(Dimethylamino)phenyl]-N-1H-indazol-5-yl-6-methyl-2-oxo-1,2,3,4-tetrahydro-5-pyrimidinecarboxamide

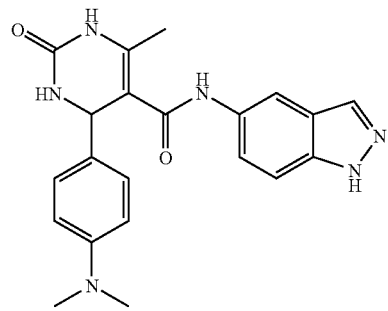

The title compound was synthesized using the procedure recited in Example 1(b), except 4-(dimethylamino)benzaldehyde was utilized. MS (ES+) m/z 391 [M+H]$^+$.

Example 111

4-[4-(Diethylamino)phenyl]-N-1H-indazol-5-yl-6-methyl-2-oxo-1,2,3,4-tetrahydro-5-pyrimidinecarboxamide

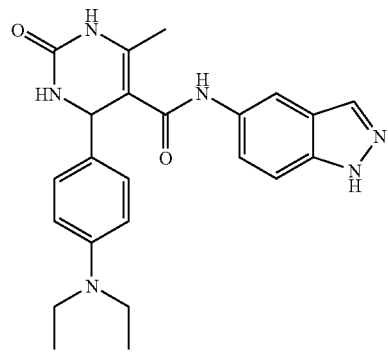

The title compound was synthesized using the procedure recited in Example 1(b), except 4-(dimethylamino)benzaldehyde was utilized. MS (ES+) m/z 432 [M+H]$^+$.

Example 112

4-(2-Chloro-3-quinolinyl)-N-1H-indazol-5-yl-6-methyl-2-oxo-1,2,3,4-tetrahydro-5-pyrimidinecarboxamide

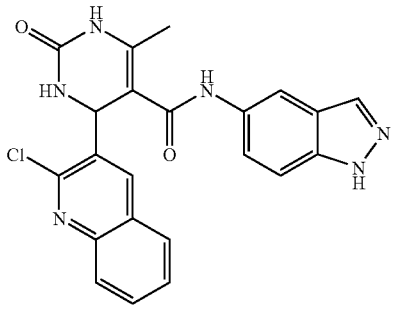

The title compound was synthesized using the procedure recited in Example 1(b), except 2-chloro-3-quinolinecarbaldehyde was utilized. MS (ES+) m/z 433 [M+H]⁺.

Example 113

N-1H-Indazol-5-yl-6-methyl-4-(4-methyl-3,4-dihydro-2H-1,4-benzoxazin-7-yl)-2-oxo-1,2,3,4-tetrahydro-5-pyrimidinecarboxamide

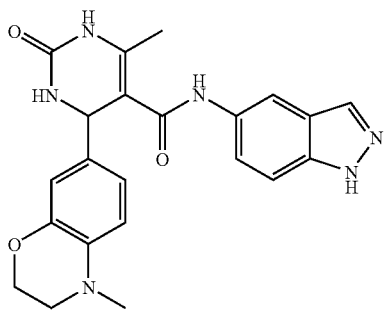

The title compound was synthesized using the procedure recited in Example 1(b), except 4-methyl-3,4-dihydro-2H-1,4-benzoxazine-7-carbaldehyde was utilized. MS (ES+) m/z 419 [M+H]⁺.

Example 114

N-1H-Indazol-5-yl-6-methyl-4-[4-(4-morpholinyl)phenyl]-2-oxo-1,2,3,4-tetrahydro-5-pyrimidinecarboxamide

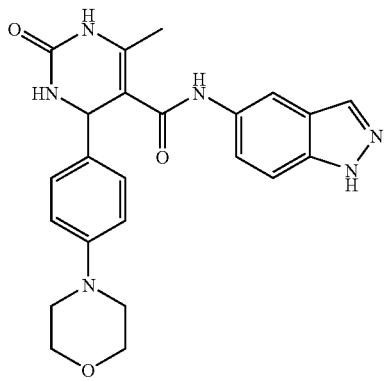

The title compound was synthesized using the procedure recited in Example 1(b), except 4-(4-morpholinyl)benzaldehyde was utilized. MS (ES+) m/z 433 [M+H]⁺.

Example 115

N-1H-indazol-5-yl-6-methyl-2-oxo-4-[4-(2-thienyl)phenyl]-1,2,3,4-tetrahydro-5-pyrimidinecarboxamide

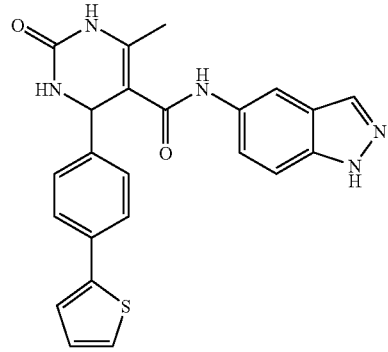

The title compound was synthesized using the procedure recited in Example 1(b), except 4-(2-thienyl)benzaldehyde was utilized. MS (ES+) m/z 430 [M+H]⁺.

Example 116

N-1H-Indazol-5-yl-6-methyl-2-oxo-4-[4-(1H-pyrazol-1-yl)phenyl]-1,2,3,4-tetrahydro-5-pyrimidinecarboxamide

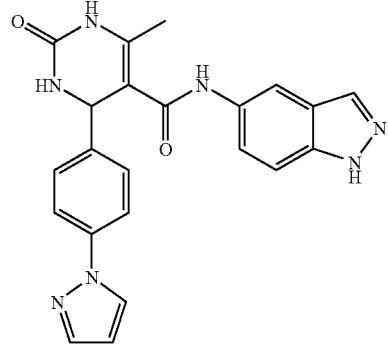

The title compound was synthesized using the procedure recited in Example 1(b), except 4-(1H-pyrazol-1-yl)benzaldehyde was utilized. MS (ES+) m/z 414 [M+H]⁺.

Example 117

N-1H-Indazol-5-yl-6-methyl-2-oxo-4-[4-(1H-1,2,4-triazol-1-yl)phenyl]-1,2,3,4-tetrahydro-5-pyrimidinecarboxamide

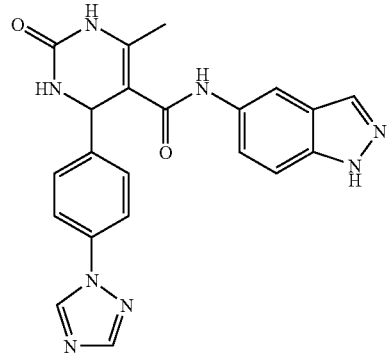

The title compound was synthesized using the procedure recited in Example 1(b), except 4-(1H-1,2,4-triazol-1-yl)benzaldehyde was utilized. MS (ES+) m/z 415 [M+H]+.

Example 118

4-[2,3-Difluoro-4-(trifluoromethyl)phenyl]-N-1H-indazol-5-yl-6-methyl-2-oxo-1,2,3,4-tetrahydro-5-pyrimidinecarboxamide

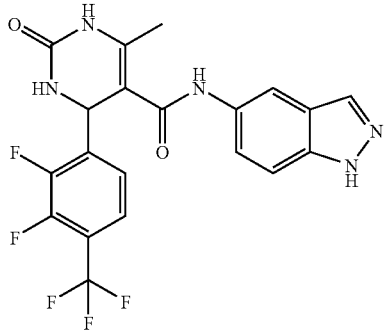

The title compound was synthesized using the procedure recited in Example 1(b), except 2,3-difluoro-4-(trifluoromethyl)benzaldehyde was utilized. MS (ES+) m/z 451 [M+H]+.

Example 119

4-[4-(1H-Benzimidazol-1-yl)phenyl]-N-1H-indazol-5-yl-6-methyl-2-oxo-1,2,3,4-tetrahydro-5-pyrimidinecarboxamide

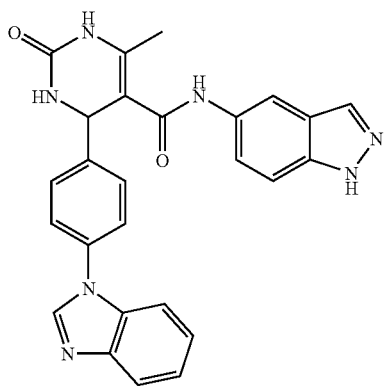

The title compound was synthesized using the procedure recited in Example 1(b), except 4-(1H-benzimidazol-1-yl)benzaldehyde was utilized. MS (ES+) m/z 464 [M+H]+.

Example 120

4-(4-Fluorophenyl)-N-[3-(4-fluorophenyl)-1H-indazol-5-yl]-6-methyl-2-oxo-1,2,3,4-tetrahydro-5-pyrimidinecarboxamide

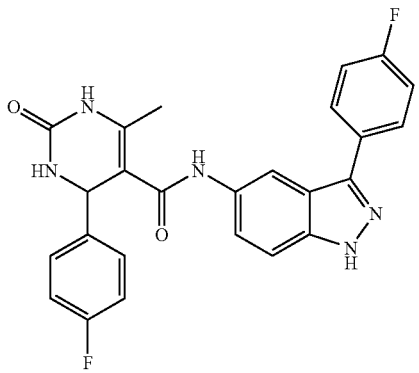

(a) 3-Bromo-5-nitro-1H-indazole

To a stirred suspension of 5-Nitro-1H-indazole (15.0 g, 92.0 mmol) in 400 ml methanol was added bromine (4.7 ml, 92.0 mmol) dropwise at room temperature. The mixture was stirred at room temperature overnight. The solvent was evaporated to dryness to afford the title compound, (25.0 g, 100%); MS (ES+) m/e 243 [M+H]+.

(b) 1,1-Dimethylethyl 3-bromo-5-nitro-1H-indazole-1-carboxylate

To a stirred suspension of product from Step (a) (1.0 g, 4.1 mmol) in 4.5 ml 1M NaOH solution was added 5 ml THF. Melted di-tert-butyl dicarbonate (0.9 g, 4.1 mmol) was added at room temperature and the mixture was stirred for 15 h. Water (8 ml) was then added to the clear solution, which was extracted with CHCl3. The organic layer was washed with Sat'd NaHCO3. The combined aqueous layers were cooled to 4° C., and the PH was adjusted to 1.5 with 1M KHSO4 solution. The aqueous layer was extracted 4× with 10 ml diethyl ether. The organic layers were combined and dried over Na2SO4. The solvent was evaporated to dryness to afford 1.1 g of the title compound (78%); MS (ES+) m/e 343 [M+H]+.

(c) 3-(4-Fluorophenyl)-5-nitro-1H-indazole

The product from Step (b) (0.5 g, 1.5 mmol), 4-fluoro phenylboronic acid (0.31 g, 2.2 mmol) and Pd(dppf)2Cl2.CH2Cl2 (0.12 g, 0.15 mmol) were combined in 9 ml of 2:1 Dioxane/2 M K2CO3 The reaction mixture was sealed and heated to 95° C. for 18 h. The resulting biphasic mixture was cooled to room temperature. The phases were separated and the organic phase (top) was filtered. The aqueous layer was extracted once with EtOAc. The combined organic phases were washed with sat'd NaHCO3, water, brine, dried (Na2SO4) and concentrated in vacuo. The residue was purified by silica gel chromatography (5% MeOH/CH$_2$Cl$_2$) to afford 0.37 g of the title compound, (100%); MS (ES+) m/e 259 [M+H]$^+$.

(d) 3-(4-Fluorophenyl)-1H-indazol-5-amine

The product from Step (c) (0.5 g, 1.94 mmol) was dissolved in methanol (50 ml) and treated with 5 wt % Palladium on charcoal (0.15 g). The reaction mixture was pressurized with 50 psi of H$_2$ and stirred for 4 hours. The reaction was filtered and concentrated in vacuo to afford the title compound (0.36 g, 81%); MS (ES+) m/e 229 [M+H]$^+$.

(e) N-[3-(4-Fluorophenyl)-1H-indazol-5-yl]-3-oxobutanamide

The product of Step (d) (0.5 g, 2.2 mmol) was dissolved in acetonitrile (1 ml). In a separate flask, diketene (0.17 ml, 2.2 mmol, stabilized with copper sulfate) was dissolved in acetonitrile (1 ml). The diketene solution was added to the amine suspension In three portions, the reaction mixture was sealed and heated to 50° C. for 18 hours. The solvent was evaporated to dryness and purified by silica gel chromatography (5% MeOH/CH$_2$Cl$_2$) to afford the title compound, (0.3 g, 44%); MS (ES+) m/e 313 [M+H]$^+$.

(f) 4-(4-Fluorophenyl)-N-[3-(4-fluorophenyl)-1H-indazol-5-yl]-6-methyl-2-oxo-1,2,3,4-tetrahydro-5-pyrimidinecarboxamide The product from Step (e) (0.3 g, 0.96 mmol), urea (87 mg, 1.44 mmol) and Ytterbium trifluoromethane (60 mg, 0.096 mmol) were combined In acetonitrile (2 ml) and 4-fluorobenzaldehyde (0.1 ml, 0.96 mmol) was added. The reaction mixture was sealed and heated to 100° C. for 3 hours. The reaction was diluted with water (1 ml) and the solid product was collected by filtration. The solid was washed three times with 1:1 Et$_2$O/CH$_3$CN. The crude was purified by silica gel chromatography eluting with 10% MeOH in CH$_2$Cl$_2$ to afford the title compound, (0.15 g, 34%); MS (ES+) m/e 460 [M+H]$^+$.

Example 121

N-(3-Chloro-1H-indazol-5-yl)-4-(4-fluorophenyl)-6-methyl-2-oxo-1,2,3,4-tetrahydro-5-pyrimidinecarboxamide

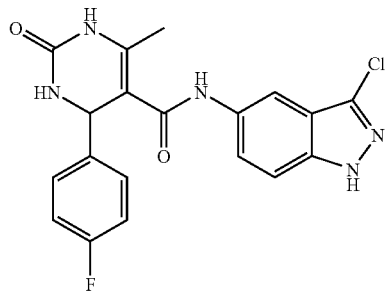

(a) 3-Chloro-5-nitro-1H-indazole

5-Nitro-1H-indazole (2.0 g, 12.3 mmol) was suspended in 40 ml ethanol and sodium hypochlorite solution (123 ml, 2.0 M, 246 mmol) was added. The mixture was heated to 75° C. and stirred overnight. The solvent was evaporated to dryness to afford the title compound. (2.4 g, 100%), MS (ES+) m/e 198 [M+H]$^+$.

(b) 3-Chloro-1H-indazol-5-amine

A solution of tin dichloride (1.93 g, 10.2 mmol) in HCl solution (0.85 ml, 6 M, 5.08 mmol) was added to a suspension of the product from Step (a) (0.5 g, 2.54 mmol) in 1.5 ml ethanol. The reaction mixture was heated at 60° C. for 30 minutes and then cooled to room temperature. The solvent was evaporated to dryness and purified by silica gel chromatography eluting with 30% EtOAc in CH$_2$Cl$_2$ to afford the title compound, (0.04 g, 10%); MS (ES+) m/e 168 [M+H]$^+$.

(c) N-(3-Chloro-1H-indazol-5-yl)-3-oxobutanamide

The product of Step (b) (0.4 g, 2.4 mmol) was dissolved in acetonitrile (1 ml). In a separate flask, diketene (0.18 ml, 2.4 mmol, stabilized with copper sulfate) was dissolved in acetonitrile (1 ml). The diketene solution was added to the amine suspension in three portions, the reaction mixture was sealed and heated to 50° C. for 18 hours. The solvent was evaporated to dryness and purified by silica gel chromatography eluting with 5% MeOH In CH$_2$Cl$_2$ to afford the title compound, (0.5 g, 83%); MS (ES+) m/e 252 [M+H]$^+$.

(d) N-(3-Chloro-1H-indazol-5-yl)-4-(4-fluorophenyl)-6-methyl-2-oxo-1,2,3,4-tetrahydro-5-pyrimidinecarboxamide The product from Step (c) (0.25 g, 1.0 mmol), urea (90 mg, 1.5 mmol) and Ytterbium trifluoromethanesulfonate (62 mg, 0.1 mmol) were combined in acetonitrile (5 ml) and 4-Fluorobenzaldehyde (0.11 ml, 1.0 mmol) was added to the mixture. The reaction mixture was sealed and heated to 100° C. for 3 hours. The reaction was diluted with water (1 ml) and the solid product was collected by filtration. The solid was washed three times with 1:1 Et$_2$O/CH$_3$CN to afford the title compound, (0.34 g, 85%); MS (ES+) m/e 401 [M+H]$^+$.

Example 122

N-(3-Chloro-1H-indazol-5-yl)-6-methyl-4-(2-naphthalenyl)-2-oxo-1,2,3,4-tetrahydro-5-pyrimidinecarboxamide

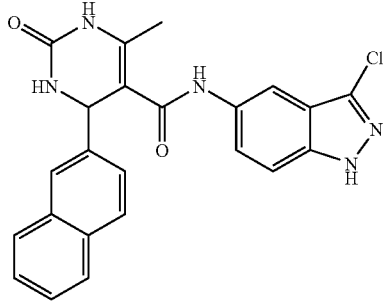

The title compound was synthesized using the procedure recited in Example 121, except 2-Naphthaldehyde was utilized. MS (ES+) m/e 433 [M+H]+.

Example 123

1-ethyl-4-(4-fluorophenyl)-N-1H-indazol-5-yl-6-methyl-2-oxo-1,2,3,4-tetrahydro-5-pyrimidinecarboxamide

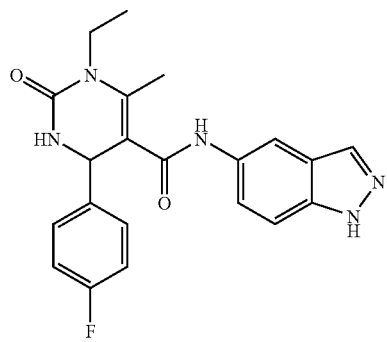

The title compound was synthesized using the procedure recited in Example 1(b) Method B, except N-ethyl urea was utilized. The title compound was purified using RP-HPLC (retention time 5.62 min) to yield 5 mg of beige powder (3%). MS (ES+) m/e 394 [M+H]+

Example 124

4-(4-Fluorophenyl)-N-1H-indazol-5-yl-2-oxo-6-propyl-1,2,3,4-tetrahydro-5-pyrimidinecarboxamide

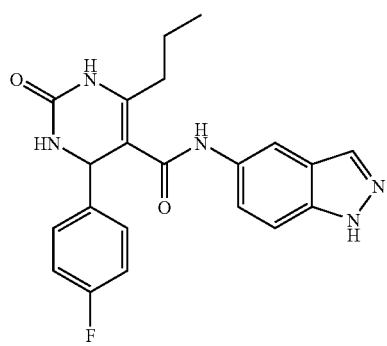

(a) N-1H-Indazol-5-yl-3-oxohexanamide

5-Aminoindazole (250 mg, 1.85 mmol, 1 equiv) and methyl-3-oxohexanoate (878 mg, 5.55 mmol, 3 equiv) were combined In a sealed microwave tube and heated in a SmithSynthesizer neat at 180° C. for 300 seconds. The residue was concentrated and purified by silica gel chromatography (5-75% EtOAc/Hexane) to yield 200 mg of ketoamide as a light yellow oil (44%). MS (ES+) m/e 246 [M+H]+

(b) 4-(4-Fluorophenyl)-N-1H-indazol-5-yl-2-oxo-6-propyl-1,2,3,4-tetrahydro-5-pyrimidinecarboxamide The title compound was synthesized using the procedure recited in Example 1(b) Method B, except N-1H-indazol-5-yl-3-oxohexanamide was utilized. The title compound was obtained as 13 mg of a beige powder (8%). MS (ES+) m/e 394 [M+H]+

Example 125

N-1H-Indazol-5-yl-4-(2-naphthalenyl)-2-oxo-6-propyl-1,2,3,4-tetrahydro-5-pyrimidinecarboxamide

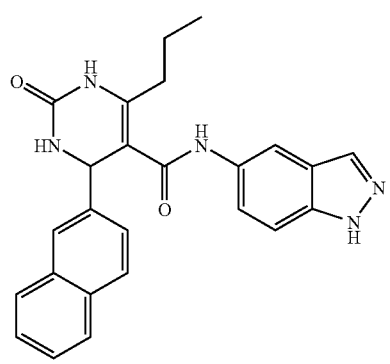

The title compound was synthesized using the procedure recited in Example 1(b) Method B, except 2-naphthaldehyde and N-1H-indazol-5-yl-3-oxohexanamide (Example 124(a)) was utilized. The title compound was obtained as 140 mg of a beige powder (80%). MS (ES+) m/e 426 [M+H]+

Example 126

4-(4-Fluorophenyl)-N-1H-indazol-5-yl-6-[(methyloxy)methyl]-2-oxo-1,2,3,4-tetrahydro-5-pyrimidinecarboxamide

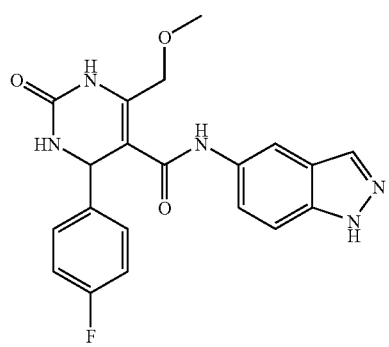

(a) methyl 4-(4-fluorophenyl)-6-[(methyloxy)methyl]-2-oxo-1,2,3,4-tetrahydro-5-pyrimidinecarboxylate Methyl 4-(methyloxy)-3-oxobutanoate (2.0 g, 13.69 mmol, 1 equiv), 4-Fluorobenzaldehyde (1.7 g, 13.69 mmol, 1 equiv), urea (1.64 g, 27.34 mmol, 2 equiv), and ytterbium triflate (854 mg, 1.37 mmol, 0.1 equiv) were combined in Toluene (3 mL) and heated to 100° C. in a sealed tube for three hours. The residue was diluted with 10 mL of water and extracted with EtOAc (10 mL). The organic layer was washed with brine and concentrated en vacuo to yield 4.03 g of the title compound as a light yellow oil (100%). MS (ES+) m/e 295 [M+H]$^+$ (b) 4-(4-Fluorophenyl)-N-1H-indazol-5-yl-6-[(methyloxy)methyl]-2-oxo-1,2,3,4-tetrahydro-5-pyrimidinecarboxamide The product of step (a) (4.03 g, 13.69 mmol, 1 equiv) and NaOH (2.5 N, 20 mL) were dissolved in methanol (60 mL) and heated to 60° C. in a sealed tube for four hours. The reaction mixture was diluted with water (~50 mL) and EtOAc (~50 mL), stirred, and separated. The aqueous layer was brought to pH 1 with 2N HCl and extracted with EtOAc. The organic layer was concentrated en vacuo and the residue (650 mg, 2.32 mmol, 1 equiv) was dissolved in DMF (13 mL). 5-aminoindazole (376 mg, 2.78 mmol, 1.2 equiv), EDC (531 mg, 2.78 mmol, 1.2 equiv), Et$_3$N (780 μL, 5.57 mmol, 2.4 equiv) and catalytic DMAP (5 mg) were added and the mixture was heated to 80° C. in a sealed tube for two hours. The residue was dissolved in EtOAc and water and extracted. The organic layer was washed with 1N HCl, satd. NaHCO$_3$ and Brine. The organic layer was concentrated en vacuo and then triturated with CH$_2$Cl$_2$/Hexane to give 368 mg of the title compound as a beige powder (40%). MS (ES+) m/e 396 [M+H]+

Example 127

4-(4-Fluorophenyl)-6-(1H-indazol-5-yl)hexahydro-1H-pyrrolo[3,4-d]pyrimidine-2,5-dione

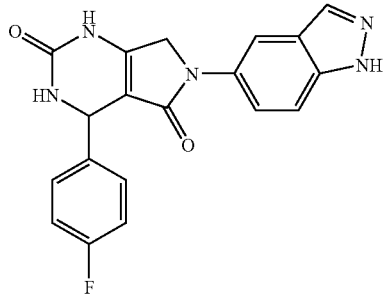

(a) methyl 6-(chloromethyl)-4-(4-fluorophenyl)-2-oxo-1,2,3,4-tetrahydro-5-pyrimidinecarboxylate Methyl 6-(chloromethyl)-4-(4-fluorophenyl)-2-oxo-1,2,3,4-tetrahydro-5-pyrimidinecarboxylate was synthesized using the procedure recited in Example 126(a) except that methyl 4-chloro-3-oxobutanoate was utilized. The product was obtained as a light yellow oil (1.01 g, 25%). MS (ES+) m/e 299 [M+H]$^+$ (b) methyl 4-(4-fluorophenyl)-6-[(1H-indazol-5-ylamino)methyl]-2-oxo-1,2,3,4-tetrahydro-5-pyrimidinecarboxylate The product of step (a) (0.100 g, 0.335 mmol, 1.00 equiv) and 5-aminoindazole (136 mg, 1.00 mmol, 3.00 equiv) were combined in DMF (2.5 mL) and heated first to 50° C. for one hour and then to 80° C. for two hours in a sealed tube. The residue was diluted with water and extracted with EtOAc. The organic layer was concentrated en vacuo to give 132 mg of the product as a light yellow oil (100%). MS (ES+) m/e 396 [M+H]$^+$ (c) 4-(4-fluorophenyl)-6-(1H-indazol-5-yl)hexahydro-1H-pyrrolo[3,4-d]pyrimidine-2,5-dione The product of step (b) (132 mg, 0.334 mmol, 1.00 equiv) and NaOH (2.5 N, 0.5 mL) were dissolved in methanol (2 mL) and heated to 60° C. in a sealed tube for three hours. The reaction mixture was diluted with water (~50 mL) and EtOAc (~50 mL), stirred, and separated. The aqueous layer was adjusted to pH 1 with 2N HCl and extracted with EtOAc. The organic layer was concentrated en vacuo and the residue (39 mg, 0.102 mmol, 1 equiv) was dissolved in DMF (5 mL). PS-carbodiimide resin (140 mg, 0.153 mmol, 1.5 equiv) was added and the reaction was stirred at room temperature for 18 hours. The reaction mixture was filtered and washed twice alternately with methanol and methylene chloride. The filtrate was concentrated en vacuo and the residue was purified by silica gel column (0-10% MeOH in CH$_2$Cl$_2$). The residue was triturated with CH$_2$Cl$_2$/Hexane to give 4 mg of the title compound as a beige powder (11%). MS (ES+) m/e 364 [M+H]$^+$ Example 128

N-1H-Indazol-5-yl-6-methyl-4-(3-nitrophenyl)-2-oxo-1,2,3,4-tetrahydro-5-pyrimidinecarboxamide

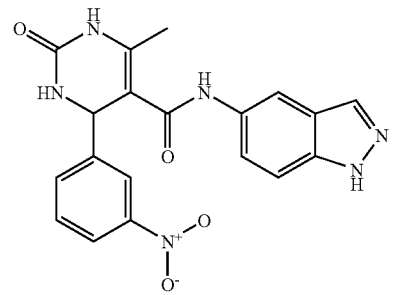

The title compound was synthesized using the procedure recited in Example 1(b) Method B, except 3-nitrobenzaldehyde was utilized and the reaction was run in Toluene/Acetonitrile. The title compound was obtained as 1.497 g of a beige powder (83%). MS (ES+) m/e 393 [M+H]+

Example 129

4-(4-Chlorophenyl)-6-(1H-indazol-5-yl)-3,4,6,7-tetrahydro-1H-pyrrolo[3,4-d]pyrimidine-2,5-dione

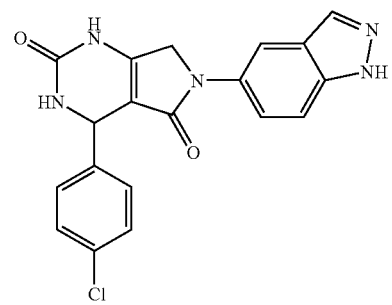

The title compound was synthesized using the procedure recited in Example 127 except that 4-chlorobenzaldehyde was utilized in step 127 (a) and the final product was further purified by Xterra Prep RP-HPLC (10-60% CH$_3$CN/5 mM NH$_4$HCO$_3$, 8 min gradient, 19×50 mm column, retention time 4.8 min) to yield 4 mg of beige powder (3%). MS (ES+) m/e 380 [M+H]$^+$ Example 130

4-(3-Aminophenyl)-N-1H-indazol-5-yl-6-methyl-2-oxo-1,2,3,4-tetrahydro-5-pyrimidinecarboxamide

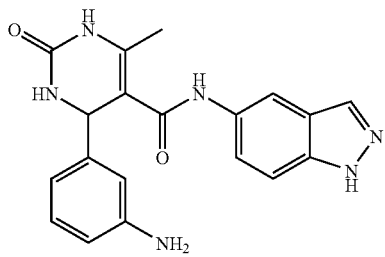

The product of example 1(a) (1.0 g, 4.6 mmol, 1.0 equiv), 3-aminobenzaldehyde (557 mg, 4.60 mmol, 1.00 equiv), urea (415 mg, 6.91 mmol, 1.50 equiv), and ammonium chloride (123 mg, 2.3 mmol, 0.5 equiv) were combined in ethanol (10 mL) and heated to 80° C. in a sealed tube for three hours. The residue was diluted with 0.5 mL of water and the product was collected by filtration. The solids were washed with a 1:1 solution of acetonitrile and diethyl ether. The product was purified by RP-HPLC (19×50 mm Xterra Prep, 10-45% CH$_3$CN/5 mM NH$_4$HCO$_3$ over 11 minutes, retention time 2.34 min) to yield 3 mg of beige powder (4%). MS (ES+) m/e 363 [M+H]$^+$ Example 131

4-(3,5-Dibromophenyl)-N-1H-indazol-5-yl-6-methyl-2-oxo-1,2,3,4-tetrahydro-5-pyrimidinecarboxamide

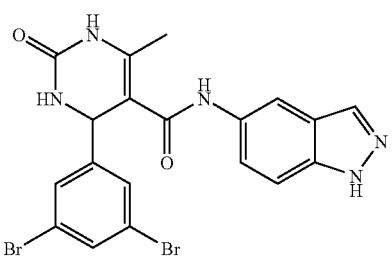

The title compound was synthesized using the procedure recited in Example 1(b), except 3,5-dibromobenzaldehyde was utilized. The residue was further purified by reverse phase HPLC (20-80% CH$_3$CN/H$_2$O/0.1% TFA, over 10 minutes) to provide 15 mg (6%) of the product as a pale grey solid. MS (ES+) m/e 505 [M+H]$^+$.

Example 132

4-(3,4-Difluorophenyl)-N-1H-indazol-5-yl-6-methyl-2-oxo-1,2,3,4-tetrahydro-5-pyrimidinecarboxamide

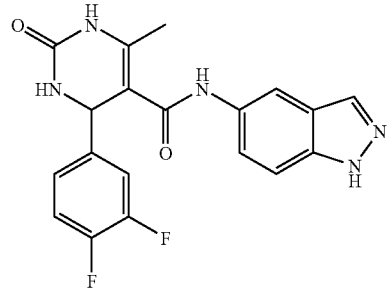

The title compound was synthesized using the procedure recited in Example 1(b), except 3,4-difluorobenzaldehyde was utilized. Filtration afforded 85 mg (48%) of the product as a pale grey solid which required no additional purification. MS m/e 384 [M+H]$^+$.

Example 133

N-1H-Indazol-5-yl-6-methyl-4-[(E)-1-methyl-2-phenylethenyl]-2-oxo-1,2,3,4-tetrahydro-5-pyrimidinecarboxamide

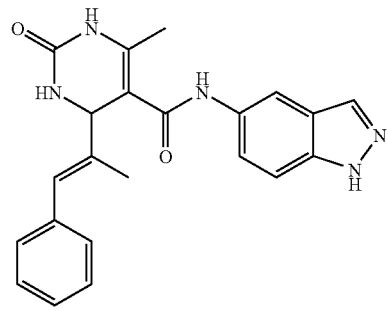

The title compound was synthesized using the procedure recited in Example 1(b), except α-methylcinnamaldehyde was utilized. Reverse phase HPLC purification provided 42 mg (24%) of a white solid. MS m/e 388 [M+H]$^+$.

Example 134

4-(4-Fluorophenyl)-N-1H-indazol-5-yl-3,6-dimethyl-2-oxo-1,2,3,4-tetrahydro-5-pyrimidinecarboxamide

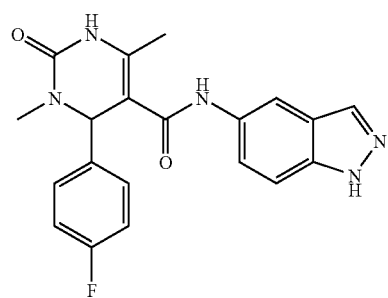

(a) Methyl-2-acetyl-3-(4-fluorophenyl)-2-propenoate

Methyl acetoacetate (7.48 mL, 69.4 mmol, 1 equiv), 4-fluorobenzaldehyde (7.44 mL, 69.4 mmol, 1 equiv), piperidine (0.510 mL) and acetic acid (0.594 mL) were combined in 1.5 L toluene. 4 Å molecular sieves (37.5 g) were added, and the reaction was stirred at room temperature for 4 days. The reaction mixture was filtered to remove the molecular sieves, and the reaction mixture was concentrated to afford 14.8 g (96%) of a yellow oil (1:1 mixture of E:Z isomers). $^1$H NMR (400 MHz, CDCl$_3$) 7.67 (s, 1H), 7.57 (s, 1H), 7.48-7.41 (m, 4H), 7.14-7.07 (m, 4H), 3.88 (s, 3H), 3.87 (s, 3H), 2.44 (s, 3H), 2.38 (s, 3H).

(b) Methyl 4-(4-fluorophenyl)-6-methyl-2-(methyloxy)-1,4-dihydro-5-pyrimidinecarboxylate The product of Step (a) (5.0 g, 22.5 mmol, 1 equiv) was combined with O-methyl isourea (5.8 g, 33.75 mmol, 1.5 equiv) and NaHCO$_3$ (5.7 g, 67.5 mmol, 3 equiv) in DMF (50 mL) and heated to 60° C. for 24 hours. The reaction mixture was diluted with EtOAc and H$_2$O and the phases were separated. The organic phase was washed with H$_2$O (2×) and satd. NaCl, then dried over sodium sulfate. The organic phase was filtered and concentrated en vacuo. The residue was purified by flash chromatography (25→35% EtOAc/hexanes) to provide 3.44 g (55%) of the title compound as a yellow foam (2:1 mixture of regioisomers by $^1$H NMR). MS (ES+) 279 [M+H]

(c) Methyl 6-(4-fluorophenyl)-1,4-dimethyl-2-(methyloxy)-1,6-dihydro-5-pyrimidinecarboxylate Iodomethane (0.314 mL, 5.04 mmol, 1.1 equiv) and sodium hydride (60% in mineral oil, 202 mg, 5.04 mmol, 1.1 equiv) were combined in DMF (10 mL) and cooled to 0° C. The product of Step (b) (1.275 g, 4.59 mmol, 1 equiv) was added slowly as a solution in DMF (11 mL). Following the addition, the reaction was warmed to room temperature and stirred for two hours. The reaction mixture was diluted with water and poured into EtOAc. The phases were separated and the aqueous phase was extracted with an additional portion of EtOAc. The combined organic phases were washed with water, 15% aq. Na$_2$S$_2$O$_4$, and satd. NaCl, then dried over sodium sulfate. The suspension was filtered and the filtrate was concentrated en vacuo to afford a mixture of two regioisomeric products. The isomers were separated by flash chromatography (3→5% Et$_2$O/CH$_2$Cl$_2$), and regiochemistry of the desired product was confirmed by NOE analysis. 550 mg (41%) of the title compound was isolated as a yellow solid. $^1$H NMR (400 MHz, CDCl$_3$) 7.30-7.27 (m, 2H), 7.02-6.97 (m, 2H), 5.21 (s, 1H), 3.91 (s, 3H), 3.63 (s, 3H), 2.84 (s, 3H), 2.38 (s, 3H).

(d) 4-(4-Fluorophenyl)-N-1H-indazol-5-yl-3,6-dimethyl-2-oxo-1,2,3,4-tetra-hydro-5-pyrimidinecarboxamide The product of Step (c) (550 mg, 1.88 mmol, 1 equiv) was dissolved in CH$_2$Cl$_2$ and HCl (4M in dioxane, 1.00 mL) was added. The reaction was stirred for 4 hours, then concentrated to afford 547 mg of a pale white solid. The solid was dissolved in MeOH (9.5 mL) and 2.5 M NaOH (3 mL) was added. The reaction was heated to 60° C. for 9 hours, then stirred at room temperature for an additional 16 hours. The reaction mixture was diluted with water and EtOAc and the phases were separated. The aqueous phase was acidified to pH 1 with 6N HCl, then extracted with EtOAc. The organic phase was washed with satd. NaCl, dried over sodium sulfate and filtered. The filtrate was concentrated en vacuo, then azeotropically dried several times with CH$_2$Cl$_2$/hexanes to provide 188 mg (36%) of the acid as a pale orange solid. The acid (188 mg, 0.712 mmol, 1 equiv), 5-aminoindazole (114 mg, 0.854 mmol, 1.2 equiv), EDC (163 mg, 0.854 mmol, 1.2 equiv) and triethylamine (0.283 mL, 1.71 mmol, 2.4 equiv) were combined in DMF (4 mL). The reaction was heated to 80° C. for 2 hours, then cooled to room temperature. The crude reaction mixture was partitioned between EtOAc and H$_2$O. The phases were separated and the organic phase was washed with 1N HCl, satd. NaHCO$_3$, sand satd. NaCl. The organic phase was dried over Na$_2$SO$_4$, filtered and the filtrate was concentrated en vacuo. The product was purified by flash chromatography (100% EtOAc) to afford 70.0 mg (26%) of the product as an off-white solid. MS (ES+) m/e 380 [M+H].

Example 135

6-Ethyl-4-(4-fluorophenyl)-N-1H-indazol-5-yl-2-oxo-1,2,3,4-tetrahydro-5-pyrimidinecarboxamide

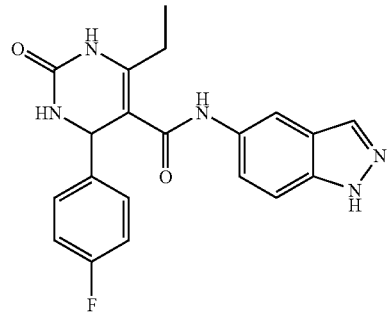

(a) N-1H-Indazol-5-yl-3-oxopentanamide

Methyl propionyl acetate (1.2 mL, 9.60 mmol, 6.3 equiv) was combined with 5-aminoindazole (200 mg, 1.50 mmol, 1 equiv) and heated in a SmithSynthesizer at 180° C. for three minutes. The reaction mixture was purified by flash chromatography (50% EtOAc/hexanes) to afford 146 mg (42%) of the title compound as a pale brown solid. MS (ES+) m/e 232 [M+H].

(b) 6-Ethyl-4-(4-fluorophenyl)-N-1H-indazol-5-yl-2-oxo-1,2,3,4-tetrahydro-5-pyrimidinecarboxamide The product of Step (a) (126 mg, 0.545 mmol, 1 equiv), 4-fluorobenzaldehyde (0.058 mL, 0.545 mmol, 1 equiv), urea (49 mg, 0.818 mmol, 1.5 equiv), and ytterbium triflate (37 mg, 0.06 mol, 0.10 equiv) were combined in CH$_3$CN (2 mL) and heated to reflux for 4.5 hours. The reaction was diluted with water and the resulting precipitate was collected by filtration. The solid was washed with water, CH$_3$CN, and Et$_2$O. 140 mg (68%) of the product was isolated as a pale grey solid. MS (ES+) m/e 380 [M+H]$^+$.

Example 136

N-(6-Chloro-1H-indazol-5-yl)-4-(4-fluorophenyl)-6-methyl-2-oxo-1,2,3,4-tetrahydro-5-pyrimidinecarboxamide

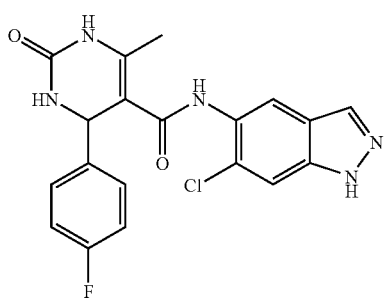

(a) 6-Chloro-1H-indazol-5-amine

5-Chloro-2-methyl-4-nitroaniline (1.0 g, 5.3 mmol, 1.0 equiv) was dissolved in AcOH (46 mL) and cooled to 15° C. NaNO$_2$ (0.37 g, 5.3 mmol, 1.0 equiv) was dissolved In H$_2$O (1 mL) and added all at once via pipet. The reaction was warmed to room temperature and stirred for 28 hours. The reaction mixture was concentrated en vacuo to provide an orange solid, which was azeotroped several times with hexanes. The solid was dissolved in EtOH (12 mL) and added to a solution of SnCl$_2$ (3.4 g, 18 mmol, 3.4 equiv) in 6N HCl (12 mL) The reaction mixture was heated to 60° C. for two hours, then cooled to room temperature and basified with 50% NaOH. The resulting precipitate was removed by filtration and washed with EtOAc. The filtrate was transferred to a separatory funnel and the phases were separated. The aqueous phase was extracted with EtOAc, and the combined organic phases were dried over Na$_2$SO$_4$. The solution was filtered, and the filtrate was concentrated in vacuo. The resulting residue was purified by flash chromatography (25% EtOAc/CH$_2$Cl$_2$) to afford 170 mg (19%) of the title compound as a pale yellow solid.

$^1$H NMR (400 MHz, d$_6$-DMSO) 7.80 (s, 1H), 7.47 (s, 1H), 7.04 (s, 1H), 4.95 (s, 2H).

(b) N-(6-Chloro-1H-indazol-5-yl)-3-oxobutanamide

The product of Step (a) (170 mg, 1.0 mmol, 1.0 equiv) was dissolved in CH$_3$CN (1 mL) and diketene (0.078 mL, 1.0 mmol, 1.0 equiv) was added. The reaction was heated to 50° C. for 2 hours, then refluxed for an additional 20 hours. The reaction was concentrated en vacuo to afford the title compound in quantitative yield. MA (ES+) m/e 252 [M+H].

(c) N-(6-Chloro-1H-indazol-5-yl)-4-(4-fluorophenyl)-6-methyl-2-oxo-1,2,3,4-tetrahydro-5-pyrimidinecarboxamide The product from Step (b) (0.100 g, 0.398 mmol, 1.00 equiv), 4-fluorobenzaldehyde (0.0430 mL, 0.398 mmol, 1.00 equiv), urea (36 mg, 0.60 mmol, 1.0 equiv), and ytterbium triflate (25 mg, 0.040 mmol, 0.10 equiv) and heated to 80° C. for 5.5 hours. The reaction was cooled to room temperature and water was added. The precipitate was collected by filtration and washed alternately with CH$_3$CN and Et$_2$O, affording 98 mg (62%) of the title compound. MS (ES+) m/e 400 [M+H].

Example 137

N-(6-Chloro-1H-indazol-5-yl)-6-methyl-4-(2-naphthalenyl)-2-oxo-1,2,3,4-tetrahydro-5-pyrimidinecarboxamide

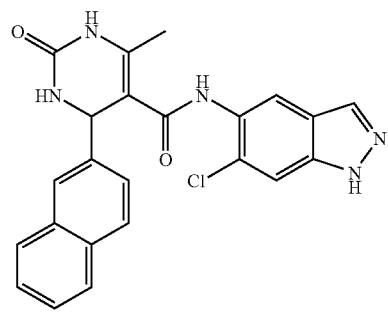

The product from Example 136, Step (c) (0.100 g, 0.398 mmol, 1.00 equiv), 2-naphthaldehyde (62 mg, 0.398 mmol, 1.00 equiv), urea (36 mg, 0.60 mmol, 1.0 equiv), and ytterbium triflate (25 mg, 0.040 mmol, 0.10 equiv) and heated to 80° C. for 3 hours. The reaction was cooled to room temperature and water was added. The precipitate was collected by filtration and washed alternately with CH$_3$CN and Et$_2$O, affording 130 mg (76%) of the title compound. MS (ES+) m/e 432 [M+H].

Example 138

N-(6-Fluoro-1H-indazol-5-yl)-4-(4-fluorophenyl)-6-methyl-2-oxo-1,2,3,4-tetrahydro-5-pyrimidinecarboxamide

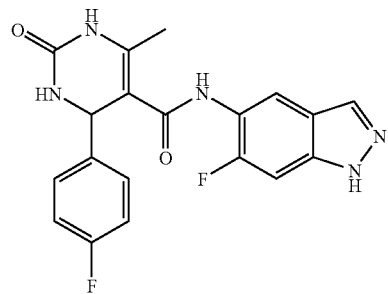

(a) N-(5-fluoro-2-methylphenyl)acetamide

5-Fluoro-2-methylaniline (10.0 g, 79.9 mmol, 1 equiv) was dissolved In toluene (50 mL) and placed in a cool water bath. Acetic anhydride (11.3 mL, 120 mmol, 1.5 equiv) was added slowly. After 15 minutes, a white precipitate had formed. The solid was collected by filtration and washed with toluene several times, affording 10.93 g (82%) of the title compound as a white crystalline solid. MS (ES+) m/e 213 [M+H].

(b) 5-Fluoro-2-methyl-4-nitroaniline

The product from Step (a) (5.00 g, 29.9 mmol, 1 equiv) was dissolved in concentrated H₂SO₄ (30 mL) and cooled to 0° C. Concentrated HNO₃ (2.2 mL) was added slowly via pipet, and the solution gradually became dark brown. After 30 minutes at 0° C., the reaction mixture was poured onto ice (~200 mL), and the mixture was allowed to stir and warm to room temperature. The solid precipitate was collected by filtration and washed several times with water. The solid was suspended in 6N HCl (30 mL) and the mixture was heated to reflux for 5 hours, then stirred at room temperature for 18 hours. The reaction mixture was diluted with H₂O and neutralized with solid K₂CO₃. The resulting precipitate was collected by filtration and rinsed several times with water, affording 2.82 g (55%) of the title compound as a brown solid. MS (ES+) m/e 171 [M+H].

(c) 6-Fluoro-5-nitro-1H-indazole

The product of Step (b) (1.22 g, 7.17 mmol, 1.0 equiv) was dissolved In AcOH (62 mL). NaNO₂ (0.495 g, 7.17 mmol, 1.0 equiv) was dissolved in H₂O (1.5 mL) and added all at once via pipet. The reaction was warmed to room temperature and stirred for 28 hours. The reaction mixture was concentrated en vacuo to provide an orange solid, which was dried azeotropically several times with hexanes. The residue was purified by flash chromatography (linear gradient 20→60% EtOAc/hexanes) to afford 550 mg (43%) of the title compound. MS (ES+) m/e 182 [M+H].

(d) 6-Fluoro-1H-indazol-5-amine

To the product of Step (c) (530 mg, 2.93 mmol, 1 equiv) and 10% Pd/C (200 mg) was added CH₂Cl₂ (10 mL) and MeOH (40 mL). The atmosphere was replaced with hydrogen gas and the solution was stirred at room temperature and atmospheric pressure for 2 hours. The reaction mixture was filtered through a plug of celite and rinsed with MeOH and CH₂Cl₂. The residue was purified by flash chromatography (linear gradient, 40→70% EtOAc/hexanes) affording 330 mg (75%) of the title compound as a pale purple solid. MS (ES+) m/e 152 [M+H].

(e) N-(6-Fluoro-1H-indazol-5-yl)-4-(4-fluorophenyl)-6-methyl-2-oxo-1,2,3,4-tetrahydro-5-pyrimidinecarboxamide The product of Step (d) (41.0 mg, 0.276 mmol, 1.0 equiv) was dissolved in CH₃CN (1 mL) and diketene (0.021 mL, 0.276 mmol, 1.0 equiv) was added. The reaction was heated to 80° C. for 2 hours, then cooled to room temperature and concentrated. The residue was dissolved in CH₃CN (1 mL). 4-Fluorobenzaldehyde (0.030 mL, 0.276 mmol, 1.00 equiv), urea (25 mg, 0.41 mmol, 1.5 equiv), and ytterbium triflate (17 mg, 0.028 mmol, 0.10 equiv) and heated to 80° C. for 3 hours. The reaction was cooled to room temperature and water was added. The precipitate was collected by filtration and washed alternately with CH₃CN and Et₂O. The residue was purified by reverse phase HPLC (740% CH₃CN/5 mM NH₄HCO₃, 19×50 mm Xterra Prep MS over 8 min) to provide 3 mg (3%) of the title compound. MS (ES+) m/e 384 [M+H].

Example 139

N-(7-Chloro-1H-indazol-5-yl)-4-(4-fluorophenyl)-6-methyl-2-oxo-1,2,3,4-tetrahydro-5-pyrimidinecarboxamide

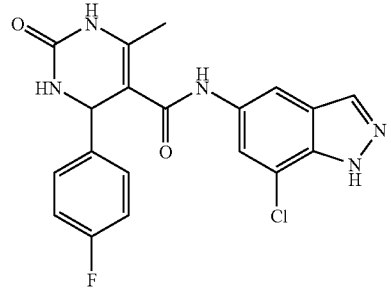

(a) 7-Chloro-5-nitro-1H-Indazole

7-Chloro-2-methyl-4-nitroaniline (1.0 g, 5.3 mmol, 1.0 equiv) was dissolved in AcOH (46 mL) and cooled to 15° C. NaNO₂ (0.37 g, 5.3 mmol, 1.0 equiv) was dissolved in H₂O (1 mL) and added all at once via pipet. The reaction was warmed to room temperature and stirred for 24 hours. The reaction mixture was concentrated en vacuo to provide an orange solid, which was azeotroped several times with hexanes. The residue was purified by flash chromatography (25→33% EtOAc/hexanes) to provide 350 mg (34%) of the title compound. (400 MHz, d₆-DMSO) 8.85 (s, 1H), 8.53 (s, 1H), 8.28 (s, 1H).

(b) N-(7-Chloro-1H-indazol-5-yl)-3-oxobutanamide

The product from Step (a) (350 mg, 1.77 mmol, 1 equiv) was dissolved in THF (15 mL). Satd. NaHCO₃ (3 mL) was added, followed by Na₂S₂O₄ (1.8 g). The mixture was heated to 70° C. for 3 hours, at which point an additional 0.500 g of Na₂S₂O₄ was added. After another hour, an additional 0.500 g of Na₂S₂O₄ was added. After a total of 20 hours, the reaction was cooled to room temperature. The reaction mixture wad diluted with EtOAc and satd. NaHCO₃ and the phases were separated. The organic phase was washed with H₂O, then with satd. NaCl and dried over Na₂SO₄. The suspension was filtered and the filtrate concentrated en vacuo. The resulting residue was purified by flash chromatography (25% EtOAc/CH₂Cl₂) to afford 80 mg (27%) of the amine. The solid (80.0 mg, 0.470 mmol, 1.0 equiv) was dissolved in CH₃CN (3 mL) and diketene (0.036 mL, 0.470 mmol, 1.0 equiv) was added. The reaction was heated to 50° C. for 20 hours. The reaction was concentrated en vacuo to afford the title compound in quantitative yield. MS (ES+) m/e 252 [M+H].

(c) N-(6-Chloro-1H-indazol-5-yl)-4-(4-fluorophenyl)-6-methyl-2-oxo-1,2,3,4-tetrahydro-5-pyrimidinecarboxamide The product from Step (b) (84.5 mg, 0.337 mmol, 1.00 equiv), 4-fluorobenzaldehyde (0.0360 mL, 0.337 mmol, 1.00 equiv), urea (30.0 mg, 0.506 mmol, 1.00 equiv), and ytterbium triflate (21 mg, 0.034 mmol, 0.10 equiv) and heated to

Example 140

N-(7-Chloro-1H-indazol-5-yl)-6-methyl-4-(2-naphthalenyl)-2-oxo-1,2,3,4-tetrahydro-5-pyrimidinecarboxamide

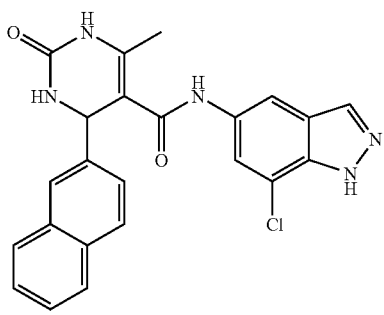

The product from Example 139, Step (b) (87.3 mg, 0.348 mmol, 1.00 equiv), 2-naphthaldehyde (54 mg, 0.348 mmol, 1.00 equiv), urea (32 mg, 0.53 mmol, 1.0 equiv), and ytterbium triflate (22 mg, 0.035 mmol, 0.10 equiv) and heated to 80° C. for 2 hours. The reaction was cooled to room temperature and water was added. The precipitate was collected by filtration and washed alternately with $CH_3CN$ and $Et_2O$, affording 78 mg (52%) of the title compound. MS (ES+) m/e 432 [M+H].

Example 141

N-(3-bromo-1H-indazol-5-yl)-4-(4-fluorophenyl)-6-methyl-2-oxo-1,2,3,4-tetrahydro-5-pyrimidinecarboxamide

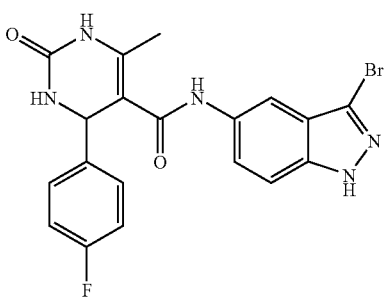

(a) 3-bromo-5-nitro-1H-indazole

5-Nitroindazole (20.0 g, 123 mmol, 1 equiv) was suspended in 500 mL MeOH. The mixture was refluxed and bromine (6.3 mL, 123 mmol, 1 equiv) was added dropwise. The reaction was stirred at reflux for 3 hours, then at room temperature for 2 days. The reaction mixture was filtered and the solid was washed with diisopropyl either to afford 24.9 g (84%) of the title compound as a yellow solid.

(b) 3-Bromo-1H-indazol-5-amine

The product of Step (a) (10.0 g, 41.3 mmol, 1.00 equiv) was suspended in EtOH (120 mL). $SnCl_2.H_2O$ (46.6 g, 206 mmol, 5.00 equiv) was added and the mixture was refluxed for 18 hours. The reaction mixture was concentrated en vacuo and water was added to the residue. The mixture was basified to pH 8 with satd. $NaHCO_3$ and extracted with EtOAc (3×). The combined organic extracts were washed with satd. NaCl, dried over $MgSO_4$, filtered and concentrated en vacuo. 8.10 g (92%) of the title compound was iolated as a purple solid.

(c) N-(3-Bromo-1H-indazol-5-yl)-3-oxobutanamide

The product of Step (b) (4.00 g, 18.86 mmol, 1 equiv) was suspended In $CH_3CN$ (20 mL). In a separate flask, diketene (1.45 mL, 18.89 mmol, 1 equiv) was dissolved in CH3CN (10 mL) The diketene solution was added to the initial suspension, and the mixture was heated to 50° C. for 18 hours. The reaction mixture was cooled and concentrated en vacuo. The resulting residue was purified by flash chromatography to afford 1.47 g (26%) of the product as a pink solid.

(d) N-(3-bromo-1H-indazol-5-yl)-4-(4-fluorophenyl)-6-methyl-2-oxo-1,2,3,4-tetrahydro-5-pyrimidinecarboxamide The product of Step (c) (330 mg, 1.11 mmol, 1 equiv), 4-fluorobenzaldehyde (120 uL, 1.13 mmol, 1.00 equiv), urea (100 mg, 1.67 mmol, 1.67 equiv), and Ytterbium triflate (70 mg, 0.12 mmol, 0.10 equiv) were combined in $CH_3CN$ (6 mL). The reaction vessel was sealed and heated to 100° C. for 18 hours. The reaction was cooled to room temperature and the precipitate was collected by filtration. The solid was washed with $Et_2O/CH_3CN$ several times, then purified by preparative LC-MS to afford 40 mg (8%) of a white solid. $^1H$ NMR (400 MHz, d6-DMSO) 13.3 (s, 1H), 9.69 (s, 1H), 8.77 (s, 1H), 7.96 (s, 1H), 7.62 (m, 1H), 7.48 (s, 2H), 7.35 (m, 2H), 7.17 (m, 2H), 5.43 (m, 1H), 2.07 (s, 3H).

Example 142

N-(3-bromo-1H-indazol-5-yl)-4-(2-naphthyl)-6-methyl-2-oxo-1,2,3,4-tetrahydro-5-pyrimidinecarboxamide

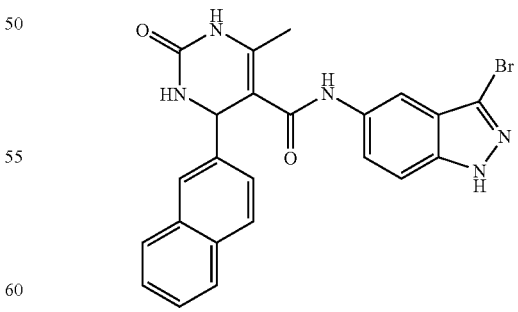

The title compound was synthesized using the procedure recited in Example 141(d), except 2-naphthaldehyde was utilized. $^1H$ NMR (400 MHz, d6-DMSO) 13.3 (s, 1H), 9.73 (s, 1H), 8.79 (s, 1H), 7.94-7.47 (m, 11H), 5.60 (m, 1H), 2.10 (s, 3H).

Example 143

N-(3-bromo-1H-indazol-5-yl)-4-(3-thiophenyl)-6-methyl-2-oxo-1,2,3,4-tetrahydro-5-pyrimidinecarboxamide

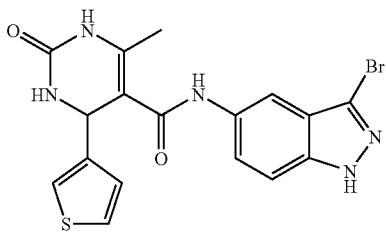

The title compound was synthesized using the procedure recited in Example 141(d), except 3-thiophenecarboxaldehyde was utilized. $^1$H NMR (400 MHz, d6-DMSO) 13.3 (s, 1H), 9.69 (s, 1H), 8.74 (s, 1H), 8.00 (s, 1H), 7.65-7.47 (m, 4H), 7.26 (s, 2H), 7.05 (d, 1H), 5.47 (m, 1H), 2.08 (s, 3H).

Example 144

4-(4-Bromophenyl)-N-1H-indazol-5-yl-6-methyl-2-oxo-1,2,3,4-tetrahydro-5-pyrimidinecarboxamide

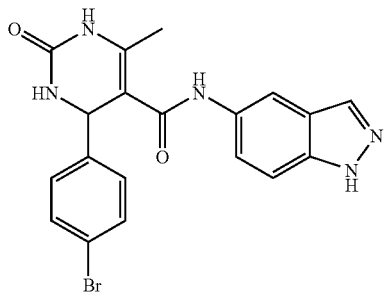

The title compound was synthesized using the procedure recited in Example 1, except 4-bromobenzaldehyde was utilized. Filtration afforded 670 mg (68%) of the product as a pale grey solid which required no additional purification. MS m/e 427 [M+H]$^+$.

Example 145

4-(3'-Amino-4-biphenylyl)-N-1H-indazol-5-yl-6-methyl-2-oxo-1,2,3,4-tetrahydro-5-pyrimidinecarboxamide

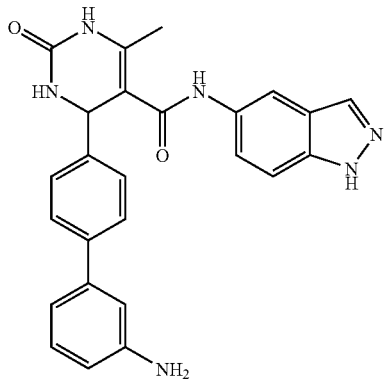

The product of Example 144 (0.100 g, 0.230 mmol, 1.00 equiv), Pd(dppf)Cl$_2$.CH$_2$Cl$_2$, and 3-aminoboronic acid (107 mg, 0.690 mmol, 3.00 equiv) were dissolved in dioxane (2 mL) and 1M aq. Na$_2$CO$_3$ (0.690 mL, 0.690 mmol, 3.00 equiv) was added. The reaction mixture was heated to 185° C. in a SmithSynthesizer for 6 minutes. The crude reaction mixture was filtered and concentrated to dryness. The residue was purified by reverse phase HPLC (30×100 Xterra prep, 5-70% CH$_3$CN/5 mM NH$_4$HCO$_3$ over 18 minutes) to afford 3.2 mg (3%) of the title compound as a white solid. MS (ES+) m/e 439 [M+H]

Example 146

N-1H-Indazol-5-yl-6-methyl-2-oxo-4-[4-(2-thienyl)phenyl]-1,2,3,4-tetrahydro-5-pyrimidinecarboxamide

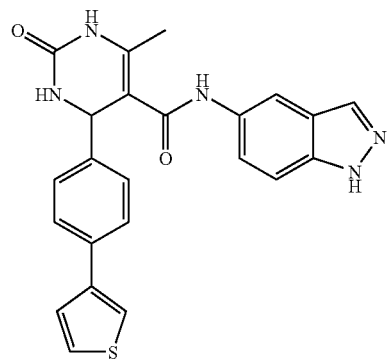

The title compound was synthesized using the procedure recited in Example 145, except thiophene 3-boronic acid was utilized. The residue was purified by reverse phase HPLC (30×100 Xterra prep, 20-80% CH$_3$CN/5 mM NH$_4$HCO$_3$ over 18 minutes) to afford the title compound as a white solid. MS (ES+) m/e 430 [M+H]

Example 147

4-(2' 4'-Difluoro-4-biphenylyl)-N-1H-indazol-5-yl-6-methyl-2-oxo-1,2,3,4-tetrahydro-5-pyrimidinecarboxamide

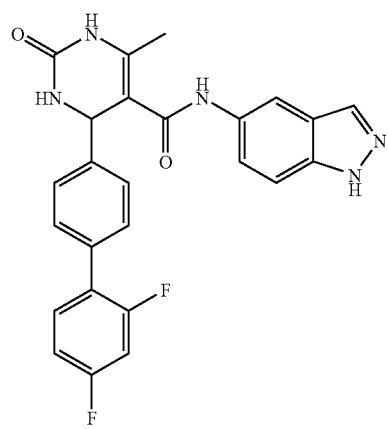

The title compound was synthesized using the procedure recited in Example 145, except 2,4-difluorophenylboronic acid was utilized. The residue was purified by reverse phase HPLC (30×100 Xterra prep, 20-80% CH₃CN/5 mM NH₄HCO₃ over 18 minutes) to afford the title compound as a white solid. MS (ES+) m/e 460 [M+H]

Example 148

N-1H-Indazol-5-yl-6-methyl-4-[4'-(methyloxy)-4-biphenylyl]-2-oxo-1,2,3,4-tetrahydro-5-pyrimidinecarboxamide

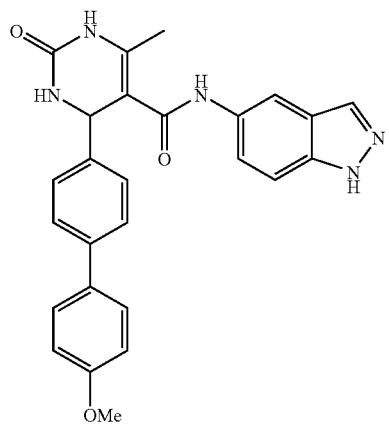

The title compound was synthesized using the procedure recited in Example 145, except 4-methoxyphenylboronic acid was utilized. The residue was purified by reverse phase HPLC (30×100 Xterra prep, 20-80% CH₃CN/5 mM NH₄HCO₃ over 18 minutes) to afford the title compound as a white solid. MS (ES+) m/e 454 [M+H]

Example 149

4-(4 Chloro-4-biphenylyl)-N-1H-indazol-5-yl-6-methyl-2-oxo-1,2,3,4-tetrahydro-5-pyrimidinecarboxamide

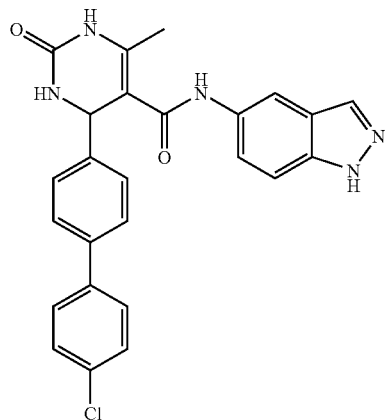

The title compound was synthesized using the procedure recited in Example 145, except 4-chlorophenylboronic acid was utilized. The residue was purified by reverse phase HPLC (30×100 Xterra prep, 30-70% CH₃CN/5 mM NH₄HCO₃ over 10 minutes) to afford the title compound as a white solid. MS (ES+) m/e 458 [M+H]

Example 150

4-(3'-Acetyl-4-biphenylyl)-N-1H-indazol-5-yl-6-methyl-2-oxo-1,2,3,4-tetrahydro-5-pyrimidinecarboxamide

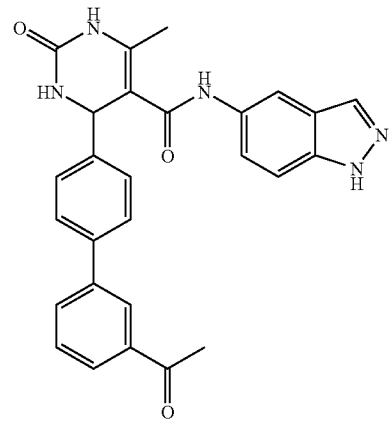

The title compound was synthesized using the procedure recited in Example 145, except 3-acetylbenzene boronic acid was utilized. The residue was purified by reverse phase HPLC (30×100 Xterra prep, 30-70% CH₃CN/5 mM NH₄HCO₃ over 10 minutes) to afford the title compound as a white solid. MS (ES+) m/e 466 [M+H]

Example 151

4-(3'-Chloro-4-biphenylyl)-N-1H-indazol-5-yl-6-methyl-2-oxo-1,2,3,4-tetrahydro-5-pyrimidinecarboxamide

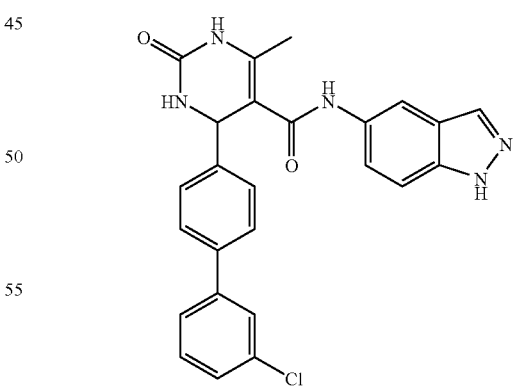

The title compound was synthesized using the procedure recited in Example 145, except 3-chlorophenyl boronic acid was utilized. The residue was purified by reverse phase HPLC (30×100 Xterra prep, 30-70% CH₃CN/5 mM NH₄HCO₃ over 10 minutes) to afford the title compound as a white solid. MS (ES+) m/e 458 [M+H]

Example 152

4-[4-(1,3-Benzodioxol-5-yl)phenyl]-N-1H-indazol-5-yl-6-methyl-2-oxo-1,2,3,4-tetrahydro-5-pyrimidinecarboxamide

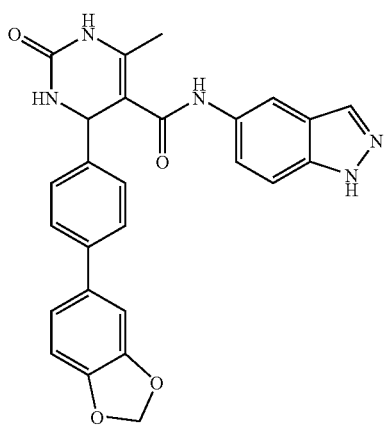

The title compound was synthesized using the procedure recited in Example 145, except 3,4-methylenedioxyphenyl boronic acid was utilized. The residue was purified by reverse phase HPLC (30×100 Xterra prep, 30-70% CH$_3$CN/5 mM NH$_4$HCO$_3$ over 10 minutes) to afford the title compound as a white solid. MS (ES+) m/e 468 [M+H]

Example 153

N-1H-Indazol-5-yl-6-methyl-2-oxo-4-[4'-(trifluoromethyl)-4-biphenylyl]-1,2,3,4-tetrahydro-5-pyrimidinecarboxamide

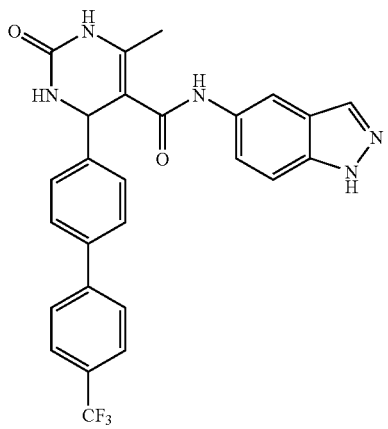

The title compound was synthesized using the procedure recited in Example 145, except 4-trifluoromethylphenyl boronic acid was utilized. The residue was purified by reverse phase HPLC (30×100 Xterra prep, 30-70% CH$_3$CN/5 mM NH$_4$HCO$_3$ over 10 minutes) to afford the title compound as a white solid. MS (ES+) m/e 492 [M+H]

Example 154

4-(2'-Chloro-4-biphenylyl)-N-1H-indazol-5-yl-6-methyl-2-oxo-1,2,3,4-tetrahydro-5-pyrimidinecarboxamide

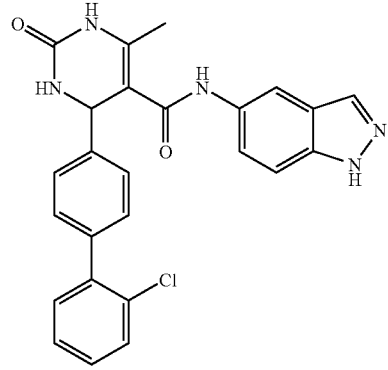

The title compound was synthesized using the procedure recited in Example 145, except 2-chlorophenyl boronic acid was utilized. The residue was purified by reverse phase HPLC (30×100 Xterra prep, 30-70% CH$_3$CN/5 mM NH$_4$HCO$_3$ over 10 minutes) to afford the title compound as a white solid. MS (ES+) m/e 458 [M+H]

Example 155

4-[4'-(Dimethylamino)-4-biphenylyl]-N-1H-indazol-5-yl-6-methyl-2-oxo-1,2,3,4-tetrahydro-5-pyrimidinecarboxamide

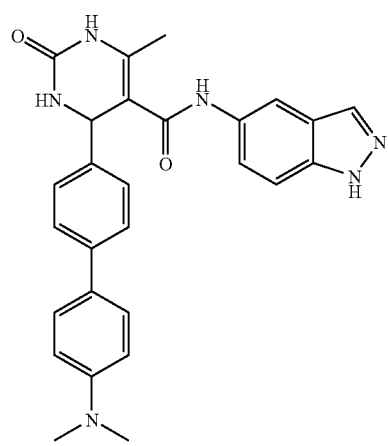

The title compound was synthesized using the procedure recited in Example 145, except 4-dimethylaminophenyl boronic acid was utilized. The residue was purified by reverse phase HPLC (30×100 Xterra prep, 15-90% CH$_3$CN/5 mM NH$_4$HCO$_3$ over 16 minutes) to afford the title compound as a white solid. MS (ES+) m/e 467 [M+H]

Example 156

4-[4'-(Dimethylamino)-4-biphenylyl]-N-1H-indazol-5-yl-6-methyl-2-oxo-1,2,3,4-tetrahydro-5-pyrimidinecarboxamide

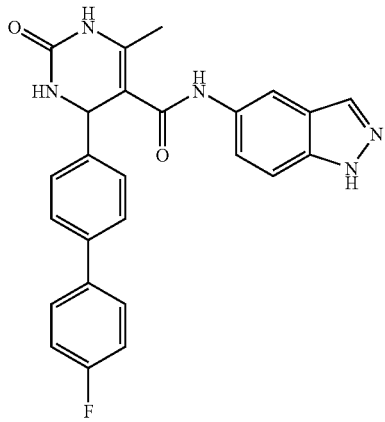

The title compound was synthesized using the procedure recited in Example 145, except 4-fluorophenyl boronic acid was utilized. The residue was purified by reverse phase HPLC (30×100 Xterra prep, 25-90% CH$_3$CN/5 mM NH$_4$HCO$_3$ over 16 minutes) to afford the title compound as a white solid. MS (ES+) m/e 442 [M+H]

Example 157

N-1H-Indazol-5-yl-6-methyl-4-[2'-(methyloxy)-4-biphenylyl]-2-oxo-1,2,3,4-tetrahydro-5-pyrimidinecarboxamide

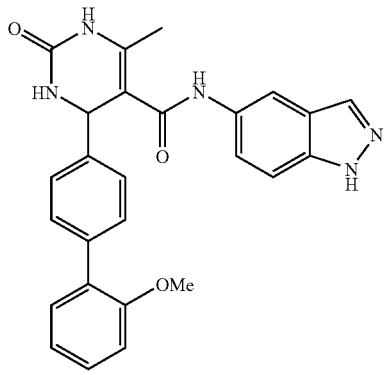

The title compound was synthesized using the procedure recited in Example 145, except 2-methoxyphenylboronic acid was utilized. The residue was purified by reverse phase HPLC (30×100 Xterra prep, 30-80% CH$_3$CN/5 mM NH$_4$HCO$_3$ over 15 minutes) to afford the title compound as a white solid. MS (ES+) m/e 454 [M+H]

Example 158

N-1H-Indazol-5-yl-6-methyl-4-[3'-(methyloxy)-4-biphenylyl]-2-oxo-1,2,3,4-tetrahydro-5-pyrimidinecarboxamide

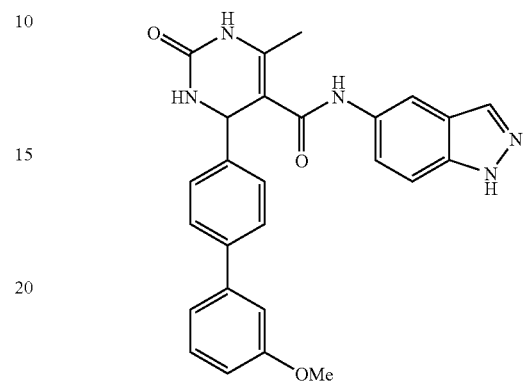

The title compound was synthesized using the procedure recited in Example 145, except 3-methoxyphenylboronic acid was utilized. The residue was purified by reverse phase HPLC (30×100 Xterra prep, 25-90% CH$_3$CN/5 mM NH$_4$HCO$_3$ over 16 minutes) to afford the title compound as a white solid. MS (ES+) m/e 454 [M+H]

Example 159

N-1H-Indazol-5-yl-4-[4-(1H-indol-5-yl)phenyl]-6-methyl-2-oxo-1,2,3,4-tetrahydro-5-pyrimidinecarboxamide

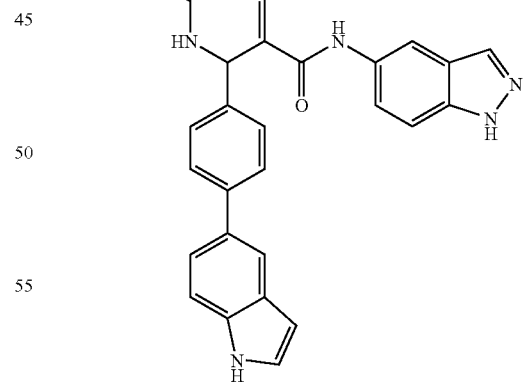

The title compound was synthesized using the procedure recited in Example 145, except indole5-boronic acid was utilized. The residue was purified by reverse phase HPLC (30×100 Xterra prep, 30-90% CH$_3$CN/5 mM NH$_4$HCO$_3$ over 16 minutes) to afford the title compound as a white solid. MS (ES+) m/e 463 [M+H]

Example 160

4-[4-(3,5-Dimethyl-4-isoxazolyl)phenyl]-N-1H-indazol-5-yl-6-methyl-2-oxo-1,2,3,4-tetrahydro-5-pyrimidinecarboxamide

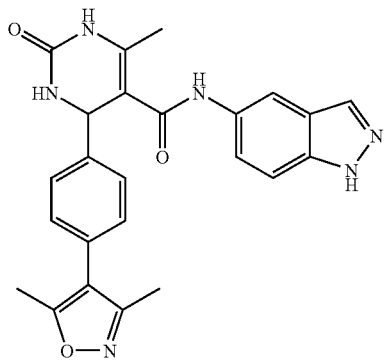

The title compound was synthesized using the procedure recited in Example 145, except 3,5-dimethyl-4-isoxazole boronic acid was utilized. The residue was purified by reverse phase HPLC (30×100 Xterra prep, 30-70% $CH_3CN$/5 mM $NH_4HCO_3$ over 10 minutes) to afford the title compound as a white solid. MS (ES+) m/e 443 [M+H]

Example 161

N-1H-Indazol-5-yl-6-methyl-2-oxo-4-[4-(1H-pyrazol-4-yl)phenyl]-1,2,3,4-tetrahydro-5-pyrimidinecarboxamide

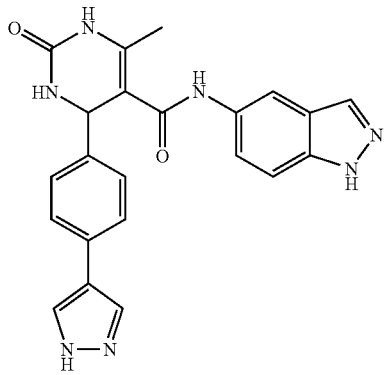

The title compound was synthesized using the procedure recited in Example 145, except pyrazole 3-boronic acid was utilized. The residue was purified by reverse phase HPLC (30×100 Xterra prep, 25-80% $CH_3CN$/5 mM $NH_4HCO_3$ over 10 minutes) to afford the title compound as a white solid. MS (ES+) m/e 414 [M+H]

Example 162

4-[3',5'-Bis(trifluoromethyl)-4-biphenylyl]-N-1H-indazol-5-yl-6-methyl-2-oxo-1,2,3,4-tetrahydro-5-pyrimidinecarboxamide

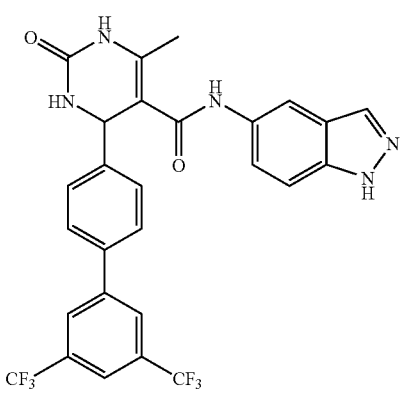

The title compound was synthesized using the procedure recited In Example 145, except 3,5-bis(trifluoromethyl)phenyl boronic acid was utilized. The crude reaction mixture was diluted with EtOAc and $H_2O$ and filtered. The phases were separated and the organic phase was washed with satd. NaCl. The organic phase was dried over sodium sulfate, filtered, and the filtrate was concentrated to afford the title compound as a pale grey solid. MS (ES+) m/e 414 [M+H]

Example 163

4-[2-Fluoro-4-(trifluoromethyl)phenyl]-N-1H-indazol-5-yl-6-methyl-2-oxo-1,2,3,4-tetrahydro-5-pyrimidinecarboxamide

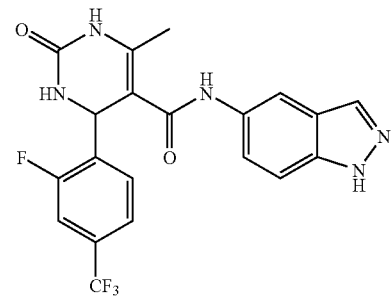

The title compound was synthesized using the procedure recited in Example 1, except 2-fluoro-4-trifluoromethylbenzaldehyde was utilized. Filtration afforded 115 mg (58%) of the product as a pale grey solid which required no additional purification. MS m/e 434 [M+H]⁺.

Example 164

4-[2-Fluoro-3-(trifluoromethyl)phenyl]-N-1H-indazol-5-yl-6-methyl-2-oxo-1,2,3,4-tetrahydro-5-pyrimidinecarboxamide

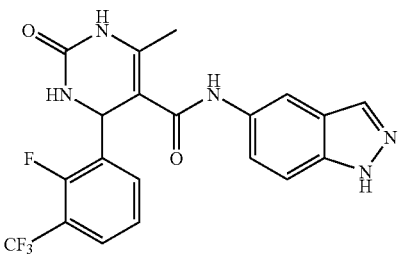

The title compound was synthesized using the procedure recited in Example 1, except 2-fluoro-3-trifluoromethylbenzaldehyde was utilized. Filtration afforded 161 mg (81%) of the product as a pale grey solid which required no additional purification. MS m/e 434 [M+H]$^+$.

Example 165

4-(2,6-Difluorophenyl)-N-1H-indazol-5-yl-6-methyl-2-oxo-1,2,3,4-tetrahydro-5-pyrimidinecarboxamide

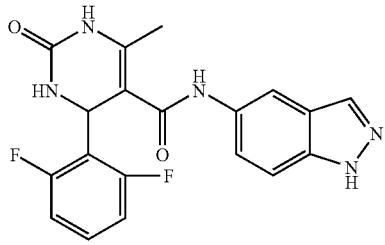

The title compound was synthesized using the procedure recited in Example 1, except 2,6-difluorobenzaldehyde was utilized. Filtration afforded 126 mg (72%) of the product as a pale grey solid which required no additional purification. MS m/e 384 [M+H]$^+$.

Example 166

4-(3'-Amino-3-biphenylyl)-N-1H-indazol-5-yl-6-methyl-2-oxo-1,2,3,4-tetrahydro-5-pyrimidinecarboxamide

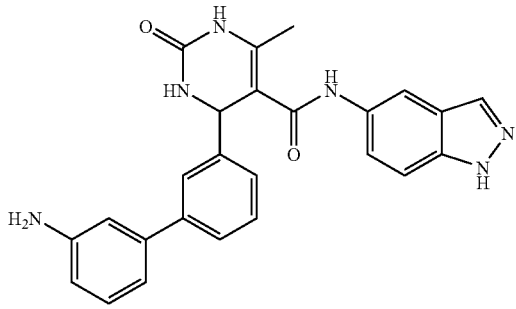

The product of Example 76 (0.100 g, 0.230 mmol, 1.00 equiv), Pd(dppf)Cl$_2$.CH$_2$Cl$_2$, and 3-aminoboronic acid (107 mg, 0.690 mmol, 3.00 equiv) were dissolved in dioxane (2 mL) and 1M aq. Na$_2$CO$_3$ (0.690 mL, 0.690 mmol, 3.00 equiv) was added. The reaction mixture was heated to 185° C. In a SmithSynthesizer for 6 minutes. The crude reaction mixture was filtered and concentrated to dryness. The residue was purified by reverse phase HPLC (30×100 Xterra prep, 25-80% CH$_3$CN/5 mM NH$_4$HCO$_3$ over 18 minutes) to afford the title compound as a white solid. MS (ES+) m/e 439 [M+H]

Example 167

4-(2',4'-Difluoro-3-biphenylyl)-N-1H-indazol-5-yl-6-methyl-2-oxo-1,2,3,4-tetrahydro-5-pyrimidinecarboxamide

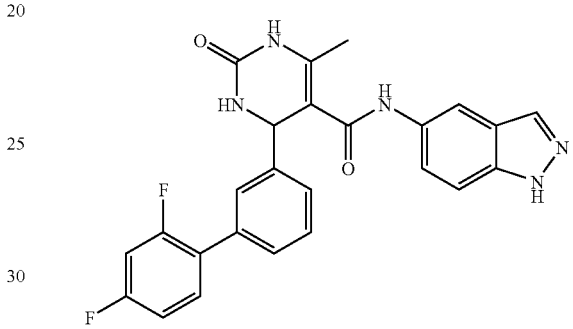

The title compound was synthesized using the procedure recited in Example 166, except 2,4-difluorophenyl boronic acid was utilized. The residue was purified by reverse phase HPLC (30×100 Xterra prep, 25-80% CH$_3$CN/5 mM NH$_4$HCO$_3$ over 18 minutes) to afford the title compound as a white solid. MS (ES+) m/e 460 [M+H]

Example 168

4-(3-Biphenylyl)-N-1H-indazol-5-yl-6-methyl-2-oxo-1,2,3,4-tetrahydro-5-pyrimidinecarboxamide

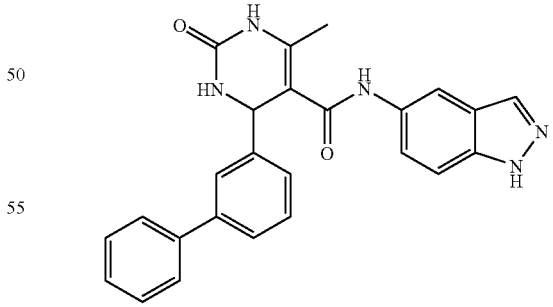

The title compound was synthesized using the procedure recited in Example 166, except phenylboronic acid was utilized. The residue was purified by reverse phase HPLC (30×100 Xterra prep, 25-80% CH$_3$CN/5 mM NH$_4$HCO$_3$ over 18 minutes) to afford the title compound as a white solid. MS (ES+) m/e 424 [M+H]

Example 169

N-1H-indazol-5-yl-6-methyl-2-oxo-4-[3-(3-thienyl)phenyl]-1,2,3,4-tetrahydro-5-pyrimidinecarboxamide

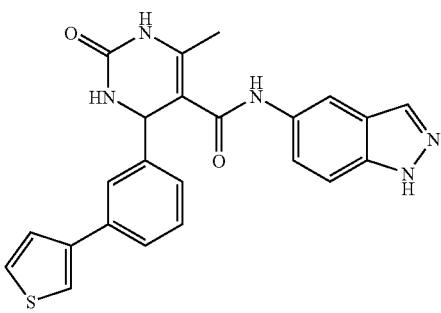

The title compound was synthesized using the procedure recited in Example 166, except thiophene 3-boronic acid was utilized. The residue was purified by reverse phase HPLC (30×100 Xterra prep, 25-80% $CH_3CN$/5 mM $NH_4HCO_3$ over 18 minutes) to afford the title compound as a white solid. MS (ES+) m/e 430 [M+H]

Example 170

N-1H-indazol-5-yl-6-methyl-2-oxo-4-{5-[4-(trifluoromethyl)phenyl]-2-thienyl}-1,2,3,4-tetrahydro-5-pyrimidinecarboxamide

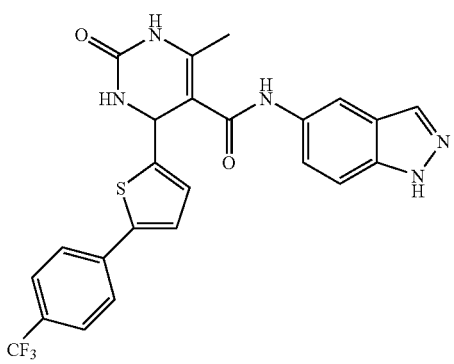

(a) 4-(5-bromo-2-thienyl)-N-1H-indazol-5-yl-6-methyl-2-oxo-1,2,3,4-tetrahydro-5-pyrimidinecarboxamide The title compound was synthesized using the procedure recited in Example 1, except 5-bromothiophene-2-carboxaldehyde was utilized. The residue was purified by flash chromatography (10→20% $MeOH/CH_2Cl_2$) to afford 325 mg (33%) of the product as a pale grey solid. $^1$H NMR (400 MHz, d6-DMSO) 12.9 (br s, 1H), 9.59 (s, 1H), 8.92 (d, 1H), 8.05 (s, 1H), 8.00 (s, 1H), 7.84 (s, 1H), 7.45 (s, 2H), 7.06 (d, 1H), 6.78 (d, 1H), 5.59 (d, 1H), 2.09 (s, 3H).

(b) 4-(5-bromo-2-thienyl)-N-1H-indazol-5-yl-6-methyl-2-oxo-1,2,3,4-tetrahydro-5-pyrimidinecarboxamide The title compound was synthesized using the procedure recited in Example 166, except 4-trifluoromethylphenyl boronic acid and the product from Step (a) were utilized. The residue was purified by reverse phase HPLC (30×100 Xterra prep, 25-80% $CH_3CN$/5 mM $NH_4HCO_3$ over 18 minutes) to afford the title compound as a white solid. MS (ES+) m/e 498 [M+H]

Example 171

4-[5-(4-Chlorophenyl)-2-thienyl]-N-1H-indazol-5-yl-6-methyl-2-oxo-1,2,3,4-tetrahydro-5-pyrimidinecarboxamide

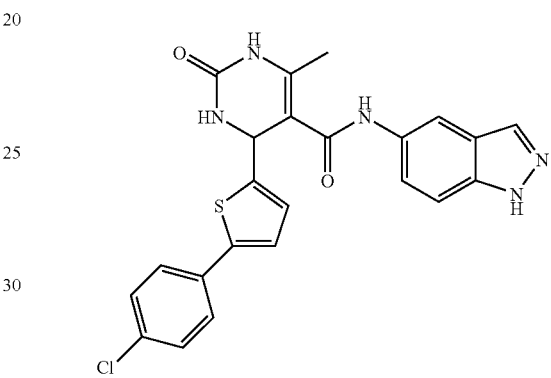

The title compound was synthesized using the procedure recited in Example 166, except 4-chlorophenyl boronic acid and the product from Example 170(a) were utilized. The residue was purified by reverse phase HPLC (30×100 Xterra prep, 25-80% $CH_3CN$/5 mM $NH_4HCO_3$ over 18 minutes) to afford the title compound as a white solid. MS (ES+) m/e 464 [M+H]

Example 172

N-1H-Indazol-5-yl-6-methyl-4-{5-[4-(methyloxy)phenyl]-2-thienyl}-2-oxo-1,2,3,4-tetrahydro-5-pyrimidinecarboxamide

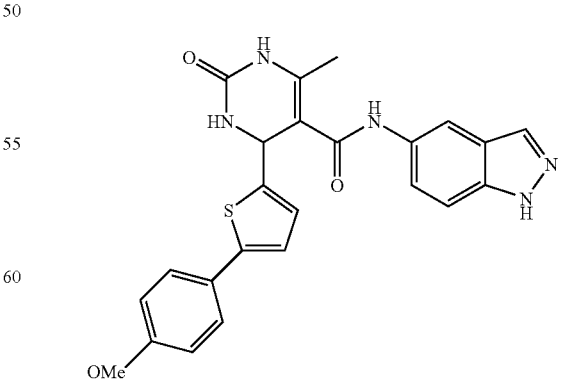

The title compound was synthesized using the procedure recited in Example 166, except 4-methoxyphenyl boronic acid and the product from Example 170(a) were utilized. The residue was purified by reverse phase HPLC (30×100 Xterra prep, 25-80% CH₃CN/5 mM NH₄HCO₃ over 18 minutes) to afford the title compound as a white solid. MS (ES+) m/e 460 [M+H]

Example 173

4-(2,3'-Bithien-5-yl)-N-1H-indazol-5-yl-6-methyl-2-oxo-1,2,3,4-tetrahydro-5-pyrimidinecarboxamide

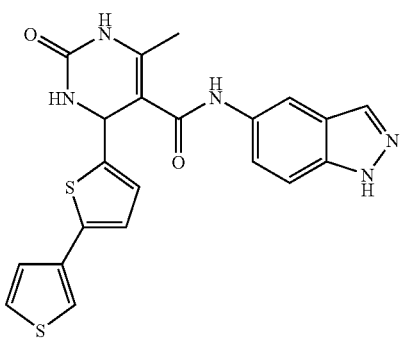

The title compound was synthesized using the procedure recited in Example 166, except thiophene 3-boronic acid and the product from Example 170(a) were utilized. The residue was purified by reverse phase HPLC (30×100 Xterra prep, 25-80% CH₃CN/5 mM NH₄HCO₃ over 18 minutes) to afford the title compound as a white solid. MS (ES+) m/e 436 [M+H]

Example 174

6-methyl-N-(3-methyl-1H-indazol-5-yl)-4-(2-naphthalenyl)-2-oxo-1,2,3,4-tetrahydro-5-pyrimidinecarboxamide

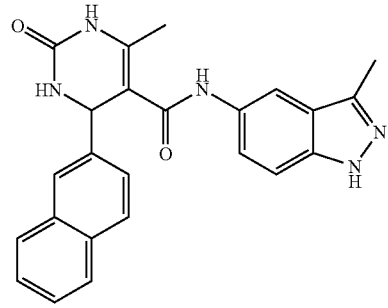

(a) N-(3-methyl-1H-indazol-5-yl)-3-oxobutanamide

5-Amino-3-methylindazole (300 mg, 2.04 mmol, 1.00 equiv) was dissolved in acetonitrile (4 mL) and diketene (151 uL, 2.04 mmol, 1.00 equiv) was added. The reaction mixture was stirred overnight, and the reaction mixture was purified directly by silica gel chromatography (50→100% EtOAc/hexanes)

(b) 6-methyl-N-(3-methyl-1H-indazol-5-yl)-4-(2-naphthalenyl)-2-oxo-1,2,3,4-tetrahydro-5-pyrimidinecarboxamide The title compound was synthesized using the procedure recited in Example 1, except 2-naphthaldehyde and the product from Step (a) were utilized. The solid product was purified by reverse phase HPLC to afford 5 mg of the title compound as a white solid. MS m/e 412 [M+H]⁺.

Scheme 7

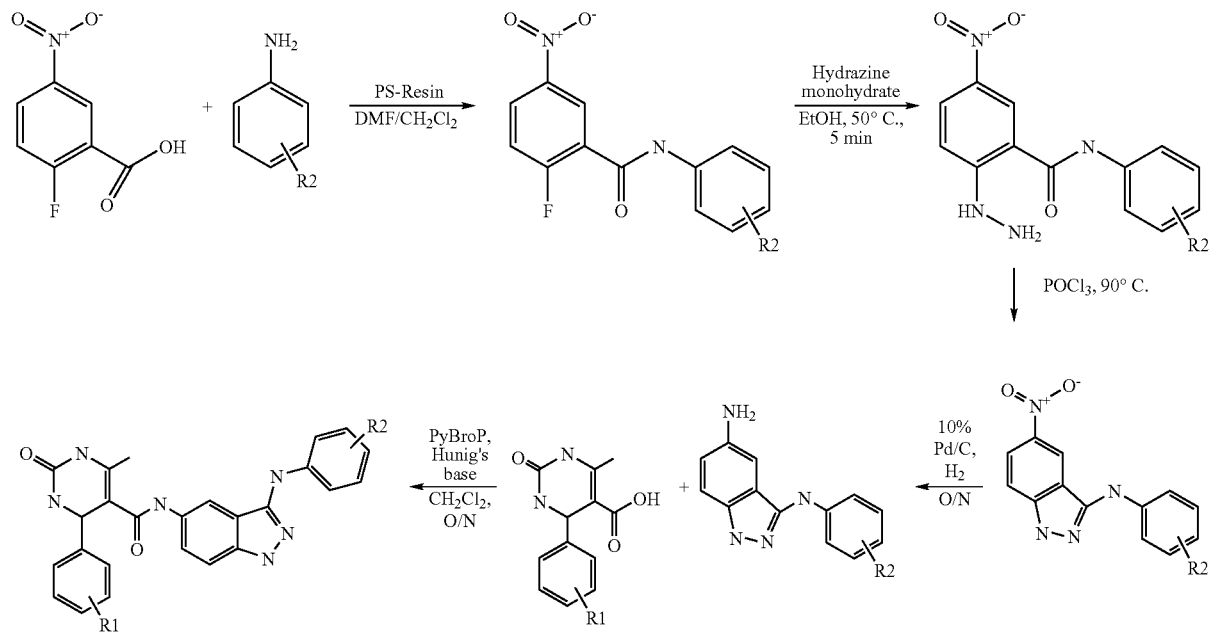

Intermediate Example 1

N³-(3-Fluoro-phenyl)-1H-indazole-3,5-diamine

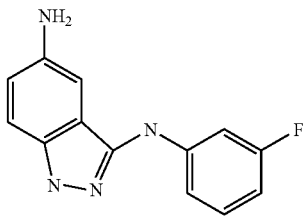

(a) 2-Fluoro-N-(3-fluoro-phenyl)-5-nitro-benzamide

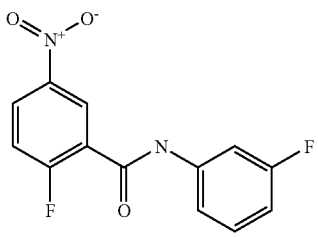

To a solution of 2-Fluoro-5-nitro benzoic acid (1.48 g, 8 mmol) and 3-Fluoro-phenyl-ammonium (920 μl, 8.5 mmol) in methylene chloride/DMF (10:1) 20 ml was added 10 g PS-resin (1.54 mmol/g). The reaction mixture was stirred at room temperature for overnight and then PS-resin was moved by filtration. The filtrate was evaporated to yield the title compound as a yellow solid. (1.11 g, 50%). MS (ESI) m/z=279 [M+H]⁺. ¹H NMR (400 MHz, d₆-DMSO) δ 10.89(s, 1H), 8.58-8.47(m, 1H), 7.72-7.67 (m, 1H), 7.45-7.42 (m, 1H), 7.00-6.98 (m, 1H), 6.37-6.28 (m, 2H)

(b) (3-Fluoro-phenyl)-(5-nitro-1H-indazol-3-yl)-amine

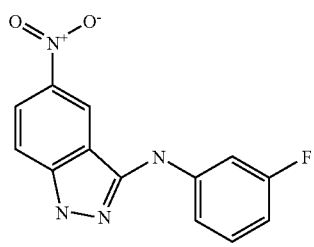

2-Fluoro-N-(3-fluoro-phenyl)-5-nitro-benzamide (1.1 μg, 4 mmol) was suspended in EtOH (25 mL) and the mixture heated to ~60° C. To the resulting solution was added hydrazine monohydrate (1.06 mL, 20 mmol). The mixture was heated at reflux for 5 minutes and a yellow solid was precipitated out. The mixture was allowed to cool to room temperature then the solid was filtered off. The solid was dissolved in phosphorous oxychloride (40 mL) and the mixture heated at 90° C. for 1.5 hr then allowed to cool to room temperature and stirred for overnight. The reaction mixture was concentrated and partitioned between EtOAc and saturated sodium bicarbonate. The organic phase was dried over MgSO₄ and concentrated to afford the title compound as a red solid (0.7 g, 64%). MS (ESI) m/z=273 [M+H]⁺. ¹H NMR (400 MHz, d₆-DMSO) δ 12.84 (s, 1H), 9.69 (s, 1H), 9.22 (d, J=2.0 Hz, 1H), 8.19 (dd, J=9.2 and 2.0 Hz, 1H), 7.77 (m, 1H), 7.54 (d, J=9.2 Hz, 1H), 7.37 (m, 2H), 6.69 (m, 1H)

(c) N³-(3-Fluoro-phenyl)-1H-indazole-3,5-diamine

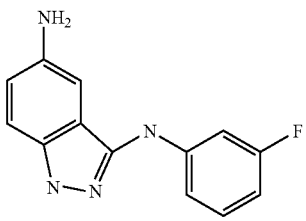

To a solution of (3-Fluoro-phenyl)-(5-nitro-1H-indazol-3-yl)-amine (0.36 g, 1.3 mmol) in methanol (10 ml) was added 10% Pd/C (72 mg). The mixture was allowed to stir at room temperature under H₂ atmosphere. After TLC showed the starting material to be consumed, the reaction was passed through a plug of celite. The filtrate was concentrated to give the title compound as an off-white solid. MS (ESI) m/z=243 [M+H]⁺.

Intermediate Example 2

4-(3,5-Difluoro-phenyl)-6-methyl-2-oxo-1,2,3,4-tetrahydro-pyrimidine-5-carboxylic acid

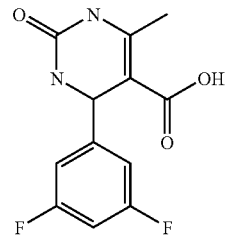

(a) 4-(3,5-Difluoro-phenyl)-6-methyl-2-oxo-1,2,3,4-tetrahydro-pyrimidine-5-carboxylic acid methyl ester

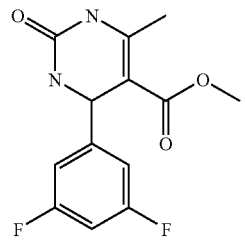

(b) 4-(3,5-Difluoro-phenyl)-6-methyl-2-oxo-1,2,3,4-tetrahydro-pyrimidine-5-carboxylic acid

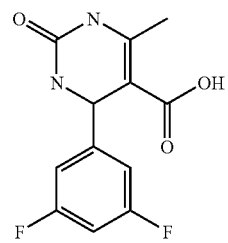

To a solution of 4-(3,5-Difluoro-phenyl)-6-methyl-2-oxo-1,2,3,4-tetrahydro-pyrimidine-5-carboxylic acid methyl ester (564 mg, 2 mmol) in MeOH (10 mL) was added 3 M NaOH (3 mL).

The reaction mixture was stirred at 60° C. for 7 hrs then EtOAc/H₂O were added to the reaction, the layers were separated. The aqueous layer was acidified to PH~1 with 6 N HCl and was washed with EtOAc three times. The combined organic layers were dried over MgSO₄ and concentrated to afford the title compound as a white solid (427 mg, 80%). MS (ESI) m/z=269 [M+H]⁺.

Intermediate Example 3

3-(4-Fluoro-phenyl)-1H-indazol-5-ylamine

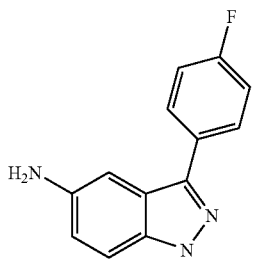

(a) 3-Iodo-5-nitro-1H-indazole

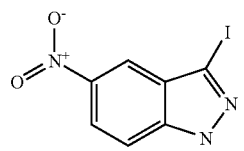

Iodine (1.6 g, 6.4 mmol) and KOH (0.67 g, 12 mmol) were successfully added into a solution of 5-nitro-1H-indazole (520 mg, 3.2 mmol) in DMF. The reaction mixture was stirred at room temperature for overnight and then 10% Na₂S₂O₅ was poured into the mixture. The titled compound (0.84 g, 91%) was filtered off as a yellow solid. MS (ESI) m/z=290 [M+H]⁺. ¹H NMR (400 MHz, d₆-DMSO) δ 14.15(s, 1H), 8.36(d, J=2 Hz, 1H), 8.26 (dd, J=2 and 9 Hz, 1H), 7.78 (d, J=9 Hz, 1H)

(b) 3-Iodo-5-nitro-indazole-1-carboxylic acid tert-butyl ester

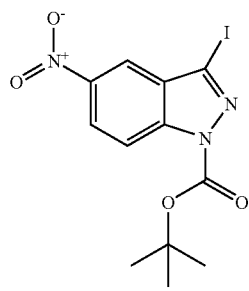

To a solution of 3-Iodo-5-nitro-1H-indazole (578 mg, 2 mmol) and (BoC)₂O (458 mg, 2.1 mmol) was added 2.2 mL 1M NaOH. The mixture was stirred at room temperature for overnight and then cold water was added into the mixture. The titled compound (0.75 g, 96%) was filtered off as a light yellow solid. ¹H NMR (400 MHz, CDCl3) δ 8.48 (m, 2H), 8.32 (d, J=10 Hz, 1H), 1.76 (s, 9H)

(c) 3-(4-Fluoro-phenyl)-1H-indazol-5-ylamine

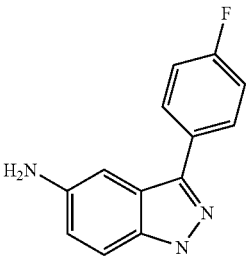

To a solution of 3-Iodo-5-nitro-indazole-1-carboxylic acid tert-butyl ester (389 mg, 1 mmol), 4-flurophenylboronic acid (280 mg, 2 mmol) and Pd(dppf)₂Cl₂ (82 mg, 0.1 mmol) in DMF (8 ml) was added 2M K₂CO₃ solution 2 mL. The reaction mixture was heated at 95° C. for overnight under nitrogen. After the reaction mixture was cooled to room temperature water was added and a black solid (180 mg) was filtered off.

The obtained black solid was dissolved in MeOH (5 mL). To the solution was added 45 mg 10% Pd/C then the reaction mixture was allowed to stir under H₂. After TLC showed the starting material to be consumed, the reaction was passed through a plug of celite. The filtrate was concentrated to give the title compound (120 mg, 53% two steps) as an off-white solid. MS (ESI) m/z=228 [M+H]⁺.

Example 175

4-(3,5-Difluoro-phenyl)-6-methyl-2-oxo-1,2,3,4-tetrahydro-pyrimidine-5-carboxylic acid [3-(3-fluoro-phenylamino)-1H-indazol-5-yl]-amide

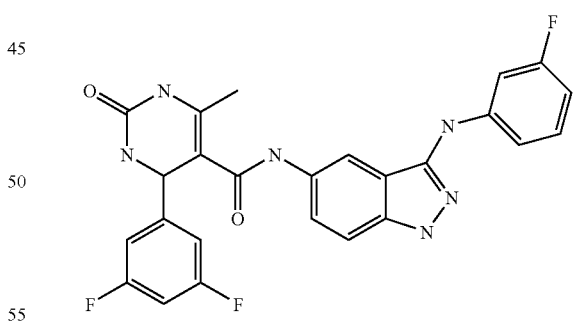

To a solution 4-(3,5-Difluoro-phenyl)-6-methyl-2-oxo-1, 2,3,4-tetrahydro-pyrimidine-5-carboxylic acid (17 mg, 0.057 mmol), N³-(3-Fluoro-phenyl)-1H-indazole-3,5-diamine (14 mg, 0.057 mmol) and PyBroP (27 mg, 0.057 mmol) in methylene chloride (1 ml) was added diisopropylethylamine 20 μL. The mixture was allowed to stir overnight at room temperature and the titled compound (7.5 mg, 25%) was purified with HPLC. MS (ESI) m/z=493 [M+H]⁺. ¹H NMR (400 MHz, d₆-DMSO) δ8.02 (s, 1H), 7.38-7.30(m, 3H), 7.23-7.15 (m, 2H), 7.01-6.99 (m, 2H), 6.91-6.86 (m, 2H), 6.58-6.53 (m, 1H)

Example 176

4-(3,5-Difluoro-phenyl)-6-methyl-2-oxo-1,2,3,4-tetrahydro-pyrimidine-5-carboxylic acid [3-(3,5-difluoro-phenylamino)-1H-indazol-5-yl]-amide

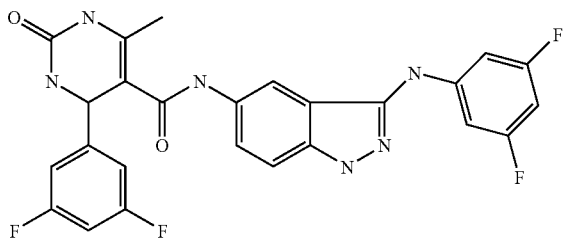

The titled compound was prepared following the procedure of Example 175 using 4-(3,5-Difluoro-phenyl)-6-methyl-2-oxo-1,2,3,4-tetrahydro-pyrimidine-5-carboxylic acid, $N^3$-(3,5-difluoro-phenyl)-1H-indazole-3,5-diamine, PyBroP and diisopropylethylamine in methylene chloride. MS (ESI) m/z 511 [M+H]$^+$.

Example 177

4-(3,4-Difluoro-phenyl)-6-methyl-2-oxo-1,2,3,4-tetrahydro-pyrimidine-5-carboxylic acid [3-(3,5-difluoro-phenylamino)-1H-indazol-5-yl]-amide

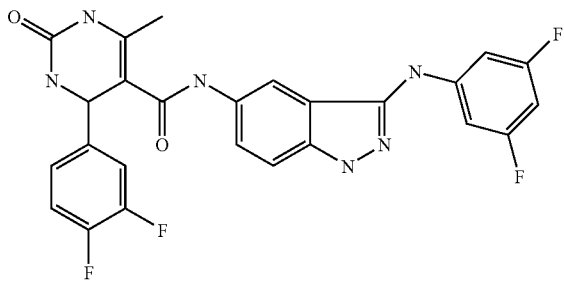

The titled compound was prepared following the procedure of Example 175 using 4-(3,4-Difluoro-phenyl)-6-methyl-2-oxo-1,2,3,4-tetrahydro-pyrimidine-5-carboxylic acid, $N^3$-(3,5-difluoro-phenyl)-1H-indazole-3,5-diamine, PyBroP and diisopropylethylamine in methylene chloride. MS (ESI) m/z=511 [M+H]$^+$.

Example 178

4-(3,4-Difluoro-phenyl)-6-methyl-2-oxo-1,2,3,4-tetrahydro-pyrimidine-5-carboxylic acid [3-(3-fluoro-phenylamino)-1H-indazol-5-yl]-amide

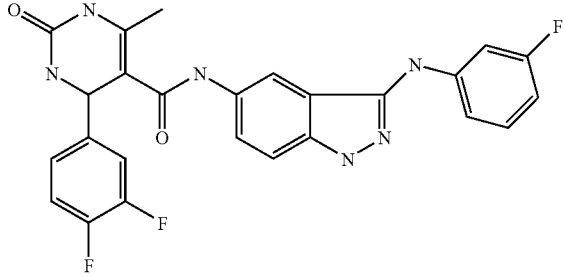

The titled compound was prepared following the procedure of Example 175 using 4-(3,4-Difluoro-phenyl)-6-methyl-2-oxo-1,2,3,4-tetrahydro-pyrimidine-5-carboxylic acid, $N^3$-(3-fluoro-phenyl)-1H-indazole-3,5-diamine, PyBroP and diisopropylethylamine in methylene chloride. MS (ESI) m/z=493 [M+H]$^+$.

Example 179

6-Methyl-2-oxo-4-(4-trifluoromethyl-phenyl)-1,2,3,4-tetrahydro-pyrimidine-5-carboxylic acid [3-(3,5-difluoro-phenylamino)-1H-indazol-5-yl]-amide

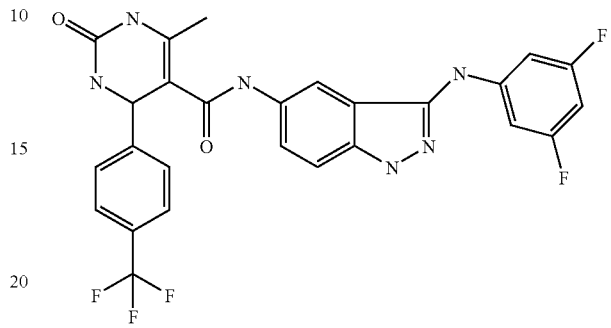

The titled compound was prepared following the procedure of Example 175 using 6-Methyl-2-oxo-4-(4-trifluoromethyl-phenyl)-1,2,3,4-tetrahydro-pyrimidine-5-carboxylic acid, $N^3$-(3,5-difluoro-phenyl)-1H-indazole-3,5-diamine, PyBroP and diisopropylethylamine in methylene chloride. MS (ESI) m/z=543 [M+H]$^+$.

Example 180

4-(4-Chloro-2-fluoro-phenyl)-6-methyl-2-oxo-1,2,3,4-tetrahydro-pyrimidine-5-carboxylic acid [3-(3,5-difluoro-phenylamino)-1H-indazol-5-yl]-amide

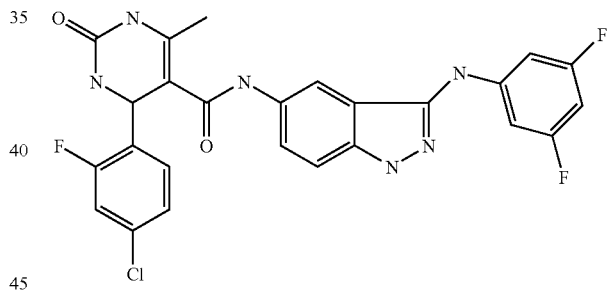

The titled compound was prepared following the procedure of Example 175 using 4-(4-Chloro-2-fluoro-phenyl)-6-methyl-2-oxo-1,2,3,4-tetrahydro-pyrimidine-5-carboxylic acid, $N^3$-(3,5-difluoro-phenyl)-1H-indazole-3,5-diamine, PyBroP and diisopropylethylamine in methylene chloride. MS (ESI) m/z=527 [M+H]$^+$.

Example 181

4-(3,5-Difluoro-phenyl)-6-methyl-2-oxo-1,2,3,4-tetrahydro-pyrimidine-5-carboxylic acid [3-(4-fluoro-phenylamino)-1H-indazol-5-yl]-amide

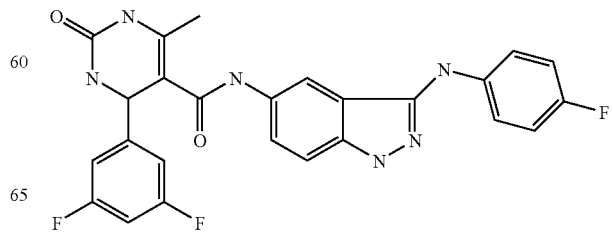

The titled compound was prepared following the procedure of Example 175 using 4-(3,5-Difluoro-phenyl)-6-methyl-2-oxo-1,2,3,4-tetrahydro-pyrimidine-5-carboxylic acid, $N^3$-(4-fluoro-phenyl)-1H-indazole-3,5-diamine, PyBroP and diisopropylethylamine in methylene chloride. MS (ESI) m/z=493 [M+H]$^+$.

Example 182

4-(3,4-Difluoro-phenyl)-6-methyl-2-oxo-1,2,3,4-tetrahydro-pyrimidine-5-carboxylic acid [3-(4-fluoro-phenylamino)-1H-indazol-5-yl]-amide

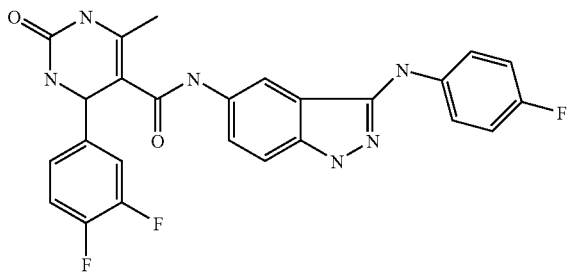

The titled compound was prepared following the procedure of Example 175 using 4-(3,4-Difluoro-phenyl)-6-methyl-2-oxo-1,2,3,4-tetrahydro-pyrimidine-5-carboxylic acid, $N^3$-(4-fluoro-phenyl)-1H-indazole-3,5-diamine, PyBroP and diisopropylethylamine in methylene chloride. MS (ESI) m/z=493 [M+H]$^+$.

Example 183

4-(3,5-Difluoro-phenyl)-6-methyl-2-oxo-1,2,3,4-tetrahydro-pyrimidine-5-carboxylic acid [3-(4-fluoro-phenyl)-1H-indazol-5-yl]-amide

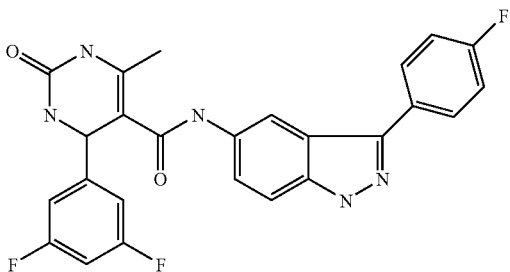

The titled compound was prepared following the procedure of Example 175 using 4-(3,5-Difluoro-phenyl)-6-methyl-2-oxo-1,2,3,4-tetrahydro-pyrimidine-5-carboxylic acid, 3-(4-Fluoro-phenyl)-1H-indazole-5-ylamine, PyBroP and diisopropylethylamine in methylene chloride. MS (ESI) m/z=478 [M+H]$^+$.

Biological Data

ROCK kinase assay:

ROCK inhibitor activity was determined using human recombinant ROCK1 kinase domain (amino acid 2-543) expressed in Sf9 cells (see WO9967283). The enzyme was purified using His-tag NTA column and Source15 HPLC chromatography. The assay of Rock-1 activity involved incubation with peptide substrate and ATP$^{33}$, the subsequent incorporation of P$^{33}$ into the peptide was quantified by Scintillation Proximity Assay (SPA—Amersham Pharmacia).

For IC50 determination, test compounds were typically dissolved at 10 mM in 100% DMSO, with subsequent serial dilution in 100% DMSO. Compounds were typically assayed over an eleven point dilution range with a concentration in the assay of 50 uM to 0.8 nM, in 3-fold dilutions. IC50 values were calculated by bespoke curve fitting software and then converted to pIC50.

Assays were performed in opaque, white walled, 384 well plates, In a total assay volume of 20 ul. The assays contained: 1 nM hROCK1; 1 uM biotinylated peptide (biotin-Ahx-AKRRRLSSLRA-CONH2; the peptide sequence is shown in SEQ ID NO:1); 1 uM ATP; 1.85 kBq per well ATP(γ-33 P); 25 mM Hepes pH 7.4; 15 mM MgCl$_2$; 0.015% BSA. The reactions were incubated at 22° C. for 120 minutes, then terminated by the addition of a 50 ul solution containing 60 mM EDTA and streptavidin PVT SPA beads. The SPA beads were added to a concentration of 0.14 mg per well. The plates were allowed to incubate at 22° C. for 10 minutes before centrifugation at 1500 rpm for 1 minute. P$^{33}$ incorporation was quantified by scintillation counting in a Packard TopCount.

All exemplified Examples 1-183 were run with the recited ROCK kinase assay and showed inhibitory activity versus Rock-1 with a pIC$_{50}$ of 5.0 or greater.

Aurora A Fluorescence Polarization Inhibitor Competition Assay:

Small molecule inhibitors conjugated to fluorophores can be used to measure the binding of ATP-competitive test compounds to protein kinases by fluorescence polarization (FP). When the FP ligand is bound to the enzyme there is a high signal due to decreased rotation of the ligand. Upon release of the ligand, such as when an inhibitor binds to the enzyme, the signal is decreased because the ligand can rotate quickly.

Aurora kinase domain (104403) is expressed in baculovirus/Sf9 system as a fusion protein to GST and purified to >70% purity by affinity chromatography. For use in the assay the enzyme is diluted in 2×Aurora A assay buffer (50 mM HEPES (pH 7.5), 1 mM CHAPS) to 40 nM. Compounds are dissolved and serially diluted in 100% DMSO, 1 uL is added to assay plates (Costar #3710 384-well black plates). FP ligand, GW805818X, is diluted in 2×fp solution (50 mM HEPES (pH 7.5), 1 mM CHAPS, 20 mM MgCl2, 2 mM DTT) so that the final FP ligand concentration is 5 nM. 20 uL of fp solution with the diluted fluorescent ligand is added to assay plates followed by the addition of GST-Aurora A. The assay plates are incubated for-45 minutes and read on a fluorescence polarization plate reader.

For dose response curves, data were normalized and expressed as % inhibition using the formula 100*(1-(U-C$_2$)/(C$_1$-C$_2$)) where U is the unknown value, C1 is the average of the high signal (0% Inhibition) and C$_2$ is the average of the low signal (100% inhibition) control wells. Curve fitting was performed with the following equation: y=A+((B−A)/(1+(10^x/10^C)^D)), where A is the minimum response, B is the maximum response, C is the log10XC50, and D is the slope. The results for each compound were recorded as pIC50 values (—C in the above equation).

All exemplified Examples 1-183 were run with the recited Aurora A kinase assay and showed inhibitory activity versus Aurora-A with a pIC$_{50}$ of 5.0 or greater.

What is claimed is:

1. A compound of Formula (I):

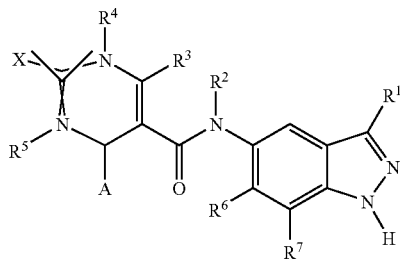

or a salt thereof:
wherein:
  ⌒ indicates a single bond;
  X is =O or =S;
  A is selected from —CH$_2$OCH$_2$R''' where R''' is phenyl;
    cyclohexenylene;

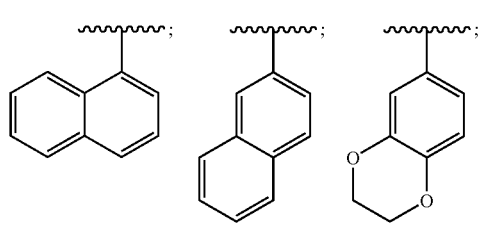

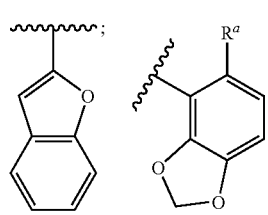

where R$^a$ is —H or
  —OCH$_3$;

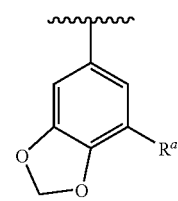

where R$^a$ is —Cl;

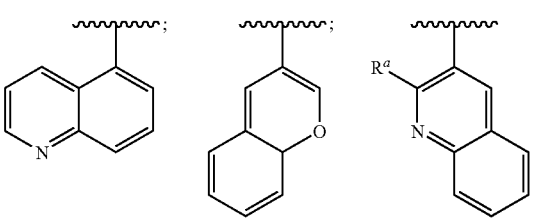

where R$^a$ is —H or —Cl;

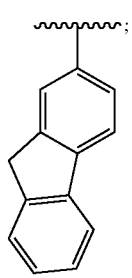

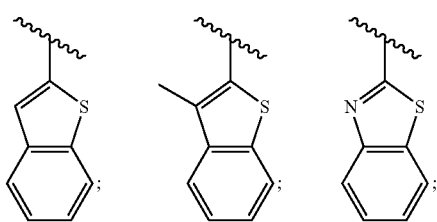

-continued

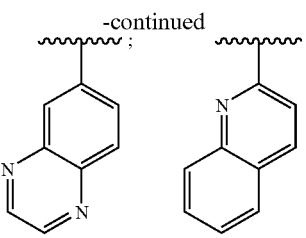

optionally substituted with —OH;

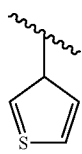

optionally substituted with —Br;

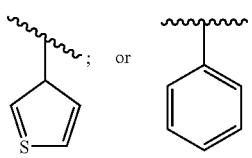 or optionally substituted with one or more groups selected form —Cl, —CF₃, and methoxy;

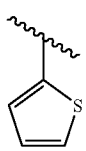

optionally substituted with —CH₃, phenyl, —Cl, ethynyl substituted with phenyl,

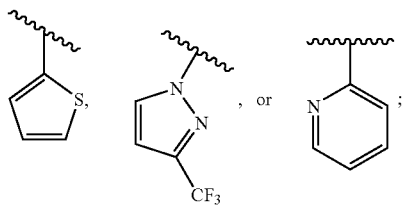

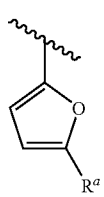

where $R^a$ is —CH₃ or phenyl substituted with —Cl;

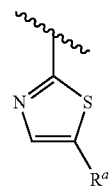

where $R^a$ is phenyl or —SCH₃;
C₁-C₆ alkyl optionally substituted with aryl or

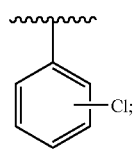

C₂-C₆ alkenyl optionally substituted with phenyl, where the phenyl is optionally substituted with —NO₂ or methoxy;
C₂-C₆ alkenyl independently di-substituted with phenyl and/or —Cl;
C₁-C₈ alkenyl optionally substituted with furanyl;
C₂-C₈ alkynyl substituted with phenyl;
or A is

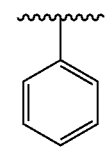

optionally substituted with one or more groups selected from —F, —Cl; —Br; —F; methoxy, ethoxy; —S(O)₂CH₃; —N(H)S(O)₂CH₃; —S(O)₂NH₂; —C(O)NH₂; —C(O)OH; —CN; —OH; —O(CH₂)ᵣOH, where r is 1, 2, 3, or 4; —N(H)C(O)CH₃; —CF₃, —NO₂; phenoxy, benzyloxy; —OCF₃; —NR$^a$R$^a$ where R$^a$ is independently —H, —CH₃ or —CH₂CH₃;

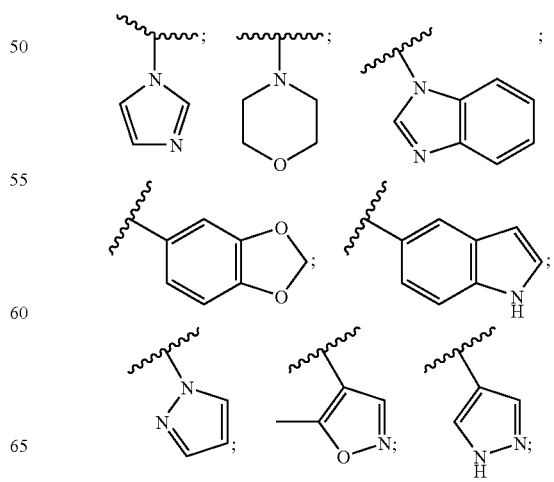

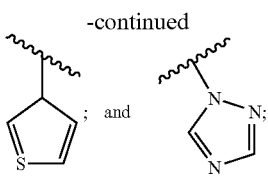

or A is

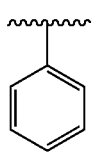

substituted with phenyl wherein said phenyl is optionally substituted with one or more groups selected from —Cl, —F; —CF$_3$; methoxy or —NR$^a$R$^a$ where R$^a$ is independently —H, —CH$_3$ or —CH$_2$CH$_3$; or —C(O)CH$_3$;

R$^1$ is —H, —NH(R'), —Cl, —Br, —CH$_3$, or phenyl optionally substituted with —F;

R$^2$ is —H or —CH$_3$ and R$^3$ is —H, C$_1$-C$_3$ alkyl, —CH$_2$OCH$_3$, or furanyl; or R$^2$ and R$^3$ together with the ring and atoms to which they are attached form a fused ring system;

R$^4$ is —H, —CH$_3$, —CH$_2$CH$_3$, or benzyl;
R$^5$ is —H or —CH$_3$;
R$^6$ is —H, —Cl, or —F; and
R$^7$ is —H or —Cl.

2. A compound selected from the group consisting of:
4-(4-fluorophenyl)-N-1H-indazol-5-yl-6-methyl-2-oxo-1,2,3,4-tetrahydro-5-pyrimidinecarboxamide;
4-[3,4-bis(ethyloxy)phenyl]-N-1H-indazol-5-yl-6-methyl-2-oxo-1,2,3,4-tetrahydro-5-pyrimidinecarboxamide;
N-1H-indazol-5-yl-6-methyl-4-[4-(methylsulfonyl)phenyl]-2-oxo-1,2,3,4-tetrahydro-5-pyrimidinecarboxamide;
N-1H-indazol-5-yl-6-methyl-2-oxo-4-(3-thienyl)-1,2,3,4-tetrahydro-5-pyrimidinecarboxamide;
N-1H-indazol-5-yl-4,6-dimethyl-2-oxo-1,2,3,4-tetrahydro-5-pyrimidinecarboxamide;
N-1H-indazol-5-yl-6-methyl-4-(1-naphthalenyl)-2-oxo-1,2,3,4-tetrahydro-5-pyrimidinecarboxamide;
N-1H-indazol-5-yl-6-methyl-4-(2-naphthalenyl)-2-oxo-1,2,3,4-tetrahydro-5-pyrimidinecarboxamide;
4-{5-[(1H-indazol-5-ylamino)carbonyl]-6-methyl-2-oxo-1,2,3,4-tetrahydro-4-pyrimidinyl}benzoic acid;
4-(2,4-difluorophenyl)-N-1H-indazol-5-yl-6-methyl-2-oxo-1,2,3,4-tetrahydro-5-pyrimidinecarboxamide;
N-1H-indazol-5-yl-6-methyl-4-[3-(methyloxy)phenyl]-2-oxo-1,2,3,4-tetrahydro-5-pyrimidinecarboxamide;
N-1H-indazol-5-yl-6-methyl-4-[2-(methyloxy)phenyl]-2-oxo-1,2,3,4-tetrahydro-5-pyrimidinecarboxamide;
4-(4-cyanophenyl)-N-1H-indazol-5-yl-6-methyl-2-oxo-1,2,3,4-tetrahydro-5-pyrimidinecarboxamide;
3-{5-[(1H-indazol-5-ylamino)carbonyl]-6-methyl-2-oxo-1,2,3,4-tetrahydro-4-pyrimidinyl}benzoic acid;
4-(2-fluorophenyl)-N-1H-indazol-5-yl-6-methyl-2-oxo-1,2,3,4-tetrahydro-5-pyrimidinecarboxamide;
4-(3-chloro-4-fluorophenyl)-N-1H-indazol-5-yl-6-methyl-2-oxo-1,2,3,4-tetrahydro-5-pyrimidinecarboxamide;
4-{3-[(2-hydroxyethyl)oxy]phenyl}-N-1H-indazol-5-yl-6-methyl-2-oxo-1,2,3,4-tetrahydro-5-pyrimidinecarboxamide;
4-(4-bromo-2-thienyl)-N-1H-indazol-5-yl-6-methyl-2-oxo-1,2,3,4-tetrahydro-5-pyrimidinecarboxamide;
4-(4-hydroxyphenyl)-N-1H-indazol-5-yl-6-methyl-2-oxo-1,2,3,4-tetrahydro-5-pyrimidinecarboxamide;
4-(4-chloro-2-fluorophenyl)-N-1H-indazol-5-yl-6-methyl-2-oxo-1,2,3,4-tetrahydro-5-pyrimidinecarboxamide;
N-1H-indazol-5-yl-6-methyl-4-{3-[(methylsulfonyl)amino]phenyl}-2-oxo-1,2,3,4-tetrahydro-5-pyrimidinecarboxamide;
N-1H-indazol-5-yl-6-methyl-2-oxo-4-(6-quinoxalinyl)-1,2,3,4-tetrahydro-5-pyrimidinecarboxamide;
4-[4-(aminosulfonyl)phenyl]-N-1H-indazol-5-yl-6-methyl-2-oxo-1,2,3,4-tetrahydro-5-pyrimidinecarboxamide;
N-1H-indazol-5-yl-6-methyl-2-oxo-4-(2-quinolinyl)-1,2,3,4-tetrahydro-5-pyrimidinecarboxamide;
4-[3-fluoro-4-(methyloxy)phenyl]-N-1H-indazol-5-yl-6-methyl-2-oxo-1,2,3,4-tetrahydro-5-pyrimidinecarboxamide;
4-(3-cyanophenyl)-N-1H-indazol-5-yl-6-methyl-2-oxo-1,2,3,4-tetrahydro-5-pyrimidinecarboxamide;
4-(1H-imidazol-1-yl)-N-1H-indazol-5-yl-6-methyl-2-oxo-1,2,3,4-tetrahydro-5-pyrimidinecarboxamide;
N-1H-indazol-5-yl-6-methyl-2-oxo-4-(3-quinolinyl)-1,2,3,4-tetrahydro-5-pyrimidinecarboxamide;
N-1H-indazol-5-yl-6-methyl-2-oxo-4-[(E)-2-phenylethenyl]-1,2,3,4-tetrahydro-5-pyrimidinecarboxamide;
N-1H-indazol-5-yl-6-methyl-2-oxo-4-[4-(trifluoromethyl)phenyl]-1,2,3,4-tetrahydro-5-pyrimidinecarboxamide;
4-(4-chlorophenyl)-N-1H-indazol-5-yl-6-methyl-2-oxo-1,2,3,4-tetrahydro-5-pyrimidinecarboxamide;
4-[4-(acetylamino)phenyl]-N-1H-indazol-5-yl-6-methyl-2-oxo-1,2,3,4-tetrahydro-5-pyrimidinecarboxamide;
4-(2-chlorophenyl)-N-1H-indazol-5-yl-6-methyl-2-oxo-1,2,3,4-tetrahydro-5-pyrimidinecarboxamide;
4-(2,3-dihydro-1,4-benzodioxin-6-yl)-N-1H-indazol-5-yl-6-methyl-2-oxo-1,2,3,4-tetrahydro-5-pyrimidinecarboxamide;
4-(3-hydroxyphenyl)-N-1H-indazol-5-yl-6-methyl-2-oxo-1,2,3,4-tetrahydro-5-pyrimidinecarboxamide;
4-(8-hydroxy-2-quinolinyl)-N-1H-indazol-5-yl-6-methyl-2-oxo-1,2,3,4-tetrahydro-5-pyrimidinecarboxamide;
4-[3,4-bis(methyloxy)phenyl]-N-1H-indazol-5-yl-6-methyl-2-oxo-1,2,3,4-tetrahydro-5-pyrimidinecarboxamide;
4-[2-(4-chlorophenyl)ethyl]-N-1H-indazol-5-yl-6-methyl-2-oxo-1,2,3,4-tetrahydro-5-pyrimidinecarboxamide;
4-[3-(1H-imidazol-1-yl)phenyl]-N-1H-indazol-5-yl-6-methyl-2-oxo-1,2,3,4-tetrahydro-5-pyrimidinecarboxamide;
4-(3-chlorophenyl)-N-1H-indazol-5-yl-6-methyl-2-oxo-1,2,3,4-tetrahydro-5-pyrimidinecarboxamide;
4-[4-(aminocarbonyl)phenyl]-N-1H-indazol-5-yl-6-methyl-2-oxo-1,2,3,4-tetrahydro-5-pyrimidinecarboxamide;
4-(4-fluorophenyl)-N-1H-indazol-5-yl-6-(1-methylethyl)-2-oxo-1,2,3,4-tetrahydro-5-pyrimidinecarboxamide;
4-(4-fluorophenyl)-6-(2-furanyl)-N-1H-indazol-5-yl-2-oxo-1,2,3,4-tetrahydro-5-pyrimidinecarboxamide;

4-(4-fluorophenyl)-N-1H-indazol-5-yl-1,6-dimethyl-2-oxo-1,2,3,4-tetrahydro-5-pyrimidinecarboxamide;
N-1H-indazol-5-yl-1,6-dimethyl-4-(2-naphthalenyl)-2-oxo-1,2,3,4-tetrahydro-5-pyrimidinecarboxamide;
N-1H-indazol-5-yl-6-methyl-4-(2-naphthalenyl)-2-thioxo-1,2,3,4-tetrahydro-5-pyrimidinecarboxamide;
4-(4-fluorophenyl)-N-1H-indazol-5-yl-6-methyl-2-thioxo-1,2,3,4-tetrahydro-5-pyrimidinecarboxamide;
N-1H-indazol-5-yl-6-methyl-4-(3-thienyl)-2-thioxo-1,2,3,4-tetrahydro-5-pyrimidinecarboxamide;
4-(4-fluorophenyl)-N-1H-indazol-5-yl-1,3,6-trimethyl-2-oxo-1,2,3,4-tetrahydro-5-pyrimidinecarboxamide;
4-(4-fluorophenyl)-N-1H-indazol-5-yl-6-methyl-2-oxo-1-(phenylmethyl)-1,2,3,4-tetrahydro-5-pyrimidinecarboxamide;
4-(4-fluorophenyl)-N-1H-indazol-5-yl-N,6-dimethyl-2-oxo-1,2,3,4-tetrahydro-5-pyrimidinecarboxamide;
4-(4-fluorophenyl)-N-1H-indazol-5-yl-2-oxo-1,2,3,4-tetrahydro-5-pyrimidinecarboxamide;
1-ethyl-4-(4-fluorophenyl)-N-1H-indazol-5-yl-6-methyl-2-oxo-1,2,3,4-tetrahydro-5-pyrimidinecarboxamide; and
N-(3-amino-1H-indazol-5-yl)-4-(4-fluorophenyl)-6-methyl-2-oxo-1,2,3,4-tetrahydro-5-pyrimidinecarboxamide;
or a salt thereof.

3. A compound selected from the group consisting of:
N-1H-indazol-5-yl-6-methyl-2-oxo-4-phenyl-1,2,3,4-tetrahydro-5-pyrimidinecarboxamide;
N-1H-indazol-5-yl-6-methyl-2-oxo-4-(4-pyridinyl)-1,2,3,4-tetrahydro-5-pyrimidinecarboxamide;
Methyl 3-{5-[(1H-indazol-5-ylamino)carbonyl]-6-methyl-2-oxo-1,2,3,4-tetrahydro-4-pyrimidinyl}benzoate;
Methyl 4-{5-[(1H-indazol-5-ylamino)carbonyl]-6-methyl-2-oxo-1,2,3,4-tetrahydro-4-pyrimidinyl}benzoate;
4-(3-furanyl)-N-1H-indazol-5-yl-6-methyl-2-oxo-1,2,3,4-tetrahydro-5-pyrimidinecarboxamide;
N-1H-indazol-5-yl-6-methyl-4-(2-methylpropyl)-2-oxo-1,2,3,4-tetrahydro-5-pyrimidinecarboxamide;
N-1H-indazol-5-yl-6-methyl-2-oxo-4-(2-phenylethyl)-1,2,3,4-tetrahydro-5-pyrimidinecarboxamide;
N-1H-indazol-5-yl-6-methyl-4-(4-nitrophenyl)-2-oxo-1,2,3,4-tetrahydro-5-pyrimidinecarboxamide;
4-(3-cyano-4-fluorophenyl)-N-1H-indazol-5-yl-6-methyl-2-oxo-1,2,3,4-tetrahydro-5-pyrimidinecarboxamide;
4-(4-fluoro-3-nitrophenyl)-N-1H-indazol-5-yl-6-methyl-2-oxo-1,2,3,4-tetrahydro-5-pyrimidinecarboxamide;
4-[2-hydroxy-4-(methyloxy)phenyl]-N-1H-indazol-5-yl-6-methyl-2-oxo-1,2,3,4-tetrahydro-5-pyrimidinecarboxamide; and
4-(4-biphenylyl)-N-1H-indazol-5-yl-6-methyl-2-oxo-1,2,3,4-tetrahydro-5-pyrimidinecarboxamide;
and salts thereof.

4. A compound selected from the group consisting of:
4-(1-benzofuran-2-yl)-N-1H-indazol-5-yl-6-methyl-2-oxo-1,2,3,4-tetrahydro-5-pyrimidinecarboxamide;
4-[(E)-2-(2-furanyl)ethenyl]-N-1H-indazol-5-yl-6-methyl-2-oxo-1,2,3,4-tetrahydro-5-pyrimidinecarboxamide;
N-1H-indazol-5-yl-6-methyl-4-(5-methyl-2-furanyl)-2-oxo-1,2,3,4-tetrahydro-5-pyrimidinecarboxamide;
4-[5-(4-chlorophenyl)-2-furanyl]-N-1H-indazol-5-yl-6-methyl-2-oxo-1,2,3,4-tetrahydro-5-pyrimidinecarboxamide;
4-(1,3-benzodioxol-5-yl)-N-1H-indazol-5-yl-6-methyl-2-oxo-1,2,3,4-tetrahydro-5-pyrimidinecarboxamide;
N-1H-indazol-5-yl-6-methyl-2-oxo-4-[4-(phenyloxy)phenyl]-1,2,3,4-tetrahydro-5-pyrimidinecarboxamide;
N-1H-indazol-5-yl-6-methyl-2-oxo-4-[3-(phenyloxy)phenyl]-1,2,3,4-tetrahydro-5-pyrimidinecarboxamide;
N-1H-indazol-5-yl-6-methyl-2-oxo-4-(5-quinolinyl)-1,2,3,4-tetrahydro-5-pyrimidinecarboxamide;
4-(3-Bromophenyl)-N-1H-indazol-5-yl-6-methyl-2-oxo-1,2,3,4-tetrahydro-5-pyrimidinecarboxamide;
N-1H-indazol-5-yl-6-methyl-2-oxo-4-(5-phenyl-2-thienyl)-1,2,3,4-tetrahydro-5-pyrimidinecarboxamide;
N-1H-indazol-5-yl-6-methyl-4-[(E)-2-(2-nitrophenyl)ethenyl]-2-oxo-1,2,3,4-tetrahydro-5-pyrimidinecarboxamide;
N-1H-indazol-5-yl-6-methyl-4-{(E)-2-[4-(methyloxy)phenyl]ethenyl}-2-oxo-1,2,3,4-tetrahydro-5-pyrimidinecarboxamide;
4-(1-cyclohexen-1-yl)-N-1H-indazol-5-yl-6-methyl-2-oxo-1,2,3,4-tetrahydro-5-pyrimidinecarboxamide;
N-1H-indazol-5-yl-6-methyl-4-{(E)-2-[2-(methyloxy)phenyl]ethenyl}-2-oxo-1,2,3,4-tetrahydro-5-pyrimidinecarboxamide;
4-(2,2-diphenylethenyl)-N-1H-indazol-5-yl-6-methyl-2-oxo-1,2,3,4-tetrahydro-5-pyrimidinecarboxamide;
4-[(Z)-1-chloro-2-phenylethenyl]-N-1H-indazol-5-yl-6-methyl-2-oxo-1,2,3,4-tetrahydro-5-pyrimidinecarboxamide;
N-1H-indazol-5-yl-6-methyl-2-oxo-4-{[(phenylmethyl)oxy]methyl}-1,2,3,4-tetrahydro-5-pyrimidinecarboxamide;
N-1H-indazol-5-yl-6-methyl-2-oxo-4-(phenylethynyl)-1,2,3,4-tetrahydro-5-pyrimidinecarboxamide;
4-(2,2'-bithien-5-yl)-N-1H-indazol-5-yl-6-methyl-2-oxo-1,2,3,4-tetrahydro-5-pyrimidinecarboxamide;
N-1H-indazol-5-yl-6-methyl-4-(3-methyl-1-benzothien-2-yl)-2-oxo-1,2,3,4-tetrahydro-5-pyrimidinecarboxamide;
4-(5-chloro-2-thienyl)-N-1H-indazol-5-yl-6-methyl-2-oxo-1,2,3,4-tetrahydro-5-pyrimidinecarboxamide;
N-1H-indazol-5-yl-6-methyl-2-oxo-4-(1,3-thiazol-2-yl)-1,2,3,4-tetrahydro-5-pyrimidinecarboxamide;
N-1H-indazol-5-yl-6-methyl-4-(3-methyl-2-thienyl)-2-oxo-1,2,3,4-tetrahydro-5-pyrimidinecarboxamide;
4-(1-benzothien-2-yl)-N-1H-indazol-5-yl-6-methyl-2-oxo-1,2,3,4-tetrahydro-5-pyrimidinecarboxamide;
N-1H-indazol-5-yl-6-methyl-2-oxo-4-{3-[(phenylmethyl)oxy]phenyl}-1,2,3,4-tetrahydro-5-pyrimidinecarboxamide;
4-(9H-fluoren-2-yl)-N-1H-indazol-5-yl-6-methyl-2-oxo-1,2,3,4-tetrahydro-5-pyrimidinecarboxamide;
4-(3-bromo-4-fluorophenyl)-N-1H-indazol-5-yl-6-methyl-2-oxo-1,2,3,4-tetrahydro-5-pyrimidinecarboxamide;
N-1H-indazol-5-yl-6-methyl-4-[7-(methyloxy)-1,3-benzodioxol-5-yl]-2-oxo-1,2,3,4-tetrahydro-5-pyrimidinecarboxamide;
4-(1,3-benzodioxol-4-yl)-N-1H-indazol-5-yl-6-methyl-2-oxo-1,2,3,4-tetrahydro-5-pyrimidinecarboxamide;
N-1H-indazol-5-yl-6-methyl-2-oxo-4-{3-[(trifluoromethyl)oxy]phenyl}-1,2,3,4-tetrahydro-5-pyrimidinecarboxamide;
N-1H-indazol-5-yl-6-methyl-2-oxo-4-[3-(trifluoromethyl)phenyl]-1,2,3,4-tetrahydro-5-pyrimidinecarboxamide;
4-[3-hydroxy-4-(methyloxy)phenyl]-N-1H-indazol-5-yl-6-methyl-2-oxo-1,2,3,4-tetrahydro-5-pyrimidinecarboxamide;

4-(5-chloro-1,3-benzodioxol-4-yl)-N-1H-indazol-5-yl-6-methyl-2-oxo-1,2,3,4-tetrahydro-5-pyrimidinecarboxamide;
N-1H-indazol-5-yl-6-methyl-2-oxo-4-[5-(2-pyridinyl)-2-thienyl]-1,2,3,4-tetrahydro-5-pyrimidinecarboxamide;
N-1H-indazol-5-yl-6-methyl-2-oxo-4-(2-phenyl-1,3-thiazol-4-yl)-1,2,3,4-tetrahydro-5-pyrimidinecarboxamide;
N-1H-indazol-5-yl-6-methyl-4-[5-(methylthio)-2-thienyl]-2-oxo-1,2,3,4-tetrahydro-5-pyrimidinecarboxamide;
4-(1,3-benzothiazol-2-yl)-N-1H-indazol-5-yl-6-methyl-2-oxo-1,2,3,4-tetrahydro-5-pyrimidinecarboxamide;
4-(2H-chromen-3-yl)-N-1H-indazol-5-yl-6-methyl-2-oxo-1,2,3,4-tetrahydro-5-pyrimidinecarboxamide;
N-1H-indazol-5-yl-6-methyl-2-oxo-4-[5-(phenylethynyl)-2-thienyl]-1,2,3,4-tetrahydro-5-pyrimidinecarboxamide;
N-1H-indazol-5-yl-6-methyl-2-oxo-4-[4-(phenylethynyl)-2-thienyl]-1,2,3,4-tetrahydro-5-pyrimidinecarboxamide;
N-1H-indazol-5-yl-6-methyl-4-(5-methyl-2-thienyl)-2-oxo-1,2,3,4-tetrahydro-5-pyrimidinecarboxamide;
N-1H-indazol-5-yl-6-methyl-4-{5-[1-methyl-5-(trifluoromethyl)-1H-pyrazol-3-yl]-2-thienyl}-2-oxo-1,2,3,4-tetrahydro-5-pyrimidinecarboxamide;
N-1H-indazol-5-yl-6-methyl-2-oxo-4-[4-(2-pyridinyl)phenyl]-1,2,3,4-tetrahydro-5-pyrimidinecarboxamide;
4-[4-(dimethylamino)phenyl]-N-1H-indazol-5-yl-6-methyl-2-oxo-1,2,3,4-tetrahydro-5-pyrimidinecarboxamide;
4-[4-(diethylamino)phenyl]-N-1H-indazol-5-yl-6-methyl-2-oxo-1,2,3,4-tetrahydro-5-pyrimidinecarboxamide;
4-(2-chloro-3-quinolinyl)-N-1H-indazol-5-yl-6-methyl-2-oxo-1,2,3,4-tetrahydro-5-pyrimidinecarboxamide;
N-1H-indazol-5-yl-6-methyl-4-(4-methyl-3,4-dihydro-2H-1,4-benzoxazin-7-yl)-2-oxo-1,2,3,4-tetrahydro-5-pyrimidinecarboxamide;
N-1H-indazol-5-yl-6-methyl-4-[4-(4-morpholinyl)phenyl]-2-oxo-1,2,3,4-tetrahydro-5-pyrimidinecarboxamide;
N-1H-indazol-5-yl-6-methyl-2-oxo-4-[4-(2-thienyl)phenyl]-1,2,3,4-tetrahydro-5-pyrimidinecarboxamide;
N-1H-indazol-5-yl-6-methyl-2-oxo-4-[4-(1H-pyrazol-1-yl)phenyl]-1,2,3,4-tetrahydro-5-pyrimidinecarboxamide;
N-1H-indazol-5-yl-6-methyl-2-oxo-4-[4-(1H-1,2,4-triazol-1-yl)phenyl]-1,2,3,4-tetrahydro-5-pyrimidinecarboxamide;
4-[2,3-difluoro-4-(trifluoromethyl)phenyl]-N-1H-indazol-5-yl-6-methyl-2-oxo-1,2,3,4-tetrahydro-5-pyrimidinecarboxamide;
4-[4-(1H-benzimidazol-1-yl)phenyl]-N-1H-indazol-5-yl-6-methyl-2-oxo-1,2,3,4-tetrahydro-5-pyrimidinecarboxamide;
4-(4-Fluorophenyl)-N-[3-(4-fluorophenyl)-1H-indazol-5-yl]-6-methyl-2-oxo-1,2,3,4-tetrahydro-5-pyrimidinecarboxamide;
N-(3-Chloro-1H-indazol-5-yl)-4-(4-fluorophenyl)-6-methyl-2-oxo-1,2,3,4-tetrahydro-5-pyrimidinecarboxamide;
N-(3-Chloro-1H-indazol-5-yl)-6-methyl-4-(2-naphthalenyl)-2-oxo-1,2,3,4-tetrahydro-5-pyrimidinecarboxamide;
1-ethyl-4-(4-fluorophenyl)-N-1H-indazol-5-yl-6-methyl-2-oxo-1,2,3,4-tetrahydro-5-pyrimidinecarboxamide;
4-(4-fluorophenyl)-N-1H-indazol-5-yl-2-oxo-6-propyl-1,2,3,4-tetrahydro-5-pyrimidinecarboxamide;
N-1H-indazol-5-yl-4-(2-naphthalenyl)-2-oxo-6-propyl-1,2,3,4-tetrahydro-5-pyrimidinecarboxamide;
4-(4-fluorophenyl)-N-1H-indazol-5-yl-6-[(methyloxy)methyl]-2-oxo-1,2,3,4-tetrahydro-5-pyrimidinecarboxamide;
4-(4-fluorophenyl)-6-(1H-indazol-5-yl)hexahydro-1H-pyrrolo[3,4-d]pyrimidine-2,5-dione;
N-1H-indazol-5-yl-6-methyl-4-(3-nitrophenyl)-2-oxo-1,2,3,4-tetrahydro-5-pyrimidinecarboxamide;
4-(4-chlorophenyl)-6-(1H-indazol-5-yl)-3,4,6,7-tetrahydro-1H-pyrrolo[3,4-d]pyrimidine-2,5-dione;
4-(3-aminophenyl)-N-1H-indazol-5-yl-6-methyl-2-oxo-1,2,3,4-tetrahydro-5-pyrimidinecarboxamide;
4-(3,5-Dibromophenyl)-N-1H-indazol-5-yl-6-methyl-2-oxo-1,2,3,4-tetrahydro-5-pyrimidinecarboxamide;
4-(3,4-Difluorophenyl)-N-1H-indazol-5-yl-6-methyl-2-oxo-1,2,3,4-tetrahydro-5-pyrimidinecarboxamide;
N-1H-Indazol-5-yl-6-methyl-4-[(E)-1-methyl-2-phenylethenyl]-2-oxo-1,2,3,4-tetrahydro-5-pyrimidinecarboxamide;
4-(4-Fluorophenyl)-N-1H-indazol-5-yl-3,6-dimethyl-2-oxo-1,2,3,4-tetrahydro-5-pyrimidinecarboxamide;
6-Ethyl-4-(4-fluorophenyl)-N-1H-indazol-5-yl-2-oxo-1,2,3,4-tetrahydro-5-pyrimidinecarboxamide;
N-(6-Chloro-1H-indazol-5-yl)-4-(4-fluorophenyl)-6-methyl-2-oxo-1,2,3,4-tetrahydro-5-pyrimidinecarboxamide;
N-(6-Chloro-1H-indazol-5-yl)-6-methyl-4-(2-naphthalenyl)-2-oxo-1,2,3,4-tetrahydro-5-pyrimidinecarboxamide;
N-(6-Fluoro-1H-indazol-5-yl)-4-(4-fluorophenyl)-6-methyl-2-oxo-1,2,3,4-tetrahydro-5-pyrimidinecarboxamide;
N-(7-Chloro-1H-indazol-5-yl)-4-(4-fluorophenyl)-6-methyl-2-oxo-1,2,3,4-tetrahydro-5-pyrimidinecarboxamide;
N-(7-Chloro-1H-indazol-5-yl)-6-methyl-4-(2-naphthalenyl)-2-oxo-1,2,3,4-tetrahydro-5-pyrimidinecarboxamide;
N-(3-bromo-1H-indazol-5-yl)-4-(4-fluorophenyl)-6-methyl-2-oxo-1,2,3,4-tetrahydro-5-pyrimidinecarboxamide;
N-(3-bromo-1H-indazol-5-yl)-4-(2-naphthyl)-6-methyl-2-oxo-1,2,3,4-tetrahydro-5-pyrimidinecarboxamide;
N-(3-bromo-1H-indazol-5-yl)-4-(3-thiophenyl)-6-methyl-2-oxo-1,2,3,4-tetrahydro-5-pyrimidinecarboxamide;
4-(4-Bromophenyl)-N-1H-indazol-5-yl-6-methyl-2-oxo-1,2,3,4-tetrahydro-5-pyrimidinecarboxamide;
4-(3'-Amino-4-biphenylyl)-N-1H-indazol-5-yl-6-methyl-2-oxo-1,2,3,4-tetrahydro-5-pyrimidinecarboxamide;
N-1H-Indazol-5-yl-6-methyl-2-oxo-4-[4-(2-thienyl)phenyl]-1,2,3,4-tetrahydro-5-pyrimidinecarboxamide;
4-(2',4'-Difluoro-4-biphenylyl)-N-1H-indazol-5-yl-6-methyl-2-oxo-1,2,3,4-tetrahydro-5-pyrimidinecarboxamide;
N-1H-Indazol-5-yl-6-methyl-4-[4'-(methyloxy)-4-biphenylyl]-2-oxo-1,2,3,4-tetrahydro-5-pyrimidinecarboxamide;
4-(4'-Chloro-4-biphenylyl)-N-1H-indazol-5-yl-6-methyl-2-oxo-1,2,3,4-tetrahydro-5-pyrimidinecarboxamide;
4-(3'-Acetyl-4-biphenylyl)-N-1H-indazol-5-yl-6-methyl-2-oxo-1,2,3,4-tetrahydro-5-pyrimidinecarboxamide;
4-(3'-Chloro-4-biphenylyl)-N-1H-indazol-5-yl-6-methyl-2-oxo-1,2,3,4-tetrahydro-5-pyrimidinecarboxamide;

4-[4-(1,3-Benzodioxol-5-yl)phenyl]-N-1H-indazol-5-yl-6-methyl-2-oxo-1,2,3,4-tetrahydro-5-pyrimidinecarboxamide;

N-1H-Indazol-5-yl-6-methyl-2-oxo-4-[4'-(trifluoromethyl)-4-biphenylyl]-1,2,3,4-tetrahydro-5-pyrimidinecarboxamide;

4-(2'-Chloro-4-biphenylyl)-N-1H-indazol-5-yl-6-methyl-2-oxo-1,2,3,4-tetrahydro-5-pyrimidinecarboxamide;

4-[4'-(Dimethylamino)-4-biphenylyl]-N-1H-indazol-5-yl-6-methyl-2-oxo-1,2,3,4-tetrahydro-5-pyrimidinecarboxamide;

4-[4'-(Dimethylamino)-4-biphenylyl]-N-1H-indazol-5-yl-6-methyl-2-oxo-1,2,3,4-tetrahydro-5-pyrimidinecarboxamide;

N-1H-Indazol-5-yl-6-methyl-4-[2'-(methyloxy)-4-biphenylyl]-2-oxo-1,2,3,4-tetrahydro-5-pyrimidinecarboxamide;

N-1H-Indazol-5-yl-6-methyl-4-[3'-(methyloxy)-4-biphenylyl]-2-oxo-1,2,3,4-tetrahydro-5-pyrimidinecarboxamide;

N-1H-Indazol-5-yl-4-[4-(1H-indol-5-yl)phenyl]-6-methyl-2-oxo-1,2,3,4-tetrahydro-5-pyrimidinecarboxamide;

4-[4-(3,5-Dimethyl-4-isoxazolyl)phenyl]-N-1H-indazol-5-yl-6-methyl-2-oxo-1,2,3,4-tetrahydro-5-pyrimidinecarboxamide;

N-1H-Indazol-5-yl-6-methyl-2-oxo-4-[4-(1H-pyrazol-4-yl)phenyl]-1,2,3,4-tetrahydro-5-pyrimidinecarboxamide;

4-[3',5'-Bis(trifluoromethyl)-4-biphenylyl]-N-1H-indazol-5-yl-6-methyl-2-oxo-1,2,3,4-tetrahydro-5-pyrimidinecarboxamide;

4-[2-Fluoro-4-(trifluoromethyl)phenyl]-N-1H-indazol-5-yl-6-methyl-2-oxo-1,2,3,4-tetrahydro-5-pyrimidinecarboxamide;

4-[2-Fluoro-3-(trifluoromethyl)phenyl]-N-1H-indazol-5-yl-6-methyl-2-oxo-1,2,3,4-tetrahydro-5-pyrimidinecarboxamide;

4-(2,6-Difluorophenyl)-N-1H-indazol-5-yl-6-methyl-2-oxo-1,2,3,4-tetrahydro-5-pyrimidinecarboxamide;

4-(3'-Amino-3-biphenylyl)-N-1H-indazol-5-yl-6-methyl-2-oxo-1,2,3,4-tetrahydro-5-pyrimidinecarboxamide;

4-(2',4'-Difluoro-3-biphenylyl)-N-1H-indazol-5-yl-6-methyl-2-oxo-1,2,3,4-tetrahydro-5-pyrimidinecarboxamide;

4-(3-Biphenylyl)-N-1H-indazol-5-yl-6-methyl-2-oxo-1,2,3,4-tetrahydro-5-pyrimidinecarboxamide;

N-1H-Indazol-5-yl-6-methyl-2-oxo-4-[3-(3-thienyl)phenyl]-1,2,3,4-tetrahydro-5-pyrimidinecarboxamide;

N-1H-Indazol-5-yl-6-methyl-2-oxo-4-{5-[4-(trifluoromethyl)phenyl]-2-thienyl}-1,2,3,4-tetrahydro-5-pyrimidinecarboxamide;

4-[5-(4-Chlorophenyl)-2-thienyl]-N-1H-indazol-5-yl-6-methyl-2-oxo-1,2,3,4-tetrahydro-5-pyrimidinecarboxamide;

N-1H-Indazol-5-yl-6-methyl-4-{5-[4-(methyloxy)phenyl]-2-thienyl}-2-oxo-1,2,3,4-tetrahydro-5-pyrimidinecarboxamide;

4-(2,3'-Bithien-5-yl)-N-1H-indazol-5-yl-6-methyl-2-oxo-1,2,3,4-tetrahydro-5-pyrimidinecarboxamide; and 6-methyl-N-(3-methyl-1H-indazol-5-yl)-4-(2-naphthalenyl)-2-oxo-1,2,3,4-tetrahydro-5-pyrimidinecarboxamide;

and salts thereof.

5. A compound selected from the group consisting of:

4-(3,5-difluoro-phenyl)-6-methyl-2-oxo-1,2,3,4-tetrahydro-pyrimidine-5-carboxylic acid [3-(3-fluoro-phenylamino)-1H-indazol-5-yl]-amide;

4-(3,5-difluoro-phenyl)-6-methyl-2-oxo-1,2,3,4-tetrahydro-pyrimidine-5-carboxylic acid [3-(3,5-difluoro-phenylamino)-1H-indazol-5-yl]-amide;

4-(3,4-difluoro-phenyl)-6-methyl-2-oxo-1,2,3,4-tetrahydro-pyrimidine-5-carboxylic acid [3-(3,5-difluoro-phenylamino)-1H-indazol-5-yl]-amide;

4-(3,4-difluoro-phenyl)-6-methyl-2-oxo-1,2,3,4-tetrahydro-pyrimidine-5-carboxylic acid [3-(3-fluoro-phenylamino)-1H-indazol-5-yl]-amide;

6-methyl-2-oxo-4-(4-trifluoromethyl-phenyl)-1,2,3,4-tetrahydro-pyrimidine-5-carboxylic acid [3-(3,5-difluoro-phenylamino)-1H-indazol-5-yl]-amide;

4-(4-chloro-2-fluoro-phenyl)-6-methyl-2-oxo-1,2,3,4-tetrahydro-pyrimidine-5-carboxylic acid [3-(3,5-difluoro-phenylamino)-1H-indazol-5-yl]-amide;

4-(3,5-difluoro-phenyl)-6-methyl-2-oxo-1,2,3,4-tetrahydro-pyrimidine-5-carboxylic acid [3-(4-fluoro-phenylamino)-1H-indazol-5-yl]-amide;

4-(3,4-difluoro-phenyl)-6-methyl-2-oxo-1,2,3,4-tetrahydro-pyrimidine-5-carboxylic acid [3-(4-fluoro-phenylamino)-1H-indazol-5-yl]-amide; and 4-(3,5-difluoro-phenyl)-6-methyl-2-oxo-1,2,3,4-tetrahydro-pyrimidine-5-carboxylic acid [3-(4-fluoro-phenyl)-1H-indazol-5-yl]-amide;

and salts thereof.

6. A pharmaceutical composition comprising a therapeutically effective amount of a compound as claimed in claim 1 or a salt thereof and one or more pharmaceutically acceptable carriers, diluents and excipients.

7. A method of treating rheumatoid arthritis in a human, said method comprising administering to said mammal a therapeutically effective amount of a compound as claimed in claim 1 or a salt thereof.

* * * * *